United States Patent
Ross et al.

(10) Patent No.: US 9,603,829 B2
(45) Date of Patent: Mar. 28, 2017

(54) HSP90 INHIBITORS WITH MODIFIED TOXICITY

(71) Applicant: THE REGENTS OF THE UNIVERSITY OF COLORADO, a body corporate, Denver, CO (US)

(72) Inventors: David Ross, Niwot, CO (US); David Siegal, Denver, CO (US); Christopher J. Moody, Leicestershire (GB); Russell Richard Anthony Kitson, Leicestershire (GB)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/357,230

(22) PCT Filed: Nov. 14, 2012

(86) PCT No.: PCT/US2012/065111
§ 371 (c)(1),
(2) Date: May 9, 2014

(87) PCT Pub. No.: WO2013/074695
PCT Pub. Date: May 23, 2013

(65) Prior Publication Data
US 2014/0315845 A1  Oct. 23, 2014

Related U.S. Application Data

(60) Provisional application No. 61/559,144, filed on Nov. 14, 2011, provisional application No. 61/702,222, filed on Sep. 17, 2012.

(51) Int. Cl.
| | |
|---|---|
| *A61K 31/337* | (2006.01) |
| *A61K 31/395* | (2006.01) |
| *A61K 31/4427* | (2006.01) |
| *A61K 31/704* | (2006.01) |
| *A61K 45/06* | (2006.01) |
| *C07D 225/06* | (2006.01) |
| *C07D 401/04* | (2006.01) |
| *C07D 405/04* | (2006.01) |
| *C07D 409/04* | (2006.01) |

(52) U.S. Cl.
CPC .......... *A61K 31/337* (2013.01); *A61K 31/395* (2013.01); *A61K 31/4427* (2013.01); *A61K 31/704* (2013.01); *A61K 45/06* (2013.01); *C07D 225/06* (2013.01); *C07D 401/04* (2013.01); *C07D 405/04* (2013.01); *C07D 409/04* (2013.01)

(58) Field of Classification Search
CPC ... C07D 409/04; C07D 225/06; C07D 401/04
See application file for complete search history.

(56) References Cited

U.S. PATENT DOCUMENTS

| | | |
|---|---|---|
| 2,601,994 A | 7/1952 | Richman |
| 6,015,659 A | 1/2000 | Welch et al. |
| 6,855,705 B1 | 2/2005 | Tian et al. |
| 6,872,715 B2 | 3/2005 | Santi et al. |
| 7,282,493 B2 | 10/2007 | Adams et al. |
| 7,776,849 B2 | 8/2010 | Yamaguchi et al. |
| 8,551,964 B2 | 10/2013 | Ross et al. |
| 2005/0054625 A1 | 3/2005 | Johnson, Jr. et al. |
| 2005/0227955 A1* | 10/2005 | Adams ................. C07D 211/60 514/183 |
| 2006/0019941 A1 | 1/2006 | Adams et al. |
| 2006/0205705 A1* | 9/2006 | Ross et al. .................... 514/183 |
| 2009/0209494 A1 | 8/2009 | Martin et al. |

FOREIGN PATENT DOCUMENTS

| | | |
|---|---|---|
| GB | 2042523 | 9/1980 |
| JP | 57-163369 | 10/1982 |
| WO | WO 94/08578 | 4/1994 |
| WO | WO 02/079167 | 10/2002 |
| WO | WO 03/066005 | 8/2003 |
| WO | WO 2005/063714 | 7/2005 |
| WO | WO 2005/095347 | 10/2005 |
| WO | WO 2006/098761 | 9/2006 |
| WO | WO 2007/001049 | 1/2007 |
| WO | WO2009/026548 | * 2/2009 |

OTHER PUBLICATIONS

Stanzione et al, "Drugs and Clinical Trials in Neurodegenerative Diseases", Ann Ist Super Sanita, 2011, vol. 47, No. 1, pp. 49-54.*
Secretary, Codex Alimentarius Commission. Codex alimentarius commission, World Health Organization, CL 2002/7-NFSDU, Mar. 2002, 8 pages.
Andrus et al., "Total Synthese of (+)-Geldanamycin and (-)-o-Quinogeldanamycin: Asymmetric Clycolate Aldol Reactions and Biological Evaluation," Journal of Organic Chemistry, 2003, vol. 68, pp. 8162-8169.
Ariese et al., "Comparison of Laurentian Fulvic Acid Luminescence with that of the Hydroquinone/quinone Model System: Evidence from low Temperature Fluorescence Studies and EPR Spectroscopy," Aquatic Sciences, 2004, vol. 66, pp. 86-94.
Berge et al., "Pharmaceutical Salts," Journal of Pharmaceutical Sciences, 1977, vol. 66(1), pp. 1-19.
Cysyk et al., "Reaction of Geldanamycin and C17-Substituted Analogues with Gluthathione: Product Indentifications and Pharmacological Implications", Chem Res. Toxicol., 2006, vol. 19, pp. 376-381.
Dehn et al., "Development of a new isogenic cell-xenograft system for evaluation of NAD(P)H:quinone oxidoreductase-directed antitumor quinones: evaluation of the activity of RH1.", Clin. Cancer Res., May 1, 2004, vol. 10, No. 9, pp. 3147-3155.
Guo et al., "Formation of 17-Allylamino-Demethoxygeldanamycin (17-AAG) Hydroquinone by NAD(P)H:Quinone Oxidoreducatase 1: Role of 17-AAG Hydroquinone in Heat Shock Protein 90 Inhibition," Cancer Res., 2005, vol. 65(21), pp. 10006-10015.

(Continued)

Primary Examiner — Layla Berry
(74) Attorney, Agent, or Firm — Sheridan Ross P.C.

(57) ABSTRACT

The invention provides 19-substituted geldanamycin derivatives, and pharmaceutically acceptable salts thereof that are potent Hsp90 binding agents useful for the treatment of, and/or the amelioration of symptoms of, cancer or neurodegenerative disorders.

9 Claims, 12 Drawing Sheets

(56) References Cited

OTHER PUBLICATIONS

Guo et al., "The Bioreduction of a Series of Benzoquinone Ansamycins by NAD(P)H:Quinone Oxidoreductase1 to More Potent Heat Shock Protein 90 Inhibitors, the Hydroquinone Ansamycins," Mol. Pharmacol., 2006, vol. 70(4), pp. 1194-1203.
Harford et al., "Amino Terminal Cu(II)- and Ni(II)-Binding (ATCUN) Motif of Proteins and Peptides: Metal Binding, DNA Cleavage, and Other Properties," Acc. Chem. Res., 1997, vol. 30, p. 123-130 (1st page in lieu of Abstract), 4 pages.
Hu et al., "Isolation and characterization of novel geldanamycin analogs", Journal of Antibiotics, 2004, vol. 57, No. 7, pp. 421-428.
Kelland et al., "DT-Diaphorase expression and tumor cell sensitivity to 17-allylamino, 17-demethoxygeldanamycin, an inhibitor of heat shock protein 90", Journal of the National Cancer Institute, Nov. 17, 1999, vol. 91, No. 22, pp. 1940-1949.
Lucken, "Ion-Association and Specific Solvation in the Electron Spin Resonance Spectra of Semiquinones," The Journal of the Chemical Society, 1964, pp. 4234-4240.
Miller et al., "Depletion of the erbB-2 Gene Product p185 by Benzoquinoid Ansamycins," Cancer Research, 1994, pp. 2724-2730.
Miyata, "Hsp90 inhibitor geldanamycin and its derivatives as novel cancer chemotherapeutic agents," Curr. Pharm. Des., 2005, vol. 11(9), pp. 1131-1138 (ABSTRACT), 2 pages.
Ross, "Quinone Reductases Multitasking in the Metabolic World," Drug Metabolism Reviews, 2004, 36 (3-4), 659-654.
Schnur et al., "Inhibition of the Oncogene Product p185 in Vitro and in Vivo by Geldanamycin and Dihydrogeldanamycin Derivatives," Journal of Medicinal Chemistry, 1995, 38, p. 3806-3812.
Sittler et al., "Geldanamycin activates a heat shock response and inhibits huntingtin aggregation in a cell culture model of Huntington's disease," Human Molecular Genetics, 2001, vol. 10(12), pp. 1307-1315.
Stanzione et al., "Drugs and clinical trials in neurodegenerative diseases," Ann 1st Super Sanita, 2011, vol. 47(1), pp. 49-54.
Stebbins et al., "Crystal Structure of an Hsp9O-Geldanamycin Complex: Targeting of a Protein Chaperone by an Antitumor Agent," Cell, 1997, vol. 89, pp. 239-250.
Tadtong et al., "Geldanamycin derivatives and neuroprotective effect on cultured P19-derived neurons," Bioorganic & Medicinal Chemistry Letters, vol. 17, No. 10, Apr. 27, 2007, pp. 2939-2943.
Tziveleka et al., "Antioxidant Potential of Natural and Synthesised Polyprenylated Hydroquinones", Bioorganic and Medical Chemistry, 2002, vol. 10, pp. 935-939.
Whitesell et al. "Inhibition of Heat Shock Protein HSP90-pp60 Heteroprotein Complex Formation by Benzoquinone Ansamycins: Essential Role for Stress Proteins in Oncogenic Transformation," Proceedings of the National Academy of Sciences, 1994, vol. 91, 8324-8328.
International Search Report for International (PCT) Patent Application No. PCT/US05/31524, mailed May 17, 2007, 3 pages.
Written Opinion for International (PCT) Patent Application No. PCT/US05/31524, mailed May 17, 2007, 5 pages.
International Preliminary Report on Patentability for International (PCT) Patent Application No. PCT/US2005/031524, mailed Sep. 20, 2007, 6 pages.
Extended European Search Report or Application No. EP 05810418.3, dated Feb. 16, 2009, 14 pages.
Communication from European Patent Office for European Patent Application No. 05810418.3, dated Feb. 11, 2010, 3 pages.
Official Action for European Patent Application No. 05810418.3, dated Apr. 14, 2011 4 pages.
Official Action for European Patent Application No. 05810418.3, dated Jul. 22, 2013 4 pages.
International Search Report for International (PCT) Patent Application No. PCT/US08/74077, mailed Nov. 19, 2008, 4 pages.
Written Opinion for International (PCT) Patent Application No. PCT/US08/74077, mailed Nov. 19, 2008, 5 pages.
International Preliminary Report on Patentability for International (PCT) Patent Application No. PCT/US2008/074077, mailed Mar. 4, 2010, 7 pages.
Search Report for European Patent Application No. 08798530.5, dated Mar. 22, 2011, 6 pages.
International Search Report and Written Opinion for International Patent Application No. PCT/US12/65111, mailed Mar. 25, 2013, 12 pages.
International Preliminary Report on Patentability for International Patent Application No. PCT/US12/65111, mailed May 30, 2014, 9 pages.
Official Action for U.S. Appl. No. 11/218,320, mailed Jul. 10, 2007, 12 pages.
Official Action for U.S. Appl. No. 11/218,320, mailed Apr. 17, 2008, 10 pages.
Official Action for U.S. Appl. No. 11/218,320, mailed Sep. 15, 2008, 7 pages.
Notice of Allowance for U.S. Appl. No. 11/218,320, mailed Jun. 25, 2009, 6 pages.
Official Action for U.S. Appl. No. 12/673,996, mailed Sep. 17, 2012, 15 pages.
Official Action for U.S. Appl. No. 12/673996, mailed Feb. 11, 2013, 11 pages.
Notice of Allowance for U.S. Appl. No. 12/673,996, mailed Jun. 7, 2013, 12 pages.

* cited by examiner

HSP90 INHIBITORS WITH MODIFIED TOXICITY

CROSS REFERENCE TO RELATED APPLICATION

This application is a national stage application under 35 U.S.C. 371 of PCT Application No. PCT/US2012/065111 having an international filing date of Nov. 14, 2012, which designated the United States, which PCT application claimed the benefit of U.S. Application Ser. No. 61/559,144, filed Nov. 14, 2011 and U.S. Application Ser. No. 61/702,222, filed Sep. 17, 2012, all of which are incorporated by reference in their entirety.

GOVERNMENT INTEREST

This invention was made with government support under grant number CA051210 awarded by the National Institutes of Health. The government has certain rights in the invention.

FIELD OF INVENTION

This invention relates to geldanamycin derivatives having preferable toxicity profiles and their use in the treatment and prevention of cancer and neurodegenerative disorders in a mammal, and pharmaceutical compositions containing these derivatives.

BACKGROUND OF INVENTION

Hsp90 is a protein chaperone that utilizes the hydrolysis of ATP to assist in the folding of early nascent forms of proteins to their mature, correctly-folded forms. Once the protein has been correctly folded, Hsp90 is released and thus, it functions as a true protein "catalyst." Hsp90 has also been recognized as an attractive anticancer target in that this chaperone assists in the folding of many oncogenic proteins including ErbB2, Raf-1, mutant p53, estrogen and steroid receptors. Thus, by inhibiting Hsp90, a large number of downstream oncogenic proteins can be disrupted, thereby attacking the neoplastic process at a number of points.

Neurodegenerative disorders including Parkinsons Disease (PD), Parkinsonian like syndromes such as Amyotrophic Lateral Sclerosis (ALS) and Progressive Supranuclear Palsy (PSP), Alzheimers Disease (AD) and poly Q disorders such as Huntington's disease, are characterized by the accumulation of misfolded proteins. Inhibition of Hsp90 results in a compensatory increase in other protein chaperones, which promote correct protein folding and thereby ameliorates diseases associated with accumulation of misfolded proteins.

The first Hsp90 inhibitor used clinically was geldanamycin. Geldanamycin is a benzoquinone ansamycin polyketide isolated from *Streptomyces geldanus*. Although originally discovered by screening microbial extracts for antibacterial and antiviral activity, geldanamycin was later found to be cytotoxic to tumor cells in vitro and to be neuroprotective to cultured neurons.

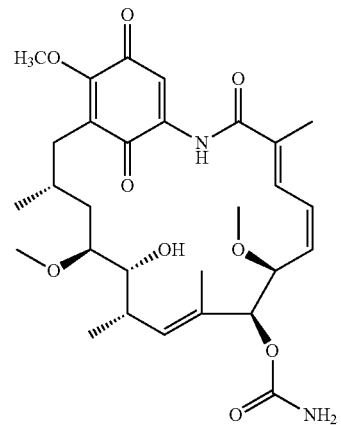

Geldanamycin

Unfortunately, the administration of geldanamycin produced unacceptable hepatotoxicity, which led to its withdrawal from Phase I clinical trials. The observed toxicity of these compounds is believed to be a result, at least in part, of glutathione depletion. Second generation geldanamycin derivatives were developed including 17-demethoxy-17-(2-propenylamino)-geldanamycin (17-AAG; also known as 17-allylaminogeldanamycin) and 17-demethoxy-17-[[2-(dimethylamino)ethyl]amino]-geldanamycin (17-DMAG). These molecules reduce liver toxicity and have shown success in Phase I and Phase II clinical trials.

While there has been a great deal of research interest in the benzoquinone ansamycins, particularly geldanamycin and 17-AAG, there remains a need for effective derivatives of these compounds having higher activity without the significant risk of toxicity of the parent geldanamycin compound.

SUMMARY OF INVENTION

The present invention provides novel geldanamycin derivatives (quinone and hydroquinone ansamycins) modified at the 19 position of the geldanamycin molecule, and pharmaceutically acceptable salts thereof, that are potent Hsp90 binding agents with improved toxicity profiles relative to the parent quinones and hydroquinones. The 19-substituted benzoquinone and hydroquinone ansamycins of the present invention do not deplete glutathione and are therefore less hepatotoxic.

The present invention also provides methods of making and using these novel compounds as well as pharmaceutical compositions containing these compounds.

One embodiment is a compound of the invention having the chemical structure of Formula I:

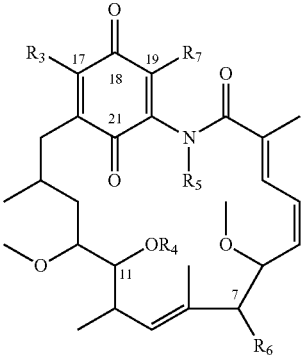

Formula I or a pharmaceutically-acceptable salt thereof;
wherein:
$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino) methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; wherein when $R_7$ is Br, $R_3$ is not $OCH_3$;

$R_4$ is H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_5$ H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is $SR_{12}$, CN, $CF_3$, $C_{1-6}$ alkyl, alkenyl, alkynyl, cycloalkenyl, substituted or unsubstituted aromatic, substituted or unsubstituted heterocyclic, substituted or unsubstituted heteroaromatic, wherein $R_{12}$ is $C_{1-6}$ alkyl, $C_{3-8}$ cycloalkyl, substituted or unsubstituted aromatic, substituted or unsubstituted heterocyclic, substituted or unsubstituted heteroaromatic.

A specific embodiment is a purified compound of the invention having the chemical structure of Formula I, wherein:

$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino) methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are H, $R_6$ is $OC(=O)NH_2$, and, $R_7$ is $CH_3$, $CF_3$, CN, $SR_{12}$ or phenyl.

Another embodiment of the invention is a compound of the invention having the chemical structure of Formula II:

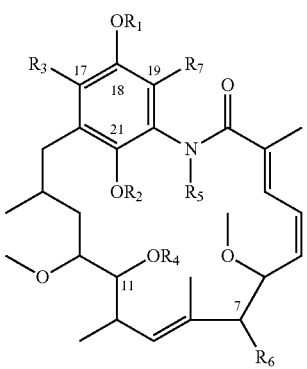

Formula II or a pharmaceutically-acceptable salt thereof; wherein:

$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, alkoxy, alkylthiol, glycoside, glucuronide or sulfate, $C(=O)CH(X)NH_2$, and $C(=O)CH(X)OH$, wherein X=an amino acid side chain;

$R_3$ is H, $NHCH_2CH=CH_2$, $NHCH_2CH_2N(CH_3)_2$, $NHCH_2CH_2NC_4H_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino) methyl-1-aziridinyl, 3-(dimethylamino)-1-azetidinyl, 3-hydroxy-1-pyrrolidinyl, 3,4-dihydroxy-1-pyrrolidinyl, or $NR_8R_9$, $OR_8$, $SR_8$, wherein $R_8$ and $R_9$ are independently H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl; wherein when $R_7$ is Br, $R_3$ is not $OCH_3$;

$R_4$ is H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_5$ is H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, OC(=O)NH$_2$, OC(=O)C$_{1-10}$ alkyl, OSO$_2$OH, OC(=O)OSO$_2$OH and OC(=O)NR$_{10}$R$_{11}$ wherein R$_{10}$ and R$_{11}$ are independently H and C$_{1-10}$ alkyl; and, $R_7$ is SR$_{12}$, CN, CF$_3$, C$_{1-6}$ alkyl, alkenyl, alkynyl, cycloalkenyl, substituted or unsubstituted aromatic, substituted or unsubstituted heterocyclic, substituted or unsubstituted heteroaromatic, wherein R$_{12}$ is C$_{1-6}$ alkyl, C$_{3-8}$ cycloalkyl, substituted or unsubstituted aromatic, substituted or unsubstituted heterocyclic, substituted or unsubstituted heteroaromatic.

A specific embodiment of the invention is a compound of the invention having the chemical structure of Formula II, wherein:

$R_3$ is H, NHCH$_2$CH=CH$_2$, NHCH$_2$CH$_2$N(CH$_3$)$_2$, NHCH$_2$CH$_2$NC$_4$H$_8$, alkoxy, azetidinyl, furfuryl, morpholinyl, piperazinyl, piperidinyl, piperazinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, or NR$_8$R$_9$, OR$_8$, SR$_8$, wherein R$_8$ and R$_9$ are independently H, C$_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-aziridinyl)alkyl, (1-aziridinylmethyl)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-pyrrolidinyl)alkyl, (1-ethyl-2-pyrrolidinyl)methyl, or 2-(N-methyl-pyrrolidin-2-yl)ethyl;

$R_4$ and $R_5$ are H, $R_6$ is OC(=O)NH$_2$, and, $R_7$ is CH$_3$, CF$_3$, CN, SR$_{12}$ or phenyl.

A related embodiment of this invention is a pharmaceutical composition containing a compound of the invention wherein the compound is present in the cis-confirmation or is present substantially in the cis-confirmation, and at least one pharmaceutical excipient.

An embodiment of this invention is a method of treating cancer or other proliferative diseases, or ameliorating the symptoms of these diseases, by administering a therapeutically effective amount of at least one compound of the invention, or a pharmaceutically acceptable salt form thereof, to a mammal in need of such treatment or suspected of having a cancer or other proliferative disease.

Another embodiment of this invention is a method of treating cancer or other proliferative diseases, or ameliorating a symptom thereof, by administering a therapeutically effective combination of one of the compounds of the present invention and one or more other known anti-cancer or anti-proliferative compounds. For example, the other anti-cancer compounds may include at least one of a tyrosine kinase inhibitor, paclitaxel and doxorubicin.

Another embodiment of this invention is a method of treating cancer or other proliferative diseases, or ameliorating a symptom thereof, by administering a therapeutically effective amount of one of the compounds of the present invention in conjunction with medically supervised radiation therapy, surgery, other forms of chemotherapy, radiation, immunotherapy, or combinations thereof.

In these embodiments of the invention, the cancer may be a cancer selected from breast, colon, epidermoid, prostate, pancreatic, leukemia, ovarian, small cell lung, cervical, neuroblastoma, endometrial, melanoma, renal and peritoneal cancers.

Another embodiment of the present invention is a method of inhibiting the Hsp90 activity in a cell by contacting the cell with one or more of the compounds of the present invention.

Another embodiment of the present invention is a method of disrupting the folding of a protein such as, but not limited to, ErbB2, Raf-1, mutant p53, estrogen and steroid receptors in a cell by contacting the cell with one or more of the compounds of the present invention.

Another embodiment of the invention is a method of treating or preventing a disease associated with aberrant protein folding in mammals, including for example, neurodegenerative disorders, or ameliorating a symptom thereof. Neurodegenerative diseases and syndromes (hereinafter referred to collectively as neurodegenerative disorders) include Parkinsons Disease (PD), Parkinsonian like syndromes (such as Amyotrophic Lateral Sclerosis (ALS) and Progressive Supranuclear Palsy (PSP), Alzheimers Disease (AD)) and poly Q disorders (such as Huntington's disease). These neurodegenerative disorders are characterized by the accumulation of misfolded proteins, diagnostic protein aggregates and inclusion body formation, which in turn leads to toxicity, loss of neurons and eventual loss of functional capacity. By increasing intracellular levels of multiple protein chaperones, the compounds of the present invention have the effect of ameliorating, inhibiting or preventing the symptoms of such protein folding diseases, including neurodegenerative syndromes. The administration of one or more of the compounds of the present invention to the mammal results in a compensatory induction of multiple Heat Shock Proteins including Hsp70 and Hsp27, and has the effect of preventing, inhibiting or ameliorating the symptoms of a protein folding disease including these neurodegenerative disorders.

In these embodiments of the invention, the neurodegenerative disorder may be a neurodegenerative disorder selected from familial ALS, neurodegeneration, spinal and bulbar muscular atrophy (SBMA), Huntington's disease, poly Q disease, Alzheimer's disease, and Parkinson's disease.

Another embodiment of the present invention is a method of increasing Raf-1 degradation in a cell by contacting the cell with one or more of the compounds of the present invention. Another embodiment of the present invention is a method of decreasing MEK and/or ERK phosphorylation in a cell by contacting the cell with one or more of the compounds of the present invention.

Another embodiment of this invention is a method of testing the susceptibility of a mammal to treatment with one of the compounds of the present invention by testing the mammal for the presence of a mutation in the NQO1 gene in the mammal wherein the presence of a mutation in the NQO1 gene is indicative of limited, or no susceptibility to response to a compound of the present invention by the mammal. In one embodiment, the mutation in the NQO1 gene is a "C" to "T" transversion at position 609 of NQO1, leading to a nonsynonymous amino acid change Pro187Ser, P187S).

Another embodiment of this invention is a method of testing the susceptibility of a mammal to treatment with one of the compounds of the present invention by testing the mammal for the presence NQO1 enzymatic activity in the mammal, wherein reduced or absent NQO1 enzymatic activity is indicative of limited or no susceptibility to response to a compound of the present invention by the mammal.

The invention also provides pharmaceutical compositions containing one or more of the compounds of the invention with at least one pharmaceutically-acceptable carrier. Thus, in one aspect of the invention, at least one compound of the invention is administered to a mammal in a pharmaceutical composition of the invention.

Also provided herein are methods for the prevention, treatment or prophylaxis of cancer in a mammal, comprising administering to the mammal in need thereof, therapeutically-effective amounts of any of the pharmaceutical compositions of the invention.

Also provided herein are packages containing a pharmaceutical composition comprising therapeutically-effective amounts of at least one compound of the invention, together with at least one pharmaceutically acceptable carrier. The pharmaceutical compositions may be administered separately, simultaneously or sequentially, with other compounds or therapies used in the prevention, treatment or amelioration of cancer. These packages may also include prescribing information and/or a container. If present, the prescribing information may describe the administration, and/or use of these pharmaceutical compositions alone or in combination with other therapies used in the prevention, treatment or amelioration of cancer.

Also provided herein are packages containing a pharmaceutical composition comprising therapeutically-effective amounts of at least one compound of the invention, together with at least one pharmaceutically acceptable carrier. The pharmaceutical compositions may be administered separately, simultaneously or sequentially, with other compounds or therapies used in the prevention, treatment or amelioration of neurodegenerative syndromes or disorders. These packages may also include prescribing information and/or a container. If present, the prescribing information may describe the administration, and/or use of these pharmaceutical compositions alone or in combination with other therapies used in the prevention, treatment or amelioration of neurodegenerative syndromes or disorders.

Additional embodiments of the present invention include the use of metal chelating agents to prevent or reduce the autoxidation of the hydroquinone ansamycin derivatives of the present invention to the corresponding quinone compounds during storage or administration. Additionally, the invention provides pharmaceutical compositions containing hydroquinone ansamycin derivatives and a metal chelating agent.

Other aspects of the invention will be set forth in the accompanying description of embodiments, which follows and will be apparent from the description or may be learnt by the practice of the invention. However, it should be understood that the following description of embodiments is given by way of illustration only since various changes and modifications within the spirit and scope of the invention will become apparent to those skilled in the art and are encompassed within the scope of this invention.

Figure 1:
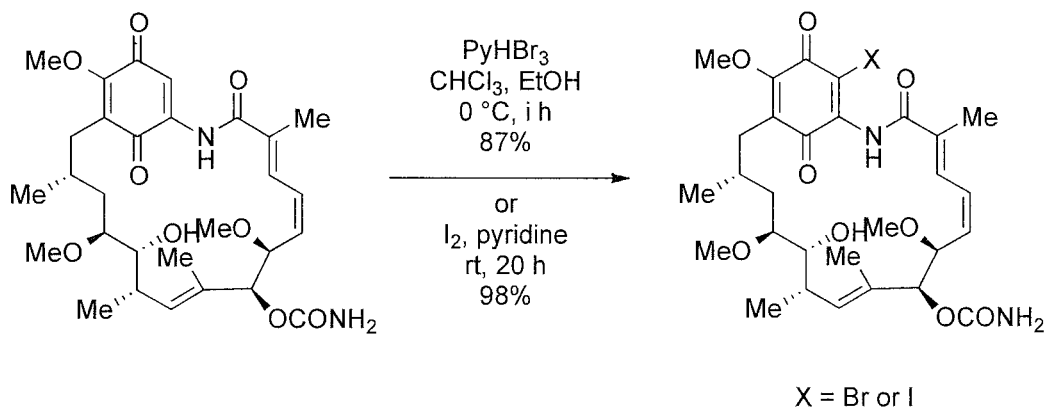
FIG. 1 shows the synthesis of 19-bromo- and 19-iodo-geldanamycin.
Figure 2:
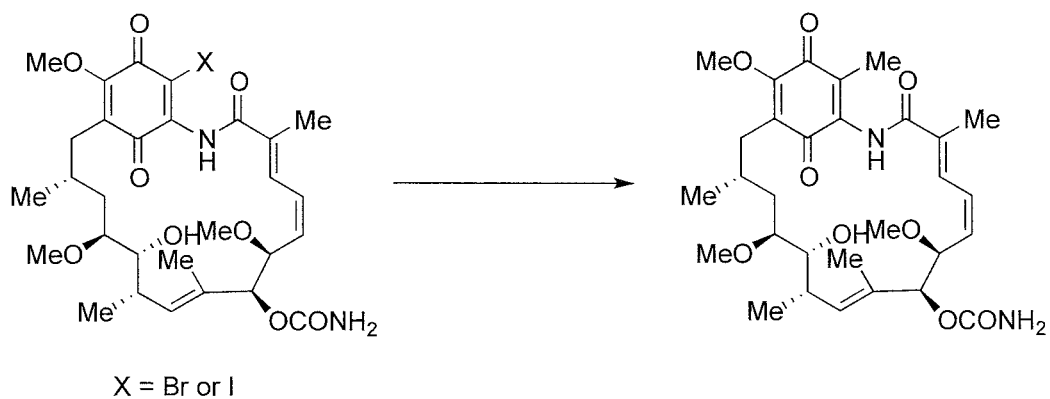
FIG. 2 shows a synthetic conversion of the 19-bromo or 19-iodo geldanamycin to the 19-methyl geldanamycin compound of the present invention.
Figure 3:
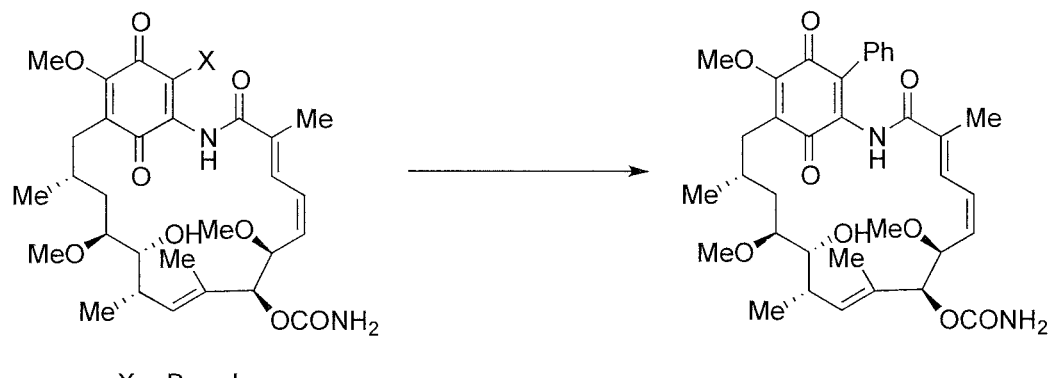
FIG. 3 shows a synthetic conversion of 19-bromo or 19-iodo geldanamycin to 19-phenyl geldanamycin.

The schemes of FIGS. 1-3 show the use of a geldanamycin starting material as an example, but one of skill in the art will readily recognize that these synthetic schemes are not limited to the geldanamycin molecule and may be generally applied to the use of benzoquinone ansamycin starting materials.

Figure 4:
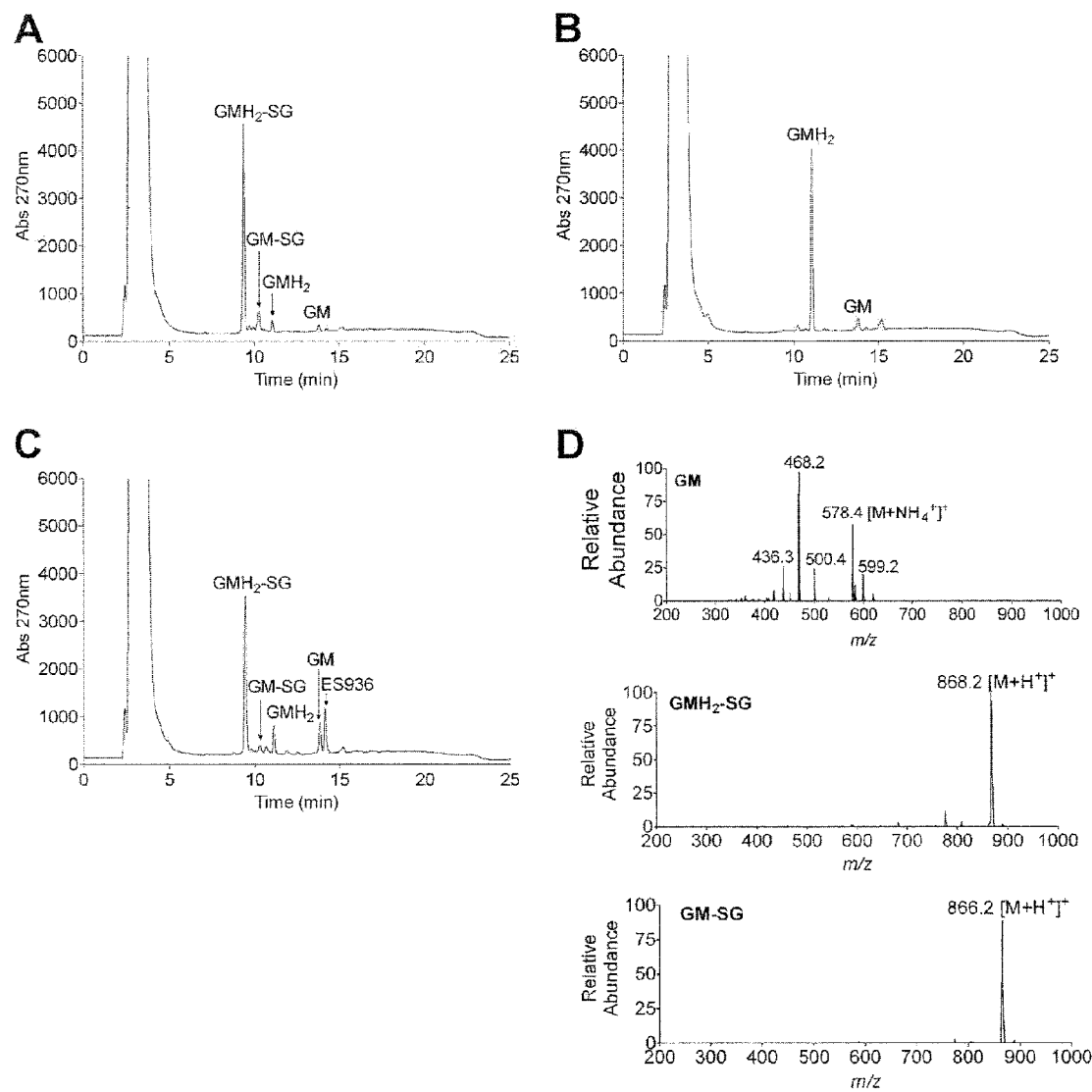

FIG. 4 shows HPLC and LC-MS analysis of the formation of GM-glutathione conjugates. GM-glutathione conjugate formation was analyzed by HPLC and LC-MS. Briefly, 50 µM GM, 500 µM NADH, and 5 mM glutathione in the absence and presence of 11.8 µg rh-NQO1 and in the absence or presence of 2 µM ES936, were incubated in 50 mM potassium phosphate buffer, pH 7.4 (1 ml) at room temperature for 5 min. GM-glutathione conjugate formation was analyzed by HPLC at 270 nm (5 min). A, GM and glutathione; B, GM, NADH, rhNQO1, and glutathione; C, GM, NADH, rhNQO1, ES936, and glutathione; D, LC-MS confirmed GMH2-SG and GM-SG as the product of the interaction of GM and glutathione.

Figure 5:
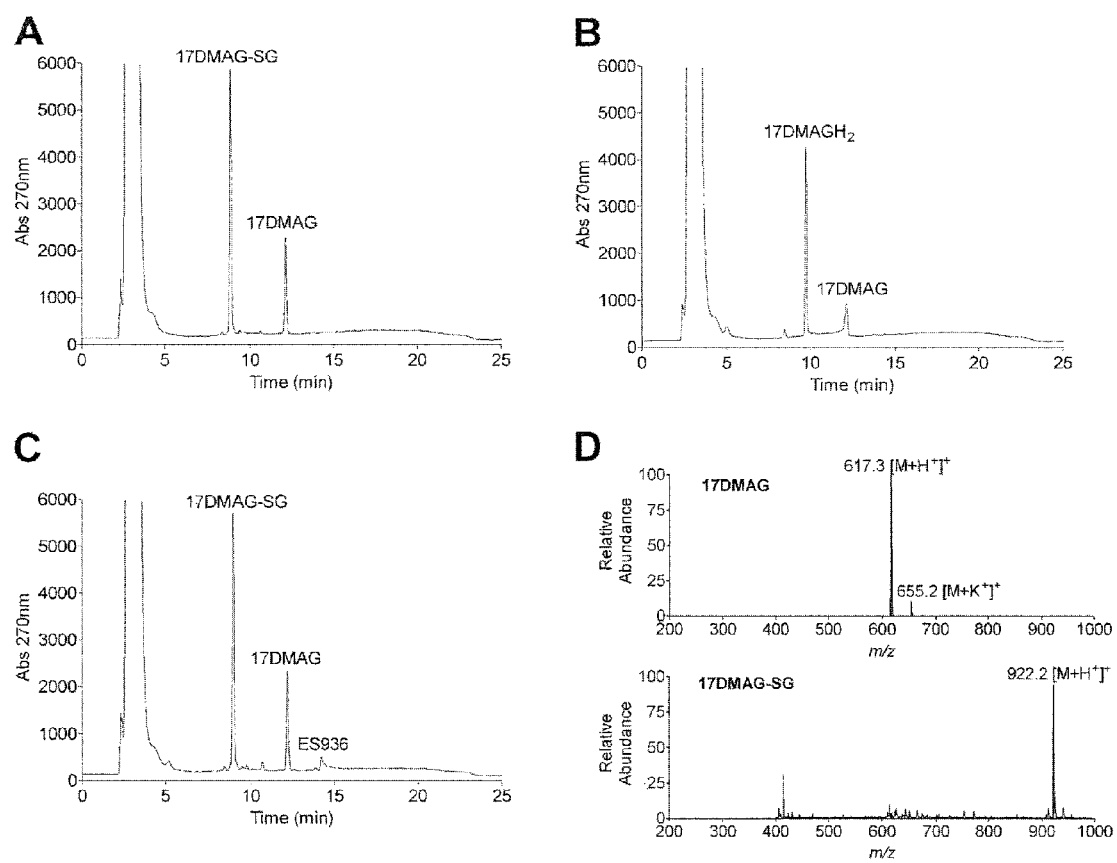

FIG. 5 shows HPLC and LC-MS analysis of the formation of 17-DMAG-glutathione conjugates. Reaction conditions were: 50 µM 17-DMAG, 500 µM NADH, and 5 mM glutathione, in the absence and presence of 11.8 µg rhNQO1 and in the absence or presence of 2 µM ES936, were incubated in 50 mM potassium phosphate buffer, pH 7.4 (1 ml) at room temperature for 3 h. 17-DMAG-glutathione conjugate formation was analyzed by HPLC at 270 nm (3 h). A, 17-DMAG and glutathione; B, 17-DMAG, NADH, rhNQO1, and glutathione; C, 17-DMAG, NADH, rhNQO1, ES936, and glutathione; D, LC-MS confirmed 17-DMAG-SG as the product of the interaction of 17-DMAG and glutathione.

Figure 6:
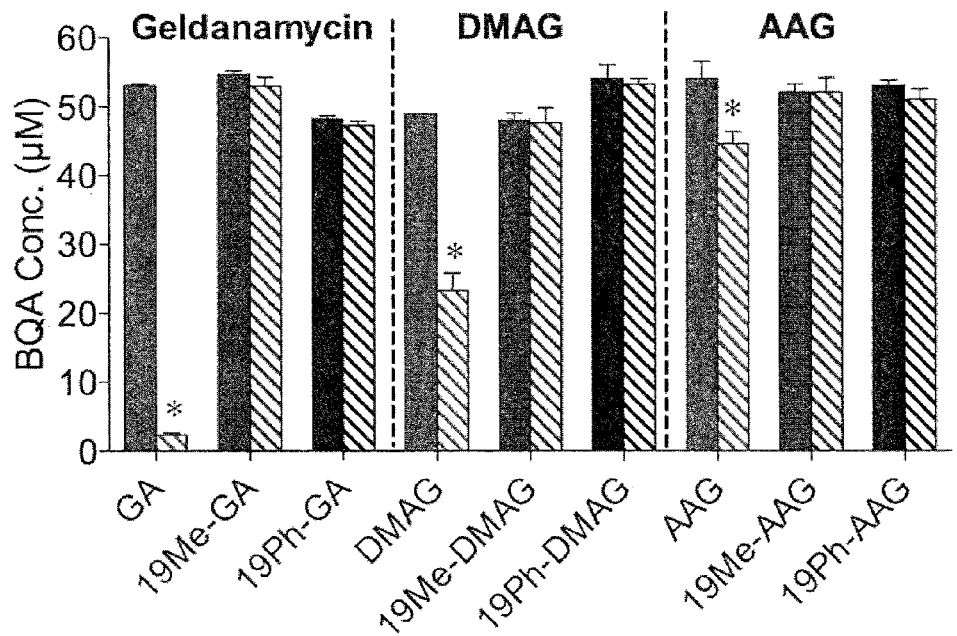

FIG. 6 shows in vivo testing of 19-substituted benzoquinone ansamycins conjugation to GSH. Benzoquinone ansamycins were tested in the absence (solid bars) and presence (hatched bars) of GSH.

Figure 7:
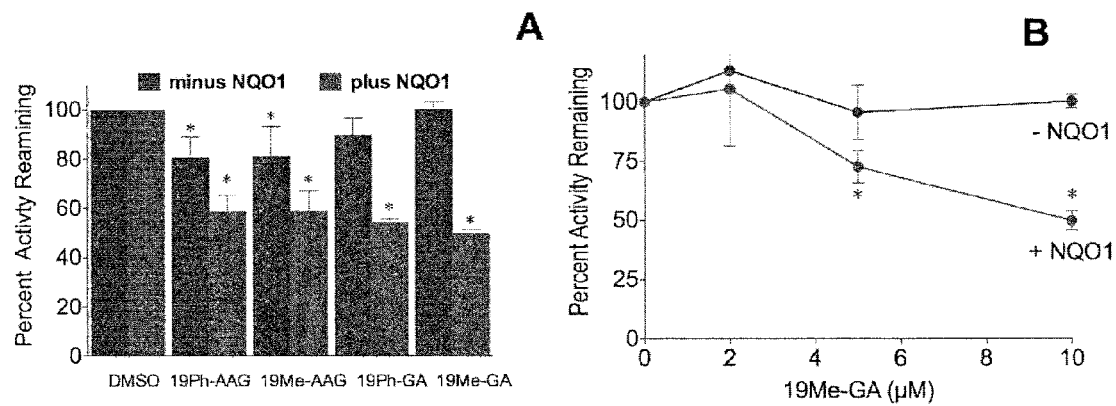

FIG. 7 shows in vivo testing of 19-substituted benzoquinone ansamycins inhibition of Hsp90. Purified recombinant yeast Hsp90 ATPase activity was measured in reactions with 19-substituted benzoquinone ansamycins (BQAs) in the absence and presence of NADPH quinone oxidoreductase 1 (NQO1).

Figure 8:
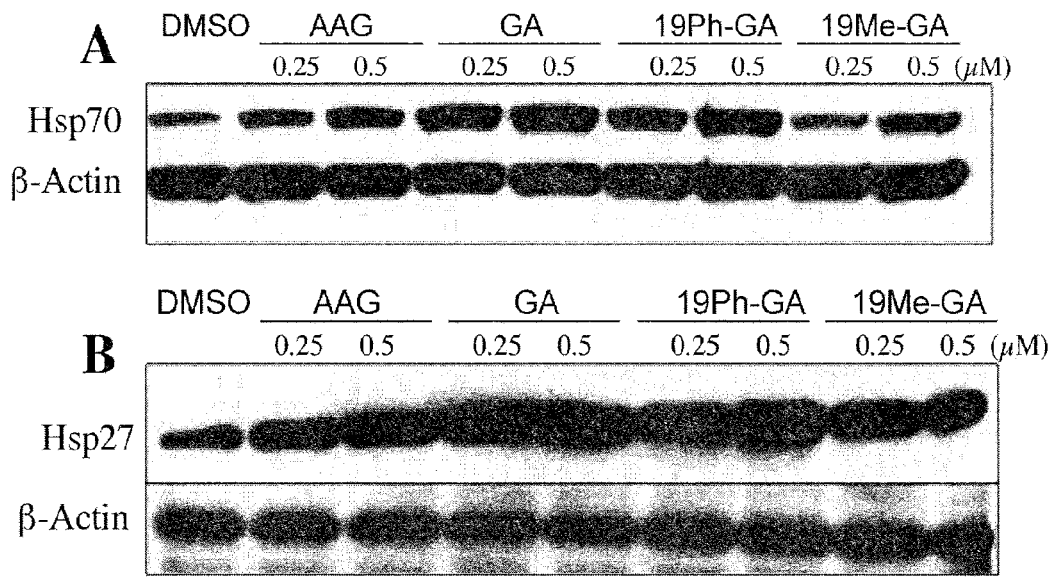

FIG. 8 shows the in vitro testing of 19-substituted benzoquinone ansamycins for their ability to induce Hsp70 and Hsp27. Hsp70 and Hsp27 protein levels were measured in SH-SY5Y cells by immunoblot analysis following treatment with BQAs for 16 hr.

Figure 9:
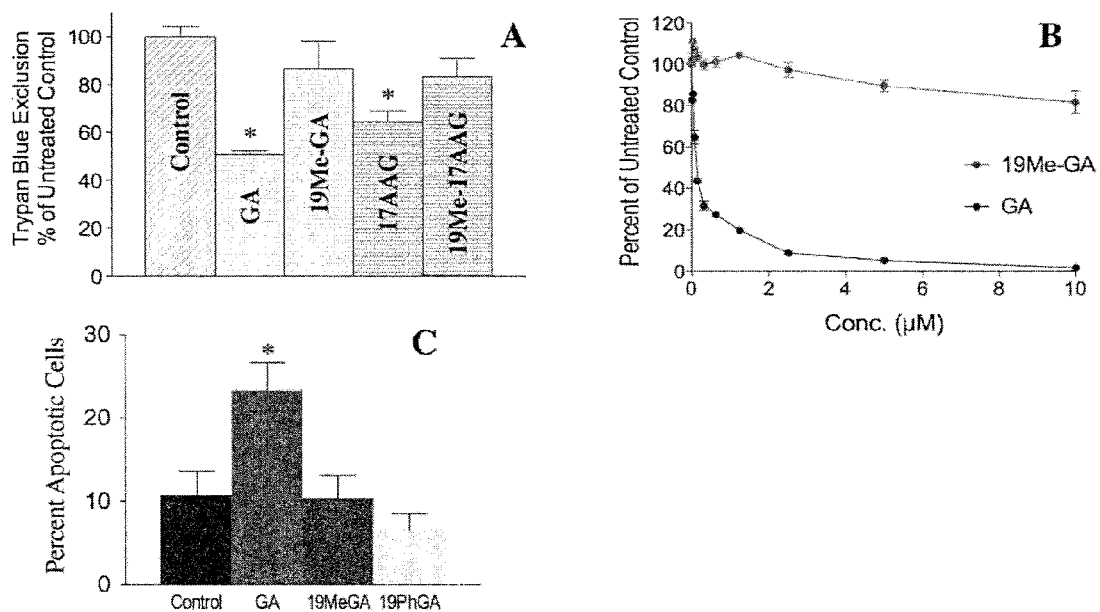

FIG. 9 shows the in vitro testing of 19-substituted benzoquinone ansamycins for their ability to reduce the toxicity of BAQs to SH-SY5Y cells. The toxicity of BQAs in SH-SY-5Y cells was measured using trypan blue exclusion, MTT growth inhibition assay and annexin V/PI staining for apoptosis.

Figure 10:
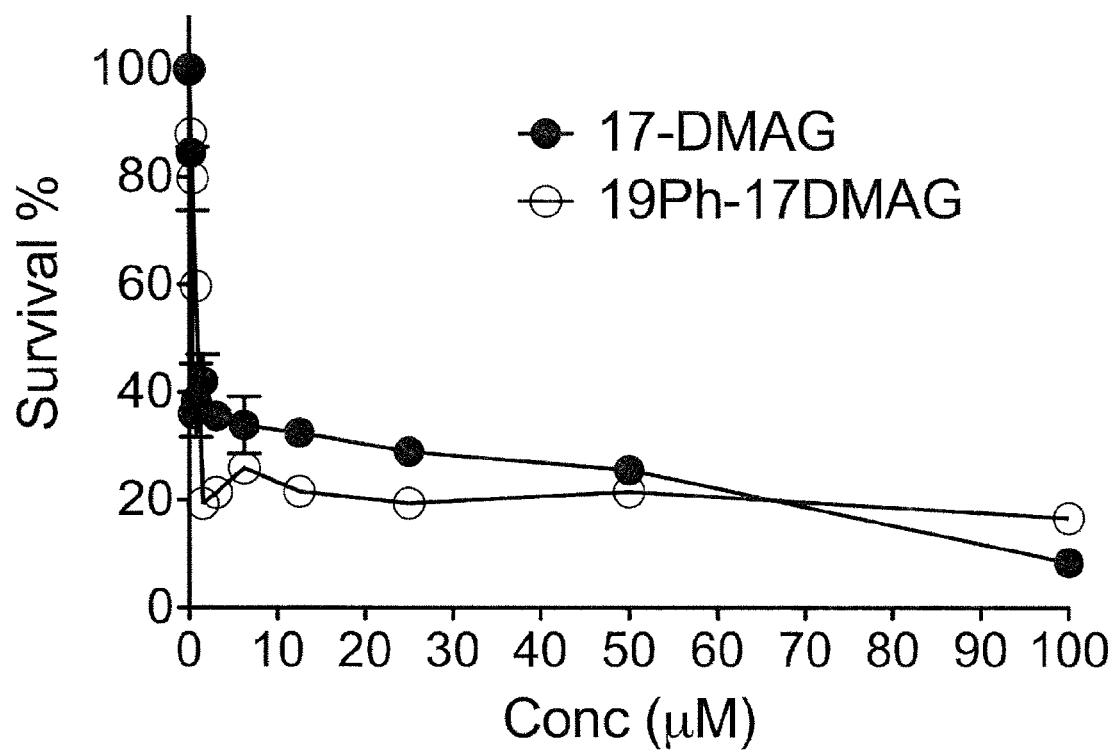

FIG. 10 shows the in vitro testing of 19-substituted DMAG analogs for their ability to inhibit growth of human breast cancer cells. MDA468/NQ16 breast cancer cell viability was measured using the MTT assay after treatment with 19-substituted DMAG analogs.

Figure 11:
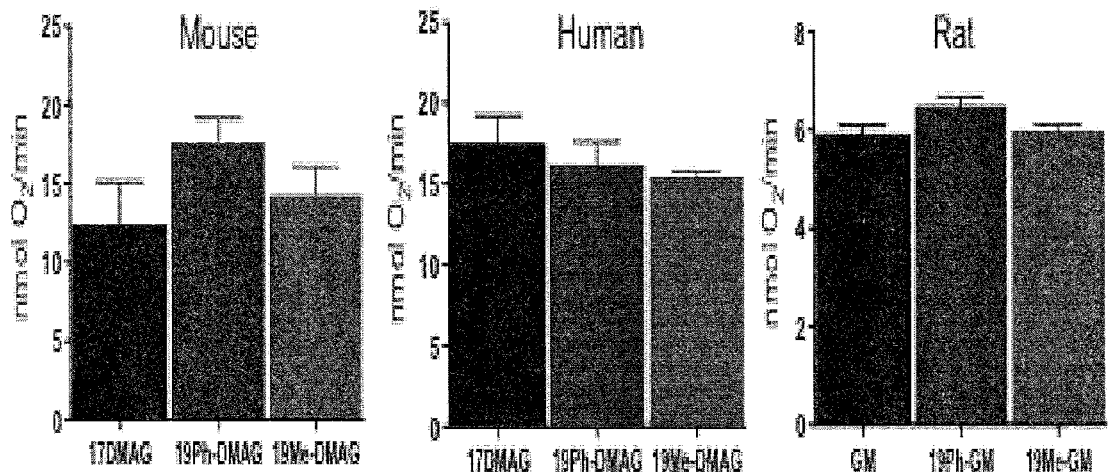

FIG. 11 shows the results of testing certain 19-substituted BQAs of the invention for the induction of redox cycling in hepatic microsomes.

Figure 12:
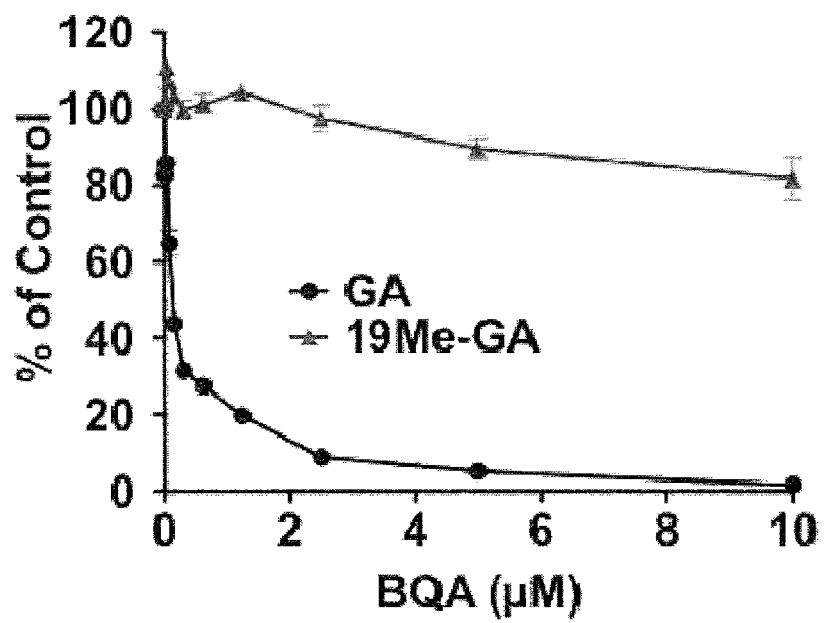

FIG. 12 shows the results of testing certain 19-substituted BQAs of the invention for toxicity in human dopaminergic cells.

Figure 13:
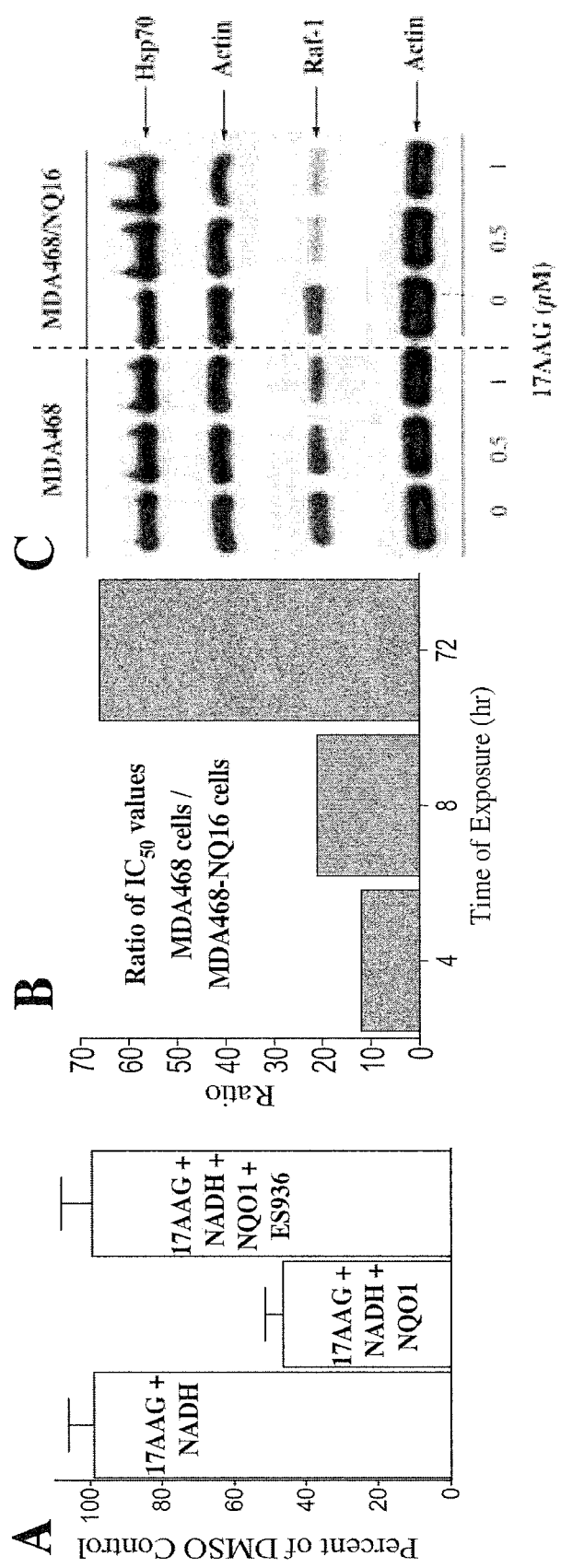

FIG. 13 shows data exemplifying the role of the hydroquinone in 17AAG-induced Hsp90 and growth inhibition.

Figure 14:
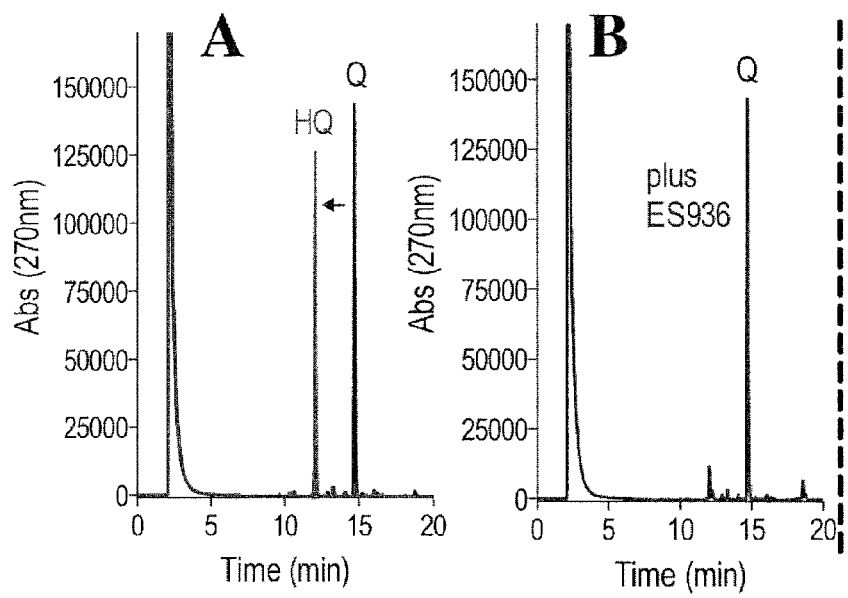

FIG. 14 shows the reduction of 19Ph-GA to 19Ph-GA hydroquinone by purified recombinant human NQO1, and in cells.

Figure 15:
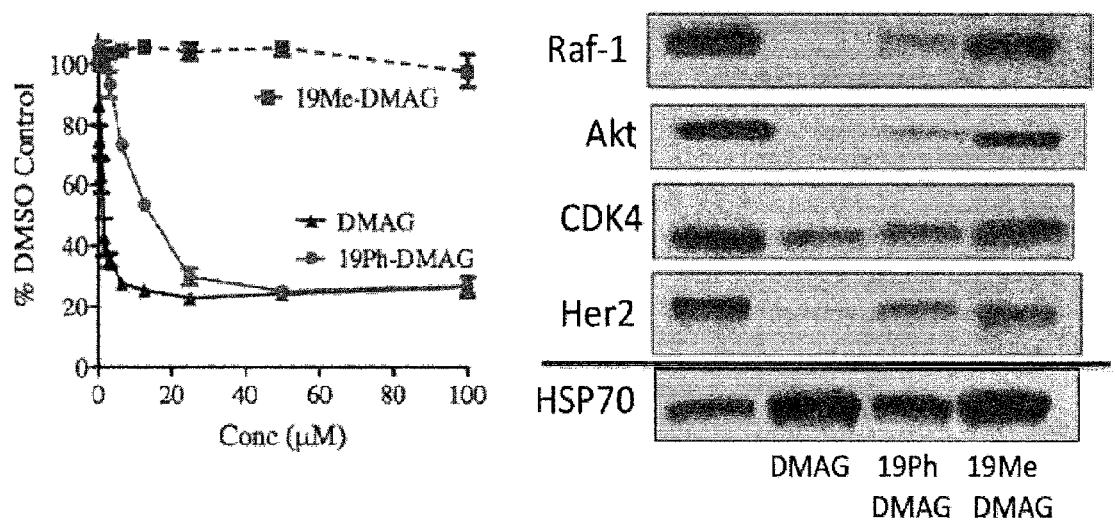

FIG. 15 shows the effect of 19-substituted DMAG analogs of the present invention on growth inhibition and biomarker of Hsp90 inhibition of BT474 human breast cancer cells.

Figure 16:
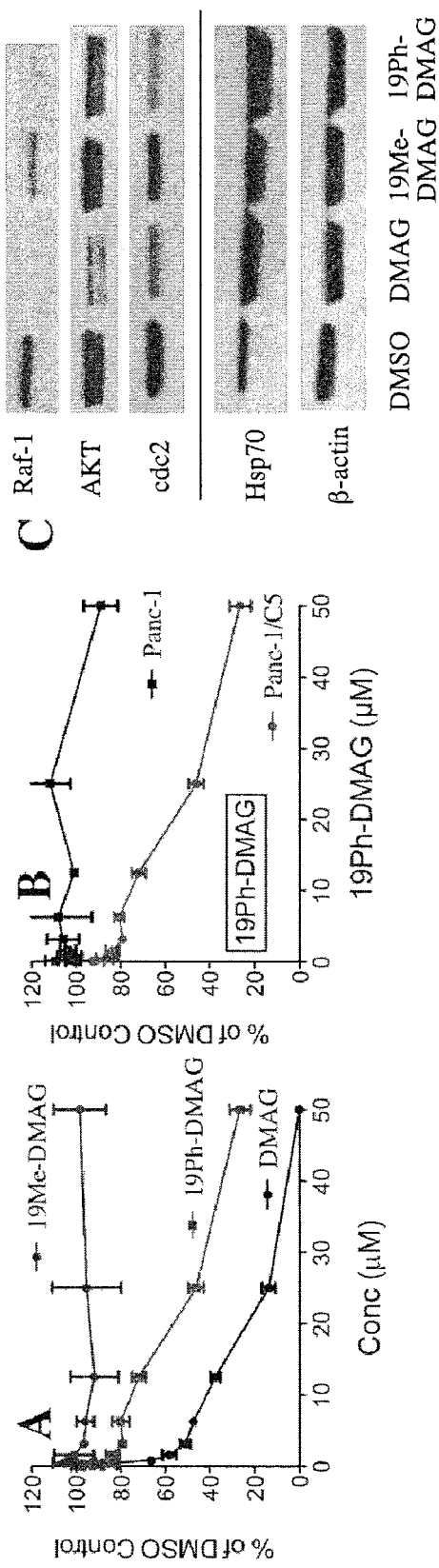

FIG. 16 shows the effect of 19-substituted DMAG analogs of the present invention on growth inhibition and biomarker of Hsp90 inhibition of MiaPaCa2 human pancreatic cancer cells.

Figure 17:
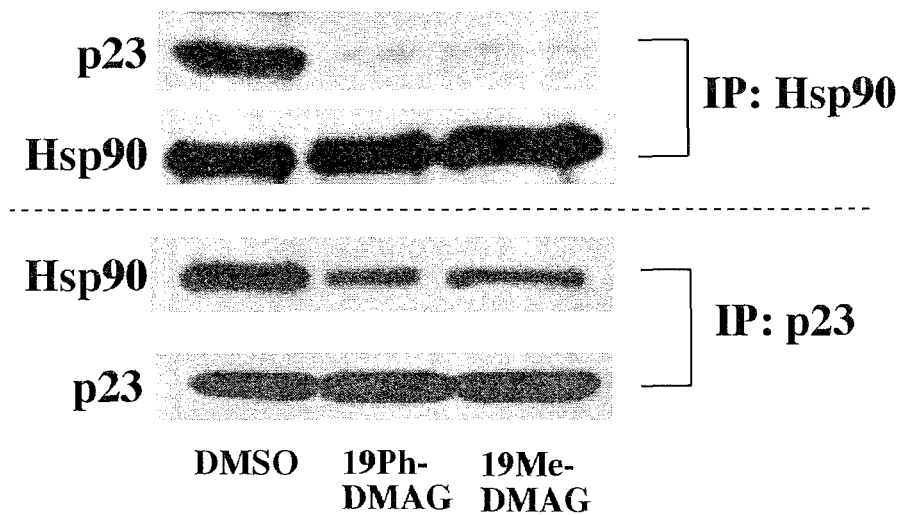

FIG. 17 shows that 19-phenyl and 19-methyl DMAG analogs of the present invention disrupt the binding of co-chaperone p23 to Hsp90.

Figure 18:
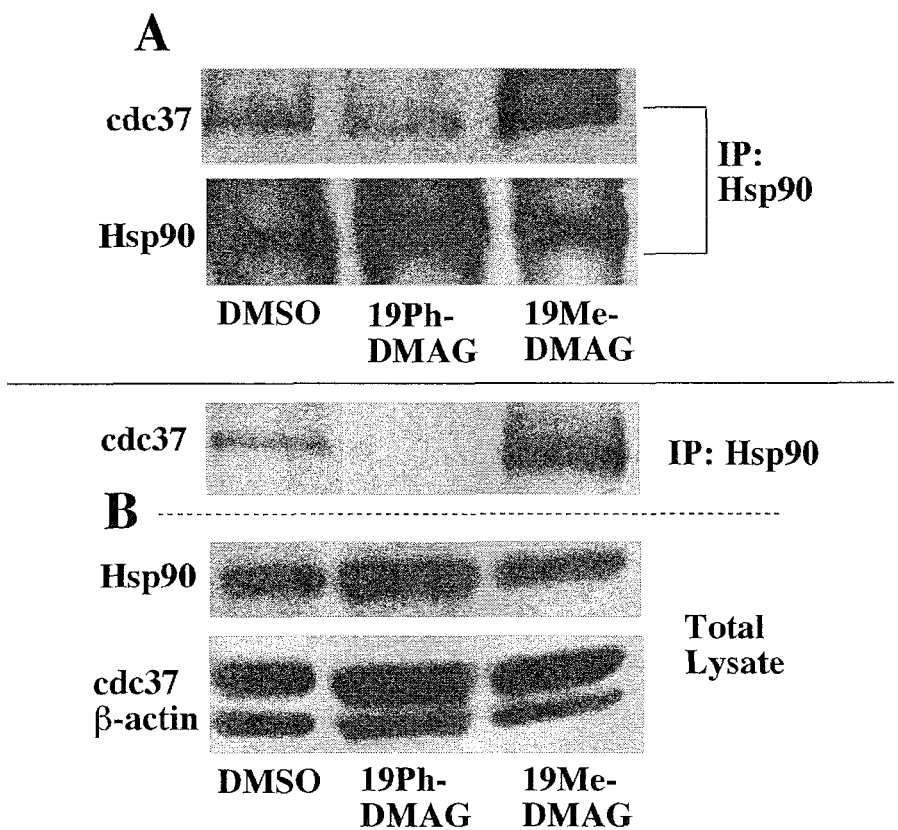

FIG. 18 shows that only 19Ph-DMAG will disrupt binding of co-chaperone cdc37 to Hsp90.

Figure 19:
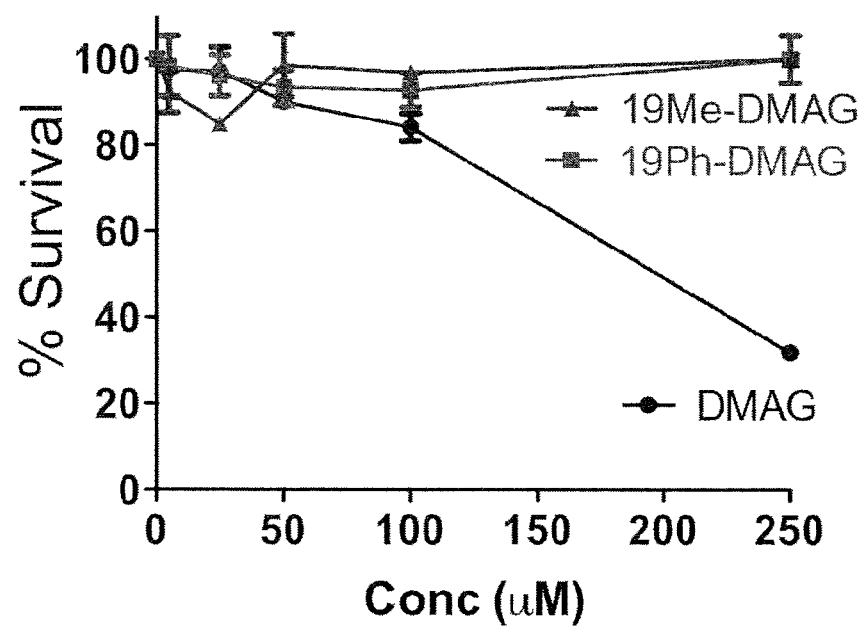

FIG. 19 shows that substitutions on the 19 position of DMAG prevent hepatotoxicity.

DESCRIPTION OF EMBODIMENTS

The present invention is drawn to methods of treating cancer or other proliferative diseases or neurodegenerative syndromes or disorders in a mammal by the administration of a therapeutically-effective amount of 19-substituted geldanamycin derivatives, or pharmaceutically-acceptable salts thereof, to the mammal. These 19-substituted geldanamycin derivatives exhibit significantly less hepatotoxicity than geldanamycin as they do not deplete glutathione. Additionally, the invention provides novel 19-substituted geldanamycin derivatives, pharmaceutically-acceptable salts thereof for use in pharmaceutical compositions to be administered to a mammal.

Hsp90 Inhibitors as Anticancer Agents.

Hsp90 has been developed as a potential anticancer target. Hsp90 is a protein chaperone which utilizes its ATPase activity to assist in the folding of early nascent forms of client proteins to their mature, correctly-folded forms. The basis for the use of Hsp90 as an anticancer target is that although it assists in the folding of many proteins, a high proportion of these have been identified as oncogenic proteins which can drive neoplasia. Thus, by targeting Hsp90, one can target a large number of downstream proteins and inhibit the neoplastic process at a number of points and such a combinatorial blockade of oncogenic targets gives rise to broad spectrum antitumor activity across multiple cancers. The first Hsp90 inhibitor used clinically was geldanamycin (GA) which did not move forward due to liver toxicity. The second generation BQAs 17-AAG and 17-DMAG are currently in Phase 1/2 clinical trials but their use is still limited by hepatotoxicity.

Hsp90 Inhibitors in Cancer and Neurodegenerative Disease.

Hsp90 is a protein chaperone which assists in protein folding and paradoxically it's inhibition has attracted considerable attention as a means of protecting against misfolded proteins. Hsp90 inhibition leads to activation of Heat Shock Factor 1 (Hsf-1) which is a master regulator of multiple heat shock proteins. Hsp90 and other co-chaperones maintain Hsf-1 in the cytosol in an inactive form but when Hsp90 is inhibited, Hsf-1 is released and migrates to the nucleus where it activates transcription of a network of Hsp's including Hsp70, 40 and 27 which are particularly active in protein folding. The compensatory induction of Hsps to a high level results in an increased total chaperone capacity of the cell and protection against diseases caused by misfolded proteins. This compensatory induction of other Hsp's is employed as a biomarker along with decreased Hsp90 client protein levels in studies of the anticancer activity of Hsp90 inhibitors in cancer patients.

The use of Hsp90 inhibitors as protective agents against neurodegenerative disease is a relatively new concept and the benzoquinone ansamycin (BQA) Hsp90 inhibitors have been used in a number of animal models of neurodegenerative disease. Geldanamycin, 17-AAG or 17-DMAG induce multiple Hsp's and protect against protein aggregation and toxicity in cell or animal models of multiple neurodegenerative diseases thereby demonstrating significant blood brain barrier penetration and therapeutic potential. These include protection against the toxicity of mutant forms of Cu/Zn SOD which occurs in about 20% of cases of familial ALS, increased Hsp activity in the spinal cord and protection against neurodegeneration in mouse models of spinal and bulbar muscular atrophy (SBMA), protection against htt aggregation and toxicity in a mouse model of Huntington's disease, protection against poly Q disease induced neurodegeneration and Tau aggregation in models of Alzheimer's disease. This is an impressive list and specifically with respect to Parkinson's disease, geldanamycin or 17-AAG have been shown to prevent α-synuclein aggregation and toxicity in a cellular model, protect against α-synuclein toxicity in fly and yeast models and protect against MPTP induced dopaminergic toxicity in a mouse model of PD.

Toxicity of Known Hsp90 Inhibitors Limits their Use.

Despite their clinical use, hepatotoxicity remains an issue with both 17-AAG and 17-DMAG. Hepatotoxicity was found to be a dose-limiting toxicity of 17-AAG in two separate phase 1 trials and in the most recent phase II trial of 17-AAG in advanced unresectable breast cancer, five patients developed grade 3/4 toxicities which were primarily hepatic and pulmonary. Based on these toxicity findings and lack of efficacy, 17-AAG was not recommended for further study for this indication. 17-DMAG also demonstrated significant toxicities in phase 1 clinical trials including hepatotoxicity as reflected by liver function changes. BQAs have also been found to be relatively toxic in mouse models of neurodegenerative disease. In a mouse motor neuron primary culture model BQAs induced marked increases in Hsp levels and conferred dramatic protection against mutant SOD proteins, but were found to be too toxic to cells. Similar toxic effects were observed using non-quinone Hsp90 inhibitors radicicol or pyrrolidine dithiocarbamate with induction of Hsp's only being observed at toxic concentrations. Newer Hsp90 inhibitors typically represented by non-quinone resorcinol scaffolds have also been found to have their own characteristic toxicities in animal models which limit their use. Thus, Hsp90 inhibitors represent an exciting opportunity for induction of Hsps in diseases characterized by protein misfolding, but the therapeutic window of the known Hsp90 inhibitors is too narrow, and less toxic agents are needed for clinical efficacy. This is particularly relevant if the Hsp90 inhibitors are employed as neuroprotective, where any effective drugs may need to be administered for long periods.

Mechanisms underlying the toxicity of quinones are a function of their ability to redox cycle and/or arylate cellular nucleophiles and the clinically used benzoquinone ansamycins are no exception. These molecules are capable of reaction with thiols at the 19-substituent leading to the formation of glutathione conjugates and adducts with cellular proteins. In our work we demonstrated that the parent BQA's GM, 17-AAG and 17-DMAG all interacted with glutathione to form adducts which were characterized by LC-MS. Once the protective capacity of cellular glutathione has been exceeded, conjugation of quinone electrophiles proceeds with protein based thiols leading to loss of protein structure and function and eventually to cellular toxicity. Glutathione conjugation also leads to loss of the Hsp90 inhibitory capacity of the BQA since the glutathione adduct cannot be accommodated in the active site of the Hsp90 ATPase precluding inhibition.

The Design of Less Toxic BQA Hsp90 Inhibitors: 19-Substituted Derivatives (19BQAs).

To design less toxic BQA Hsp90 inhibitors the inventors proceeded to block the thiol conjugation by synthesizing 19-substituted derivatives (19-BQAs). The inventors have shown previously that the BQAs in general have relatively low rates of redox cycling and have now compared the relative rates of redox cycling of 19-BQAs with their parent quinones (see Example 6 of this disclosure). No significant differences in redox cycling rates between all BQAs were found, whether they were 19-substituted or unsubstituted. Similar data was obtained using NADH-dependent redox cycling. Thus, the fact that 19-substitution precludes arylation, but does not alter the ability of BQAs to redox cycle, and still prevents hepatotoxicity, indicates that arylation reactions are predominantly responsible for the hepatotoxicity of BQAs. Thus, the compounds of the invention, especially the hydroquinone derivatives of 19BQAs, remain potent inhibitors of Hsp90, induce a robust protective Hsp response in cells, while showing greatly reduced and even minimal toxicity (see Example 6).

Mechanisms of Hsp90 Inhibition Induced by the Benzoquinone Ansamycin Class of Hsp90 Inhibitors.

As described above, the present inventors analyzed both mechanisms of Hsp90 inhibition and mechanisms of toxicity induced by BQA Hsp90 inhibitors, and demonstrated that hydroquinone ansamycins, rather than their parent BQAs were the active Hsp90 inhibitors. This important observation allowed the design of the compounds of the present invention, which are more effective Hsp90 inhibitors that can be activated by the high levels of NQO1 present in human tumors.

As noted above and demonstrated in Example 7 of this disclosure, the mechanism of inhibition of Hsp90 involves a trans-cis conversion of the BQA. The 19-substituted forms of the BQAs of the present invention already exist in their cis form and are therefore in the correct conformation for Hsp90 inhibition.

19-Phenyl BQAs have markedly different growth inhibitory effects relative to 19-Me-BQAs, which allowed the use of 19-phenyl and 19-methyl BQAs as tools to probe the mechanisms of inhibition of Hsp90 critical for growth inhibition.

The inventors next addressed the issue of whether the hydroquinone ansamycin played any functional role in Hsp90 inhibition and growth inhibitory activity induced by BQAs, and found that parent BQA's:

i) inhibited purified Hsp90 much more readily in the presence of NQO1 to generate the hydroquinone and this could be blocked by the inhibitor ES936;

ii) that isogenic NQO1-rich breast cancer cells (MDA468-NQ16) formed elevated levels of the hydroquinone metabolites and exhibited much greater Hsp90 and growth inhibitory effects (up to 66 fold depending on time of exposure) relative to their isogenic NQO1-null MDA468 paired cell line;

iii) that BQA-induced hydroquinone generation, Hsp90 and growth inhibitory effects could all be prevented by use of suicide inhibitors of NQO1; and, iv) molecular modeling of either benzoquinone or hydroquinone ansamycins in the active ATPase site of Hsp90 demonstrated a much more favorable binding energy for the hydroquinone form, as the free OH groups of the hydroquinone forms were important to the efficient binding of the molecule and formed H-bonds in the ATPase active site of Hsp90.

These data demonstrated that the hydroquinone ansamycins are more potent Hsp90 inhibitors than their parent quinones.

The BQA macrocycles are known to adopt an extended trans-amide conformation in the solid state as evidenced by X-ray crystal structure of geldanamycin. In contrast, protein crystallography studies using either yeast or human Hsp90 have shown that on binding, geldanamycin and 17-DMAG adopt a more closed "C-clamp" conformation with a cis-amide bond. 19-substituents on the geldanamycin quinone were designed to block attack by biological nucleophiles and hence ameliorate the hepatotoxicity seen with BQAs. However, the inventors also hypothesized that the 19-substituent might also increase the preference for the adoption of the cis-amide, and, consequently, affect the Hsp90 binding affinity and potency of the inhibitors.

Given the limited applicability of literature methods, particularly for the formation of a C—C bond at the 19-position, the inventors investigated a palladium-catalyzed cross-coupling strategy on readily available 19-iodogeldanamycin. After very considerable experimentation, it was found that the Stille reaction was most reliable, providing asynthetic route to the desired 19BQAs. NMR experiments using a range of techniques confirmed that the compounds had undergone the desired conformation change and were in the cis amide conformation in solution. X-ray crystallography also showed that the 19-(2-furyl) derivative exhibited both the cis-configured amide and also the 'C-clamp' conformation, in contrast to GA itself that adopt a trans-amide conformation in the crystal. Study of the binding of novel 19BQAs to the N-terminal ATPase domain of Hsp90 showed that the compounds bind with the cis amide conformation. These data demonstrate that the 19BQAs start out in the cis-amide conformation in both solution and solid states, and end up protein bound as cis.

Cellular Studies with 19-Substituted BQAs.

Studies conducted in cell lines (see Example 7) demonstrated that compounds of the invention induce growth inhibition in cancer cells, and the data indicate a role for NQO1 in the cytotoxicity of these compounds. Additionally, the 19-substituted compounds induced more pronounced Raf-1 and AKT degradation and equal Hsp70 induction compared to the parent compounds lacking 19-substitution.

The inventors also examined the hepatotoxicity of the 19-substituted compounds of the invention compared with the corresponding parent compounds lacking 19-substituents and demonstrated that the 19-substitutions clearly prevented toxicity in hepatocytes.

The term "alkyl" as used herein is directed to a saturated hydrocarbon group (designated by the formula $C_nH_{2n+1}$) which is straight-chained, branched or cyclized ("cycloalkyl") and which is unsubstituted or substituted, i.e., has had one or more of its hydrogens replaced by another atom or molecule.

"Aryl" designates either the 6-carbon benzene ring or the condensed 6-carbon rings of other aromatic derivatives (see, e.g., Hawley's Condensed Chemical Dictionary (13 ed.), R. J. Lewis, ed., J. Wiley & Sons, Inc., New York (1997)). Aryl groups include, without limitation, phenyl, naphthyl, indanyl and indenyl. "Substituted aryl" means that one or more hydrogen atoms on the designated aryl substituent is replaced with a selection from the indicated group, provided that the designated atom's normal valency is not exceeded, and that the substitution results in a stable compound. Exemplary aryl substituents include, but are not limited to, hydroxy, mercapto, amino and substituted amino, nitro, carboxylic acid, amide or ester derivatives, sulfonic acid, halide, trihalomethyl, $C_{1-6}$ alkyl, $C_{1-6}$ alkenyl, $C_{1-4}$ alkoxy, and $C_{3-8}$ cycloalkyl.

The term "heteroaryl" refers to monocyclic or polycyclic groups having at least one aromatic ring structure and including one or more heteroatoms and preferably one to fourteen carbon atoms. Illustrative examples of heteroaryl groups include, but are not limited to, furanyl, imidazolyl, indanyl, indolyl, indazolyl, isoxazolyl, isoquinolyl, oxazolyl, oxadiazolyl, pyrazinyl, pyridyl, pyrimidinyl, pyrrolyl, pyrazolyl, quinolyl, quinoxalyl, tetrazolyl, thiazolyl, thienyl, and the like.

The term "heterocycle" or "heterocyclic" or "heterocyclic moiety" refers to ring-containing monovalent and divalent radicals having one or more heteroatoms, independently selected from N, O and S, as part of the ring structure and comprising at least 3 and up to about 20 atoms in the rings preferably 5- and 6-membered rings. Heterocyclic moieties may be saturated or unsaturated, containing one or more double bonds, and heterocyclic moieties may contain more than one ring. Heterocyclic moieties include for example monocyclic moieties such as: aziridine, oxirane, thiirane, azetidine, oxetane, thietane, pyrrolidine, pyrroline, imidazolidine, pyrazolidine, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. In addition heterocyclic moieties include heteroaryl rings such as: pyridyl, pyrazinyl, pyrimidinyl, pyridazinyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl. Additionally, heterocyclic moieties encompass polycyclic moieties such as: indole, indoline, quinoline, tetrahydroquino line, isoquino line, tetrahydroisoquino line, 1,4-benzodioxan, coumarin, dihydrocoumarin, benzofuran, 2,3-dihydrobenzofuran, 1,2-benzisoxazole, benzothiophene, benzoxazole, benzothiazole, benzimidazole, benzotriazole, thioxanthine, carbazole, carboline, acridine, pyrolizidine, and quinolizidine.

"Alkenyl" as used herein by itself or as part of another group refers to straight or branched chain substituent of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like, which may be substituted in the same manner as that described for alkyl groups.

The term "cycloalkyl" as employed herein alone or as part of another group includes saturated cyclic hydrocarbon groups or partially unsaturated (containing 1 or 2 double bonds) cyclic hydrocarbon groups, containing one ring and a total of 3 to 7 carbons, preferably 3 to 6 carbons, forming the ring, which includes cyclopropyl, cyclobutyl, cyclopentyl, cyclohexyl, cycloheptyl, cyclopentenyl and cyclohexenyl, which may be substituted in the same manner as that described for alkyl groups.

"Cycloalkenyl" means $C_{3-8}$ cycloalkyl containing one or more double bonds.

"Alkoxy" means —OR where R is alkyl as defined above, e.g., methoxy, ethoxy, propoxy, 2-propoxy, acetyl and the like.

"Alkylthiol" means —SR where R is alkyl, as defined above.

"Alkylhalide" designates an alkyl group, as defined above, substituted with one or more halides (F, Cl, Br, I).

"Alkynyl" means a linear monovalent hydrocarbon of two to six carbon atoms or a branched divalent hydrocarbon of three to six carbon atoms, containing at least one triple bond, e.g., ethynyl, propynyl, and the like.

The term "halogen" refers to nonmetal elements from Group 17 of the periodic table, including fluorine, F; chlorine, Cl; bromine, Br; iodine, I; and astatine, At.

The term "amino acid side chain" refers to the side chain of any of the known alpha-amino acids such as the side chain of arginine, histidine, alanine, glycine, lysine, glutamine, leucine, valine, serine, homoserine, allothreonine, naphthylalanine, isoleucine, phenylalanine and the like. In instances in which a compound is synthesized or derivatized to include an amino acid side chain, the side chain used is preferably chosen from the side chains of the naturally-occurring amino acids.

The term "glycoside" refers to any compound that contains a carbohydrate molecule (sugar), bonded through its anomeric carbon to a non-sugar group by either an oxygen or a nitrogen atom.

The term "glucuronide" as used herein refers to the compound or metabolite that results from the reaction of glucuronic acid with an acid or alcohol or phenol moiety on the parent compound to form a covalent link between the parent compound and the glucuronic acid through a glycosidic bond.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Substituted" means that one or more hydrogen atoms on the designated atom is replaced with a selection from the indicated group, provided that the designated atom's normal valency is not exceeded, and that the substitution results in a stable compound.

"Unsubstituted" atoms bear all of the hydrogen atoms dictated by their valency. When a substituent is keto, then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Pharmaceutically-acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically-acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418.

The term "therapeutically-effective amount" or "effective amount" of a compound of this invention means an amount effective to inhibit Hsp90 in a host.

As used herein, the term "anti-cancer" or "anti-proliferative" agent includes, but is not limited to, tyrosine kinase inhibitors, paclitaxel and doxorubicin.

It will be appreciated by those skilled in the art that compounds of the invention having a chiral center may exist in, and may be isolated in, optically active and racemic forms. It is to be understood that the compounds of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase). It is also to be understood that the scope of this invention encompasses not only the various isomers, which may exist but also the various mixtures of isomers that may be formed. For example, if a compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference. Basically, the resolution of the compounds is based on the differences in the physical properties of diastereomers by attachment, either chemically or enzymatically, of an enantiomerically pure moiety resulting in forms that are separable by fractional crystallization, distillation or chromatography.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration. In a specific embodiment of the invention, the compounds of the invention that are administered in the methods of treating or preventing cancer or neurological disorders are in the cis-confirmation, and therefore another specific embodiment of the invention is a pharmaceutical composition containing a compound of the invention isolated in the cis-confirmation or containing a compound of the invention substantially in the cis-confirmation.

Because the benzoquinone ansamycins contain a quinone moiety, bioreduction of these compounds to form semiquinone and hydroquinone species is a possible metabolic pathway in tumor cells in the presence of the appropriate bioreductive enzymes. The present inventors have previously demonstrated that the active forms of these benzoquinone ansamycins are the reduced forms, the hydroquinone ansamycins (Guo, W., Reigan, P., Siegel, D., Zirrolli, J., Gustafson, D., Ross, D. *Formation of 17-Allylamino-Demethoxygeldanamycin (17-AAG) Hydroquinone by NAD(P)H:Quinone Oxidoreductase 1: Role of 17-AAG Hydroquinone in Heat Shock Protein 90 Inhibition*. Cancer Res., 65(21):10006-15 (2005); Guo, W., Reigan, P., Siegel, D., Zirrolli, J., Gustafson, D., Ross, D. *The Bioreduction of a Series of Benzoquinone Ansamycins by NAD(P)H:Quinone Oxidoreductase 1 to More Potent Heat Shock Protein 90 Inhibitors, the Hydroquinone Ansamycins*, Mol. Pharmacol., 70(4):1194-1203 (2006)).

NQO1 (DT-diaphorase, EC 1.6.99.2) is a flavoenzyme capable of utilizing either NADH or NADPH as reducing cofactors to catalyze the direct two-electron reduction of quinones to hydroquinones. Thus, amongst the bioreductive enzymes expressed in cancer cells, NQO1 is poised to have the greatest influence on the metabolism and activation of the benzoquinone ansamycins to hydroquinones. NQO1 is expressed at high levels in many human cancers including lung, colon, stomach, pancreatic and breast cancers and has been shown to increase the cytotoxicity of many quinone containing antitumor drugs such as AZQ, mitomycin C, EO9, streptonigrin, RH-1 and β-lapachone by reduction of these compounds to the corresponding hydroquinone species.

As noted above, the use of benzoquinone ansamycins has been limited by hepatotoxicity. Without intending to be bound by any one theory, it is believed that the hepatotoxicity may be a result of depletion of hepatic glutathione. Benzoquinone ansamycins can form glutathione adducts on the 19 position of the molecule. The present inventors have isolated geldanamycin and 17-DMAG-glutathione adducts after reaction of 17-AAG with reduced glutathione. A reduction or elimination of the hepatotoxicity associated with these benzoquinone ansamycins, in either the quinone or hydroquinone forms, is believed to result from diminished hepatic glutathione depletion.

The compounds of the present invention may be prepared in a number of ways well known to one skilled in the art of organic synthesis. The compounds of the present invention can be synthesized using the methods described below in the Examples section of this disclosure, together with synthetic methods known in the art of organic chemistry, or variations thereon as appreciated by those skilled in the art. Preferred methods of synthesizing the 19-methyl substituted geldanamycin fall into two general categories. The first is a conjugate addition—elimination strategy, and the second is a palladium mediated cross coupling strategy. Both approaches start with the 19-bromo or 19-iodo geldanamycin. Details of these preferred synthesis methods are provided in Examples 4, 6 and 7 of this disclosure.

The compounds of this invention may be prepared using the reactions performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions will be readily apparent to one skilled in the art and alternate methods must then be used.

The benzoquinone ansamycin starting compound is available commercially from Invivogen. Preparation of 18,21-dihydroxy-geldanamycin derivatives is described in detail in co-pending U.S. patent application Ser. No. 11/218,320 (U.S. Patent Publication No. 2006-0205705 A1), which is incorporated herein, in its entirety, by reference.

Therefore, one embodiment of the present invention is a method of forming a 19-substituted benzoquinone ansamycin or a derivative thereof by treating a benzoquinone ansamycin or derivative as described in Examples 1, 2 and 4 and shown in FIG. 1. Another embodiment is a method of forming a 19-substituted benzoquinone or dihydroquinone ansamycin, or a derivative thereof, by treating a benzoquinone ansamycin or derivative as described in Examples 1, 2 and 4 and shown in FIGS. 2 and 3.

Also provided herein are pharmaceutical compositions containing compounds of this invention and a pharmaceutically-acceptable carrier, which are media generally accepted in the art for the delivery of biologically active agents to animals, in particular, mammals. Pharmaceutically-acceptable carriers are formulated according to a number of factors well within the purview of those of ordinary skill in the art to determine and accommodate. These include, without limitation: the type and nature of the active agent being formulated; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985.

The hydroquinone ansamycin derivatives of the present invention are relatively stable, undergoing autoxidation to the corresponding quinone compound over time. This autoxidation occurs more rapidly in the presence of metal salts, and particularly in the presence of copper. Therefore, metal chelating agents can be used to prevent the autoxidation of the hydroquinone derivatives of the present invention. Thus, one embodiment of the present invention is a method of reducing the autoxidation of a hydroquinone ansamycin derivative by storing the hydroquinone ansamycin derivative in the presence of a metal chelating agent. A related embodiment is a method of reducing the autoxidation of a hydroquinone ansamycin derivative by administering a therapeutically effective amount of a hydroquinone ansamycin derivative to a mammal in the presence of a metal chelating agent. A further embodiment of the invention is a pharmaceutical composition containing at least one of the ansamycin derivatives of the present invention and a metal chelating agent.

Unfortunately, some metal chelating agents or sequestrating agents may interfere with the Hsp90 inhibitory activity of a hydroquinone ansamycin or may cause adverse effects of their own. Therefore, preferred metal chelating agents and sequestrating agents of the present invention do not interfere with the activity of a hydroquinone ansamycin and do not produce toxic or other adverse events in an animal.

The metal chelating agent may be any compound that will bind metal ions without eliminating the activity of an ansamycin hydroquinone present in a composition containing the metal chelating agent. The addition of a protein metal chelating agent may minimize formulation problems encountered with hydroquinone drugs that result from formation of the corresponding quinone by autoxidation of the hydroquinone.

Exemplary metal chelating agents suitable for use in the methods and compositions of the present invention are proteins, hereinafter referred to as "protein metal chelating agents." Preferably, these protein metal chelating agents contain the ACTUN protein motif. This protein motif was characterized by Harford, et al (Acc. Chem. Res 30:123) in 1997, and is characterized by a free amino-terminus, a histidine residue in 3rd position and two intervening peptide nitrogens. A particularly preferred protein metal chelating agent containing the ACTUN protein motif that is useful in the methods and compositions of the present invention is albumin and more preferably, human albumin. Therefore, a preferred embodiment of the present invention is a composition containing an ansamycin hydroquinone and a protein metal chelating agent having an ACTUN motif. A preferred embodiment is a composition containing an ansamycin hydroquinone and albumin and more preferably, a composition containing an ansamycin hydroquinone and human albumin.

This invention further provides a method of treating a mammal afflicted with a cancer or proliferative disorder, which includes administering to the mammal a pharmaceutical composition provided herein. Such compositions generally comprise a therapeutically effective amount of at least one compound of the invention, that is, an amount effective to ameliorate, lessen, inhibit or destroy neoplastic tissue. Such amounts typically comprise from about 0.1 to about 1000 mg of the compound per kilogram of body weight of the mammal to which the composition is administered. Therapeutically effective amounts can be administered according to any dosing regimen satisfactory to those of ordinary skill in the art. A related embodiment of the invention provides the use of any of the compounds or compositions of the invention in the preparation of a medicament for the treatment of cancer. Another embodiment of the invention relates to the use of any of the compounds or compositions of the invention for use in the treatment of a cancer.

This invention also provides a method of treating a mammal afflicted with a neurodegenerative disorder, or preventing the development of a neurodegenerative disorder, which includes administering to the mammal a composition comprising a therapeutically effective amount of a compound of the invention. Such therapeutically effective amount is effective to ameliorate, lessen, inhibit or treat a neurodegenerative disorder. Therapeutically effective amounts can be administered according to any dosing regimen satisfactory to those of ordinary skill in the art. A related embodiment of the invention provides the use of any of the compounds or compositions of the invention in the preparation of a medicament for the treatment of a neurodegenerative disorder. Another embodiment of the invention relates to the use of any of the compounds or compositions of the invention for use in the treatment of a neurodegenerative disorder.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffering agents. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration for the prevention, treatment or prophylaxis of a cancer, consisting essentially of a therapeutically-effective amount of a compound of the invention, and a pharmaceutically acceptable carrier.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn may depend upon crystal size and crystalline form. Alternatively, delayed absorption of a parenterally-administered drug is accomplished by dissolving or suspending the drug in an oil vehicle.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the therapeutic compounds of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more of the anti-cancer compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Examples of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure.

The formulations may be presented in unit-dose or multidose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The term 'pharmaceutically acceptable inert excipients' includes at least one of diluents, binders, lubricants/glidants, coloring agents and release modifying polymers.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

The dosage form may include one or more diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

The dosage form may include one or more binders in an amount of up to about 60% w/w. Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like.

Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form.

Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water-insoluble polymers include acrylates such as methacrylates, acrylic acid copolymers; cellulose derivatives such as ethylcellulose or cellulose acetate; polyethylene, and high molecular weight polyvinyl alcohols.

Additional objects, advantages, and novel features of this invention will become apparent to those skilled in the art upon examination of the following examples thereof, which are not intended to be limiting.

EXAMPLES

Example 1

Formation of a 19-Substituted Geldanamycin

19-Bromo or 19-iodo geldanamycin analogues were readily synthesized from commercially available geldanamycin by electrophilic bromination with pyridium perbromide or with iodine as shown in FIG. 1.

Example 2

Formation of a 19-Substituted Geldanamycin

Two synthetic approaches can be utilized for the synthesis of 19-methyl substituted geldanamycin derivatives: a conjugate addition—elimination strategy, and a palladium mediated cross coupling strategy. Referring to FIGS. 2 and 3, both approaches start with the readily available 19-BrGA or 19-I-GA.

The cross coupling strategy utilizes the Pd(PPh$_3$)$_4$ reagent (or alternative Pd catalysts) in the presence of appropriate ligands, and of CuX (where X is a halogen) and Me$_4$Sn, n-Bu$_3$SnPh or other stannanes.

Example 3

Toxicity of Benzoquinone Ansamycins Interaction of BA Hsp90 Inhibitors with Reduced Glutathione Benzoquinone ansamycins (BAs) can interact with glutathione, and these reactions have been associated with hepatotoxicity. Using a series of BAs, the ability of BAs to undergo conjugation with glutathione, was investigated. The BAs used were: geldanamycin (GM), 17-(allylamino)-17-demethoxygeldanamycin (17-AAG), 17-demethoxy-17-[[2-(dimethyl amino)ethyl]amino]-geldanamycin (17-DMAG), 17-(amino)-17-demethoxygeldanamycin (17-AG), and 17-demethoxy-17-[[2-(pyrrolidin-1-yl)ethyl]amino]-geldanamycin.

The interaction of BAs, including GM, 17-DMAG, 17-AAG, 17-AG, and 17AEP-GA, with glutathione was measured by HPLC and further confirmed by LC-MS (FIGS. 4 and 5). Reaction conditions were: 50 µM BA and 5 mM GSH were incubated in 50 mM potassium phosphate buffer, pH 7.4 (1 ml) at room temperature in the absence and presence of 11.8 µg of rhNQO1 and 500 µM NADH. BA-GSH conjugate formation was analyzed by HPLC at 270 nm and further confirmed by LC-MS. The amount of BA glutathione conjugate formation was quantified using [3H]glutathione. In reactions in phosphate buffer at pH 7.4 and room temperature using 5 mM reduced glutathione and 50 µM BA, approximately 45 µM GMH2-SG conjugate was formed within 5 min, which then slowly oxidized to GM-SG (FIG. 4, A). This indicates formation via a classic 1,4-reductive Michael addition generating the hydroquinone conjugate intermediates, which are then oxidized to quinone conjugates. Under the same conditions, approximately 47 µM 17-DMAG-SG conjugate was formed within 4 h, whereas 17-DMAGH2-SG was not detected (FIG. 5, A). This is likely because of the instability of 17-DMAGH2-SG conjugate and its rapid oxidation to 17-DMAG-SG during analysis. The identity of glutathione adducts was confirmed by LC-MS analysis (FIG. 4, D and FIG. 5, D). Conversely, the formation of 17-AAG-SG and 17-AG-SG was very slow under these conditions. Even after 24 h, less than 15% of 17-AAG or 17-AG was conjugated with glutathione. Under the same conditions, about 90% of 17AEP-GA was conjugated with glutathione within 10 h. The relative rate of glutathione conjugate formation in this series of BAs was GM>17-DMAG>17AEP-GA>17-AAG and 17-AG. BA-glutathione conjugate formation was pH dependent, and glutathione conjugates were not formed when the pH was <5.0.

These data demonstrate that GM (the most hepatotoxic BA in the series) had a greater propensity to react with thiols when compared with the least hepatotoxic analog, 17-AAG. Therefore, minimizing the propensity of BA derivatives to undergo glutathione conjugation while maximizing their two-electron reduction to stable Hsp90 inhibitory hydroquinones, which are properties of the 19-substituted geldanamycin derivatives of the present invention, is a useful strategy for optimizing the therapeutic index of BAs.

Example 4

Synthesis of 19-Substituted Ansamycins $^1$H NMR, $^{13}$C NMR and $^{19}$F NMR spectra were recorded on a Bruker Avance III-400, Bruker Avance 400 or Bruker DPX 400 spectrometers, operating at 400 MHz, 100 Hz and 376.5 MHz, respectively, or a Bruker Avance III-500 spectrometer, operating at 500 MHz, 125 Hz and 470.6 MHz, respectively. All spectral data was acquired at 295 K. Chemical shifts are quoted in parts per million (ppm) using the residual solvent peak as an internal standard (2.50 ppm [$^1$H NMR] for DMSO-H$_6$ and 39.52 ppm [$^{13}$C NMR] for DMSO-D$_6$). Coupling constants (J) are reported in Hz. Multiplicity abbreviations used: s singlet, d doublet, t triplet, q quartet, m multiplet. Signal assignment was accomplished by analysis of DEPT, COSY, NOESY, HMBC and HSQC experiments where necessary.

Infrared spectra were recorded on a Perkin Elmer 1600 series FT-IR spectrometer using NaCl cells. Low and high-resolution mass spectra were obtained for all novel compounds. Electrospray ionisation (ESI) and high resolution mass spectrometric (HRMS) analyses were measured on a Bruker MicroTOF spectrometer. Specific rotation values were measured on an ADP-440 digital polarimeter using a sodium lamp at 589 nm.

Melting points were determined using Riechert-Kofler hot stage apparatus and are uncorrected. Thin layer chromatography (TLC) was performed using Merck Kieselgel 60GF$_{254}$ pre-coated aluminum-backed plates. The compounds were visualised using UV light (254 nm) and basic aqueous potassium permanganate. Flash chromatography was performed at medium pressure using slurry packed Davisil silica gel 35-70 µm, 60 Å with the eluant specified. Light petroleum is the fraction with by 40-60° C. Except where specified, all reagents were purchased from commercial sources and were used without further purification. Tetrahydrofuran was distilled from sodium-benzophenone ketyl immediately before use Anhydrous dimethylformamide, was obtained from commercial sources. Water refers to distilled water. The numbering and naming of compounds does not conform to IUPAC rules, instead conforming to the traditional numbering system for the compounds of interest.

Prepared Compounds (4E,6Z,8S,9S,10E,12S,13R,14S,16R)-13-Hydroxy-21-iodo-8,14,19-trimethoxy-4,10,12,16-tetramethyl-3,20,22-trioxo-2-azabicyclo[16.3.1]docosa-1(21),4,6,10,18-pentaen-9-yl carbamate [19-iodogeldanamycin]

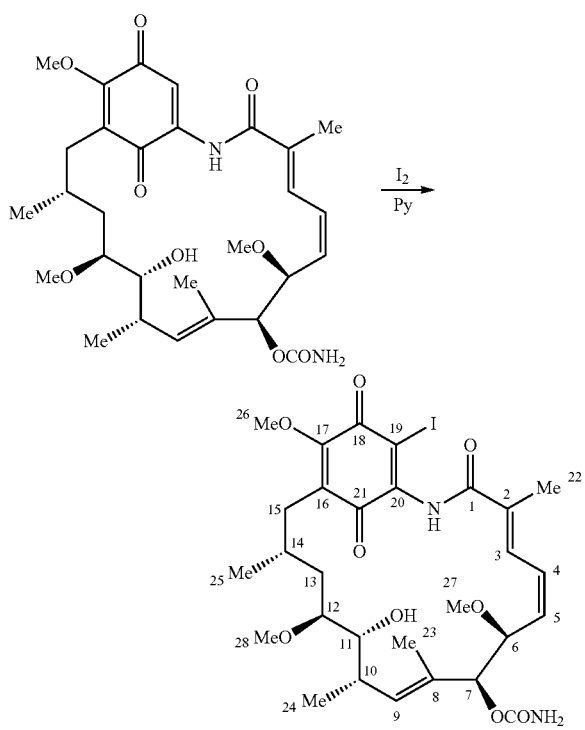

Prepared based on the description in Ger. Offen. 30 06 097 (1980).

Iodine (680 mg, 2.681 mmol, 1.5 eq.) was added to a stirred solution of geldanamycin (1.002 g, 1.787 mmol, 1.0 eq.) in pyridine (20 mL) at room temperature. After stirring the resulting solution for 16 h, an extra 0.5 eq. (227 mg) was added and the mixture was stirred for 4 h. Chloroform (100 mL) was added and the mixture was washed with saturated aqueous sodium thiosulfate solution (2×100 mL), 10% aqueous AcOH (100 mL) and brine (100 mL), before being (Na$_2$SO$_4$), filtered and concentrated in vacuo, to give an orange oil. The residue was purified by flash chromatography on silica gel, eluting with 1:2 light petroleum/ethyl acetate→ethyl acetate to give the title compound (1.196 g, 98%) as an orange solid; TLC R$_f$=0.28 (1:2 light petroleum/ethyl acetate, det: KMnO$_4$/Δ); mp 159-160° C. (lit., mp 152-154° C.); [a]$_D^{23}$+88.3 (c 0.02, CHCl$_3$); (Found: M+Na$^+$, 709.1592. C$_{29}$H$_{39}$IN$_2$O$_9$+Na$^+$, requires 709.1592); ν$_{max}$ (CHCl$_3$)/cm$^{-1}$ 3696, 3548, 3434, 2934, 1359, 1732, 1683, 1664, 1582, 1367, 1315, 1144, 1089, 1047, 988; δ$_H$ (400 MHz; DMSO-D$_6$) 9.80 (1H, s), 6.69-6.51 (2H, m), 6.37 (1H, dd, J 11.8, 10.8), 6.22 (1H, d, J 11.8), 5.26 (1H, t, J 10.8), 5.15 (1H, dd, J 10.5, 0.9), 4.88 (1H, d, J 9.5), 4.47-4.34 (1H, m), 3.95 (3H, s), 3.86 (1H, dd, J 10.8, 9.5), 3.46 (1H, dd, J 9.8, 2.9), 3.18 (3H, s), 3.02 (3H, s), 2.75 (1H, dt, J 9.9, 2.9), 2.46 (1H, dd, J 12.6, 5.8), 2.38 (1H, dd, J 12.6, 4.0), 2.12-2.00 (2H, m), 1.83 (3H, s, Me-22), 1.40 (1H, ddd, J 14.0, 9.9, 4.0), 1.17 (3H, d, J 0.9), 0.87 (3H, d, J 6.4), 0.57 (1H, ddd, J 14.0, 3.4, 2.9), 0.54 (3H, d, J 6.8); δ$_C$ (100 MHz; DMSO-D$_6$) 181.0 (C), 177.5 (C), 173.1 (C), 155.9 (C), 155.4 (C), 148.8 (C), 138.9 (C-2), 134.4 (CH) 130.6 (CH), 128.9 (C), 128.4 (C), 128.3 (CH), 123.2 (CH), 104.4 (C), 79.8 (CH), 79.5 (CH), 74.3 (CH), 71.4 (CH), 61.3 (CH$_3$), 55.7 (CH$_3$), 55.6 (CH$_3$), 35.0 (CH), 30.3 (CH$_2$), 29.6 (CH$_2$), 28.6 (CH), 18.8 (CH$_3$), 18.5 (CH$_3$), 14.0 (CH$_3$), 11.6 (CH$_3$); m/z (ESI) 709 ([M+Na]$^+$, 100%).

(4E,6Z,8S,9S,10E,12S,13R,14S,16R)-13-Hydroxy-8,14,19-trimethoxy-,10,12,16,21-pentamethyl-3,20,22-trioxo-2-azabicyclo[16.3.1]docosa-1(21),4,6,10,18-pentaen-9-yl carbamate [19-methylgeldanamycin]

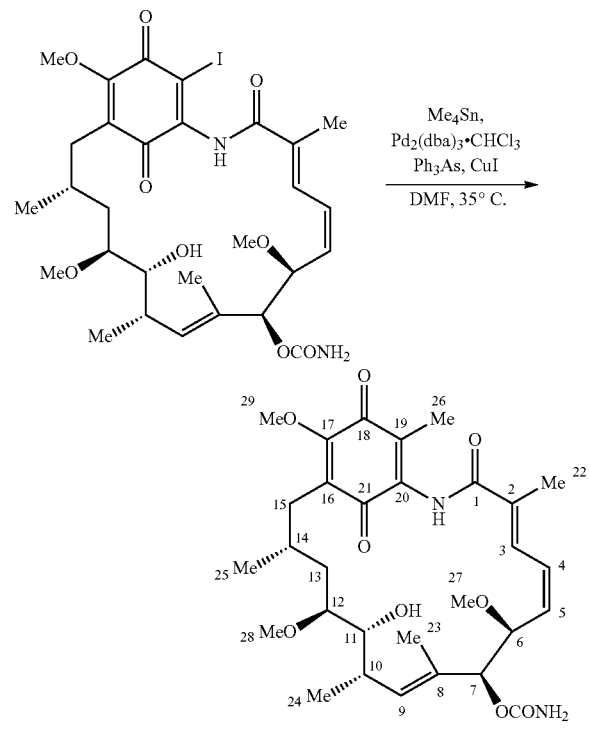

General Procedure 1:

A stirred solution of 19-iodogeldanamycin (47 mg, 0.069 mmol, 1.0 eq.), tris-(dibenzylideneacetone)dipalladium(0) (3.5 mg, 0.003 mmol, 5 mol %), triphenylarsine (4 mg, 0.014 mmol, 20 mol %) and copper (I) iodide (0.7 mg, 0.003 mmol, 5 mol %) in DMF (3 mL [ca. 0.02-0.04 M]) was sparged with argon for 20 min. Tetramethylstannane (0.011 mL, 0.082 mmol, 1.2 eq.) was added and the mixture was heated to 35° C. for 16 h. Ethyl acetate (15 mL [5 vols. relative to the volume of DMF]) was added and the mixture was washed with 5% aqueous lithium chloride solution (3×15 mL [equivalent volume to ethyl acetate]), before being (MgSO$_4$), filtered and concentrated in vacuo, preadsorbing onto silica gel. The residue was purified by flash chromatography on 10% K$_2$CO$_3$/silica gel, eluting with 1:2 light petroleum/ethyl acetate→ethyl acetate to give the title compound (34 mg, 86%) as a yellow solid; TLC R$_f$=0.29 (1:2 light petroleum/ethyl acetate, det: KMnO$_4$/Δ); mp 138-141° C.; [a]$_D^{23}$+80.8 (c 0.14, CHCl$_3$); (Found: M+Na$^+$, 597.2774. C$_{30}$H$_{42}$N$_2$O$_9$+Na$^+$, requires 579.2783); ν$_{max}$ (CHCl$_3$)/cm$^{-1}$ 3685, 3027, 2434, 1731, 1672, 1521, 1424, 1221, 929; δ$_H$ (400 MHz; DMSO-D$_6$) 9.58 (1H, s), 6.45-6.23 (2H, br. s), 6.33 (1H, dd, J 12.1, 10.5), 6.27 (1H, d, J 12.1), 5.21 (1H, t, J 10.5), 5.14 (1H, d, J 9.9), 4.86 (1H, d, J 9.3), 4.37 (1H, d, J 4.1), 3.96 (1H, dd, J 10.5, 9.3), 3.94 (3H, s), 3.46 (1H, ddd, J 0.1, 4.1, 2.5), 3.18 (3H, s), 3.04 (3H, s), 2.77 (1H, dt, J 8.7, 2.5), 2.45 (1H, dd, J 12.1, 5.2), 2.35 (1H, dd, J 12.1, 3.6), 2.11-2.10 (2H, m), 2.01 (3H, s), 1.83 (3H, s), 1.40 (1H, ddd, J 13.9, 8.7, 4.1), 1.18 (3H, s), 0.87 (3H, d, J 6.3), 0.65 (1H, ddd, J 13.9, 11.4, 2.5), 0.59 (3H, d, J 6.7); δ$_C$ (100 MHz; DMSO-D$_6$) 183.6 (C), 182.4 (C), 173.5 (C), 156.3 (C), 155.7 (C), 140.0 (C), 138.2 (C), 134.3 (CH) 130.0 (CH), 128.6 (C), 128.3 (CH), 128.2 (C), 127.7 (C), 123.0 (CH), 80.0 (CH), 79.5 (CH), 74.3 (CH), 71.5 (CH), 60.8 (CH$_3$), 55.5 (CH$_3$), 55.3 (CH$_3$), 34.7 (CH), 30.4 (CH$_2$), 29.4 (CH$_2$), 28.4 (CH), 18.7 (CH$_3$), 18.5 (CH$_3$), 13.7 (CH$_3$), 11.1 (CH$_3$), 10.2 (CH$_3$); m/z (ESI) 597 ([M+Na]$^+$, 100%).

(4E,6Z,8S,9S,10E,12S,13R,14S,16R)-13-Hydroxy-8,14,19-trimethoxy-,10,12,16,21-pentamethyl-3,20,22-trioxo-2-azabicyclo[16.3.1]docosa-1(21),4,6,10,18-pentaen-9-yl carbamate [19-phenylgeldanamycin]

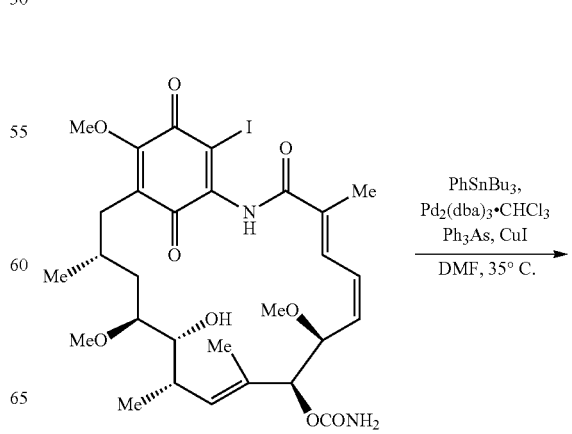

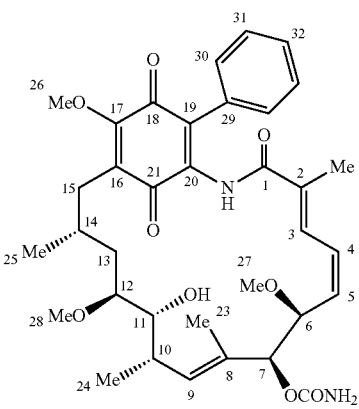

The reaction was carried out according to general procedure 1, using 19-iodogeldanamycin (131 mg, 0.191 mmol, 1.0 eq.), tris-(dibenzylideneacetone)dipalladium(0) (10 mg, 0.010 mmol, 5 mol %), triphenylarsine (12 mg, 0.038 mmol, 20 mol %) and copper (I) iodide (2 mg, 0.010 mmol, 5 mol %) in DMF (5 mL), differing only in that phenyltributylstannane (0.075 mL, 0.084 mmol, 1.2 eq.) was used instead of tetramethylstannane. Purification by flash chromatography on 10% $K_2CO_3$/silica gel, eluting with 1:2 light petroleum/ethyl acetate→ethyl acetate gave the title compound (103 mg, 85%) as an orange solid; TLC $R_f$=0.37 (ethyl acetate, det: $KMnO_4/\Delta$); mp 232-233° C.; $[\alpha]_D^{23}$+190.4 (c 0.12, $CHCl_3$); (Found: M+Na$^+$, 659.2923. $C_{35}H_{44}N_2O_9$+Na$^+$, requires 659.2939); $\nu_{max}$ ($CHCl_3$)/cm$^{-1}$ 2826, 2440, 1732, 1655, 1591, 1385, 1311, 1220; $\delta_H$ (500 MHz; DMSO-D$_6$) 9.51 (1H, s), 7.52 (2H, ddt, J 8.4, 7.2, 1.4), 7.45 (1H, tt, J 7.2, 1.4), 7.38 (2H, dd, J 8.4, 1.4), 6.54 (1H, d, J 11.6), 6.41 (1H, t, J 11.6), 6.46-6.21 (2H, br. s), 5.31 (1H, dd, J 11.6, 10.7), 5.18 (1H, d, J 10.4), 4.90 (1H, d, J 9.0), 4.37 (1H, d, J 4.3), 4.00 (1H, dd, J 10.7, 9.0), 3.97 (3H, s), 3.47 (1H, ddd, J 9.3, 4.3, 2.9), 3.20 (3H, s), 3.11 (3H, s), 2.82 (1H, dt, J 9.4, 2.9), 2.54 (1H, dd, J 12.3, 5.9), 2.41 (1H, dd, J 12.3, 4.4), 2.17-2.03 (2H, m), 1.86 (3H, s), 1.45 (1H, ddd, J 13.7, 9.4, 4.3), 1.24 (3H, s), 0.87 (3H, d, J 6.5), 0.65 (1H, ddd, J 13.7, 11.4, 2.9), 0.65 (3H, d, J 6.7); $\delta_C$ (125 MHz; DMSO-D$_6$) 184.6 (C), 181.9 (C), 173.3 (C), 157.2 (C), 156.3 (C), 140.2 (C), 139.2 (C), 134.7 (CH), 131.5 (CH), 130.2 (CH), 129.2 (C), 129.1 (C), 129.0 (C), 129.0 (CH), 128.8 (C), 128.7 (C), 128.6 (CH), 123.3 (CH), 80.4 (CH), 80.1 (CH), 74.8 (CH), 71.9 (CH), 61.5 (CH$_3$), 56.4 (CH$_3$), 56.1 (CH$_3$), 35.3 (CH), 31.2 (CH$_2$), 30.2 (CH$_2$), 29.1 (CH), 19.4 (CH$_3$), 19.0 (CH$_3$), 14.4 (CH$_3$), 12.1 (CH$_3$); m/z (ESI) 659 ([M+Na]$^+$, 100%).

(4E,6Z,8S,9S,10E,12S,13R,14S,16R)-13-Hydroxy-8,14,19-trimethoxy-4,10,12,16-tetramethyl-3,20,22-trioxo-21-vinyl-2-azabicyclo[16.3.1]docosa-1(21),4,6,10,18-pentaen-9-yl carbamate [19-vinylgeldanamycin]

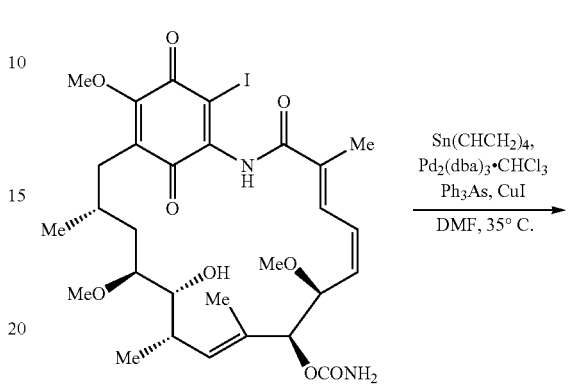

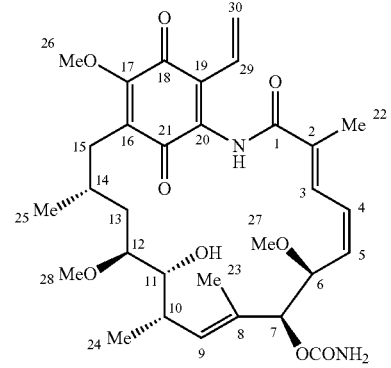

The reaction was carried out according to general procedure 1, using 19-iodogeldanamycin (143 mg, 0.208 mmol, 1.0 eq.), tris-(dibenzylideneacetone)dipalladium(0) (11 mg, 0.010 mmol, 5 mol %), triphenylarsine (13 mg, 0.042 mmol, 20 mol %) and copper (I) iodide (2 mg, 0.010 mmol, 5 mol %) in DMF (5 mL), differing only in that tetravinylstannane (0.046 mL, 0.250 mmol, 1.2 eq.) was used instead of tetramethylstannane. Purification by flash chromatography on 10% $K_2CO_3$/silica gel, eluting with 1:2 light petroleum/ethyl acetate→ethyl acetate gave the title compound (77 mg, 63%) as a brown solid; TLC $R_f$=0.34 (ethyl acetate, det: $KMnO_4/\Delta$); mp 172-173° C.; $[\alpha]_D^{23}$+21.9 (c 0.04, $CHCl_3$); (Found: M+Na$^+$, 609.2774. $C_{31}H_{42}N_2O_9$+Na$^+$, requires 609.2783); $\nu_{max}$ ($CHCl_3$)/cm$^{-1}$ 3684, 3026, 2401, 1729, 1673, 1522, 1424, 1205, 929; $\delta_H$ (500 MHz; DMSO-D$_6$) 9.82 (1H, s), 6.72 (1H, dd, J 17.7, 12.0), 6.60-6.17 (2H, br. s), 6.35 (1H, dd, J 11.6, 9.2), 6.28 (1H, dd, J 17.7, 1.9), 6.27 (1H, d, J 9.2), 5.75 (1H, dd, J 12.0, 1.9), 5.23 (1H, dd, J 11.6, 10.0), 5.15 (1H, d, J 10.5), 4.86 (1H, d, J 10.0), 4.39 (1H, br. s), 3.95 (3H, s), 3.88 (1H, t, J 10.0), 3.46 (1H, dd, J 9.2, 2.9), 3.18 (3H, s), 3.02 (3H, s), 2.78 (1H, dt, J 0.7, 2.9), 2.46 (1H, dd, J 12.5, 6.0), 2.35 (1H, dd, J 12.5, 4.4), 2.10-2.04 (2H, m), 1.84 (3H, s), 1.40 (1H, ddd, J 14.0, 9.7, 3.4), 1.20 (3H, s), 0.87 (3H, d, J 6.5), 0.65 (1H, ddd, J 14.0, 11.7, 2.9), 0.59 (3H, d, J 6.8); $\delta_C$ (125 MHz; DMSO-D$_6$) 183.9 (C), 181.9 (C), 173.6 (C), 162.3 (C), 156.5 (C), 155.8 (C), 138.7 (C), 134.4 (CH), 130.4 (CH), 128.7 (CH), 128.4 (C), 128.3 (C), 126.5 (CH), 125.3 (CH$_2$), 124.3 (C), 123.1 (CH), 79.9 (CH), 79.6 (CH), 74.3 (CH), 71.6 (CH), 60.9

(CH$_3$), 55.6 (CH$_3$), 55.5 (CH$_3$), 34.9 (CH), 30.5 (CH$_2$), 29.5 (CH$_2$), 28.5 (CH), 18.8 (CH$_3$), 18.6 (CH$_3$), 13.9 (CH$_3$), 11.3 (CH$_3$); m/z (ESI) 609 ([M+Na]$^+$, 100%).

(4E,6Z,8S,9S,10E,12S,13R,14S,16R)-21-(Furan-2-yl)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate[19-(furan-2-yl)geldanamycin]

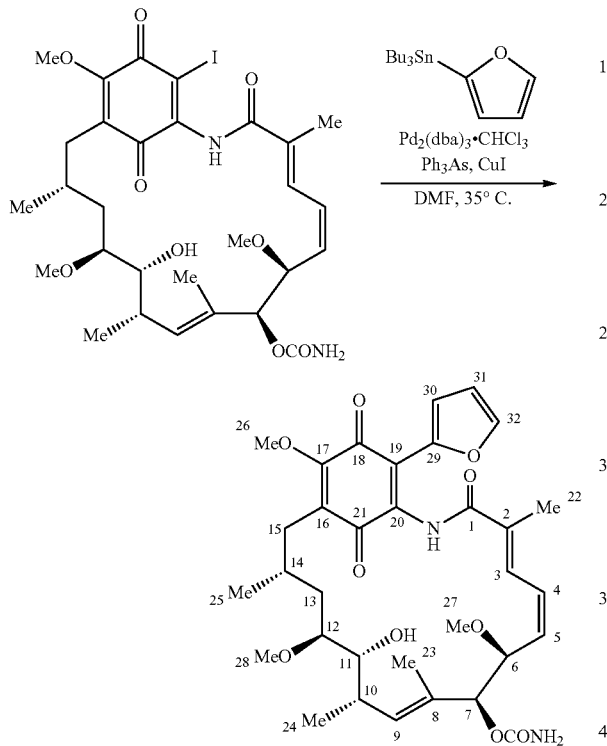

The reaction was carried out according to general procedure 1, using 19-iodogeldanamycin (311 mg, 0.453 mmol, 1.0 eq.), tris-(dibenzylideneacetone)dipalladium(0) (23 mg, 0.023 mmol, 5 mol %), triphenylarsine (28 mg, 0.091 mmol, 20 mol %) and copper (I) iodide (4 mg, 0.023 mmol, 5 mol %) in DMF (18 mL), differing only in that 2-(tributylstannyl)furan (0.171 mL, 0.544 mmol, 1.2 eq.) was used instead of tetramethylstannane. Purification by flash chromatography on 10% K$_2$CO$_3$/silica gel, eluting with 1:2 light petroleum/ethyl acetate→ethyl acetate gave the title compound (247 mg, 87%) as a deep red solid; TLC R$_f$=0.39 (ethyl acetate, det: KMnO$_4$/Δ); mp 238-239° C.; [a]$_D^{23}$+ 584.8 (c 0.03, CHCl$_3$); (Found: M+Na$^+$, 649.2735. C$_{33}$H$_{42}$N$_2$O$_{10}$+Na$^+$, requires 649.2732); ν$_{max}$ (CHCl$_3$)/cm$^{-1}$ 3776, 3012, 2434, 2415, 1735, 1660, 1602, 1522, 1477, 1424, 1239, 1017, 929; δ$_H$ (400 MHz; DMSO-D$_6$) 9.74 (1H, s), 8.02 (1H, d, J 1.4), 7.20 (1H, d, J 3.5), 6.74 (1H, dd, J 3.5, 1.4), 6.48 (1H, d, J 12.0), 6.43-6.21 (2H, br. s), 6.37 (1H, dd, J 12.0, 10.7), 5.24 (1H, t, J 10.7), 5.15 (1H, d, J 10.3), 4.84 (1H, d, J 9.4), 4.38 (1H, d, J 4.2), 3.97 (3H, s), 3.75 (1H, dd, J 10.7, 9.4), 3.47 (1H, ddd, J 9.5, 4.2, 2.7), 3.19 (3H, s), 3.00 (3H, s), 2.79 (1H, dt, J 0.1, 2.7), 2.50 (1H, dd, J 12.4, 6.5), 2.39 (1H, dd, J 12.4, 4.3), 2.16-2.03 (2H, m), 1.87 (3H, s), 1.43 (1H, ddd, J 14.3, 9.7, 4.0), 1.12 (3H, s), 0.86 (3H, d, J 6.4), 0.65 (1H, ddd, J 14.3, 11.8, 2.7), 0.61 (3H, d, J 6.7); δ$_C$ (100 MHz; DMSO-D$_6$) 183.5 (C), 180.3 (C), 173.0 (C), 156.1 (C), 155.7 (C), 145.1 (CH), 145.0 (C), 139.0 (C), 135.8 (C), 134.3 (CH), 130.3 (CH), 128.9 (C), 128.3 (CH), 128.2 (C), 123.1 (CH), 118.4 (C), 116.6 (CH), 112.2 (CH), 79.7 (CH), 79.5 (CH), 74.3 (CH), 71.4 (CH), 60.9 (CH$_3$), 55.6 (CH$_3$), 55.6 (CH$_3$), 34.8 (CH), 30.4 (CH$_2$), 29.5 (CH$_2$), 28.4 (CH), 18.7 (CH$_3$), 18.5 (CH$_3$), 13.8 (CH$_3$), 11.2 (CH$_3$); m/z (ESI) 649 ([M+Na]$^+$, 100%).

(4E,6Z,8S,9S,10E,12S,13R,14S,16R)-13-Hydroxy-8,14,19-trimethoxy-4,10,12,16-tetramethyl-3,20,22-trioxo-21-(thiophen-2-yl)-2-azabicyclo[16.3.1]docosa-1(21),4,6,10,18-pentaen-9-yl carbamate[19-(thiophen-2-yl)geldanamycin]

The reaction was carried out according to general procedure 1, using 19-iodogeldanamycin (51 mg, 0.074 mmol, 1.0 eq.), tris-(dibenzylideneacetone)dipalladium(0) (4 mg, 0.004 mmol, 5 mol %), triphenylarsine (5 mg, 0.015 mmol, 20 mol %) and copper (I) iodide (0.7 mg, 0.004 mmol, 5 mol %) in DMF (3 mL), differing only in that 2-(tributylstannyl)thiophene (0.029 mL, 0.089 mmol, 1.2 eq.) was used instead of tetramethylstannane. Purification by flash chromatography on 10% K$_2$CO$_3$/silica gel, eluting with 1:2 light petroleum/ethyl acetate→ethyl acetate gave the title compound (45 mg, 94%) as a red solid; TLC R$_f$=0.64 (ethyl acetate, det: KMnO$_4$/Δ); mp 242-243° C.; [a]$_D^{23}$+958.0 (c 0.03, CHCl$_3$); (Found: M+Na$^+$, 665.2486. C$_{33}$H$_{42}$N$_2$O$_9$S+ Na$^+$, requires 665.2503); ν$_{max}$ (CHCl$_3$)/cm$^{-1}$ 3689, 3007, 2359, 2340, 1732, 1661, 1601, 1584, 1368, 1320, 1283, 1091, 927; δ$_H$ (500 MHz; DMSO-D$_6$) 9.83 (1H, s), 7.91 (1H, dd, J 5.0, 0.7), 7.77 (1H, dd, J 3.9, 0.7), 7.28 (1H, dd, J 5.0, 3.9), 6.46 (1H, d, J 11.7), 6.43-6.19 (2H, br. s), 6.39 (1H, dd, J 11.0, 10.5), 5.23 (1H, dd, J 11.7, 10.5), 5.14 (1H, d, J 10.5), 4.84 (1H, d, J 9.4), 4.42 (1H, d, J 4.2), 3.98 (3H, s), 3.78 (1H, dd, J 11.0, 9.4), 3.46 (1H, ddd, J 0.5, 4.2, 2.8), 3.19 (3H, s), 3.01 (3H, s), 2.77 (1H, dt, J 0.4, 2.8), 2.52 (1H, dd, J 12.4, 5.9), 2.40 (1H, dd, J 12.4, 4.3), 2.11-2.04 (2H, m), 1.87 (3H, s), 1.44 (1H, ddd, J 14.1, 9.4, 4.1), 1.10 (3H, s), 0.85 (3H, d, J 6.5), 0.64 (1H, dd, J 14.1, 11.7, 2.8), 0.60 (3H, d, J 6.7); $\delta_C$ (125 MHz; DMSO-D$_6$) 183.6 (C), 181.1 (C), 173.3 (C), 156.4 (C), 155.8 (C), 139.9 (C), 137.0 (C), 134.4 (CH), 132.2 (CH), 131.0 (CH), 130.6 (CH), 129.0 (C), 128.4 (C), 128.3 (CH), 127.5 (CH), 124.2 (C), 122.5 (CH), 117.9 (C), 79.8 (CH), 79.6 (CH), 74.4 (CH), 71.4 (CH), 61.1 (CH$_3$), 55.7 (CH$_3$), 55.7 (CH$_3$), 34.9 (CH), 30.5 (CH$_2$), 29.5 (CH$_2$), 28.6 (CH), 18.7 (CH$_3$), 18.7 (CH$_3$), 14.1 (CH$_3$), 11.5 (CH$_3$); m/z (ESI) 665 ([M+Na]$^+$, 100%).

(4E,6Z,8S,9S,10E,12S,13R,14S,16R)-13-Hydroxy-8,14,19-trimethoxy-21-(4-methoxyphenyl)-4,10,12,16-tetramethyl-3,20,22-trioxo-2-azabicyclo[16.3.1]docosa-1(21),4,6,10,18-pentaen-9-yl carbamate [19-(4-methoxyphenyl)geldanamycin]

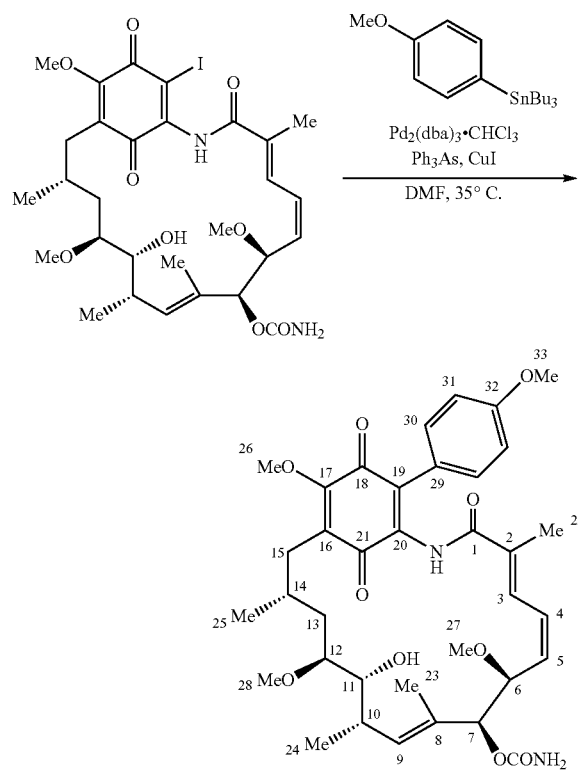

The reaction was carried out according to general procedure 1, using 19-iodogeldanamycin (50 mg, 0.073 mmol, 1.0 eq.), tris-(dibenzylideneacetone)dipalladium(0) (4 mg, 0.004 mmol, 5 mol %), triphenylarsine (5 mg, 0.015 mmol, 20 mol %) and copper (I) iodide (0.7 mg, 0.004 mmol, 5 mol %) in DMF (3 mL), differing only in that tributyl(4-methoxyphenyl)stannane (0.035 g, 0.087 mmol, 1.2 eq.) was used instead of tetramethylstannane. Purification by flash chromatography on 10% K$_2$CO$_3$/silica gel, eluting with 1:2 light petroleum/ethyl acetate→ethyl acetate gave the title compound (27 mg, 56%) as an orange solid; TLC R$_f$=0.35 (ethyl acetate, det: KMnO$_4$/Δ); mp 136-137° C.; $[\alpha]_D^{23}$+340.3 (c 0.2, CHCl$_3$); (Found: M+Na$^+$, 689.3030. C$_{36}$H$_{46}$N$_2$O$_{10}$+Na$^+$, requires 689.3045); $\nu_{max}$ (CHCl$_3$)/cm$^{-1}$ 3696, 2928, 2304, 1670, 1602, 1456, 1365, 1100, 878, 839; $\delta_H$ (500 MHz; DMSO-D$_6$) 9.48 (1H, s), 7.34 (2H, d, J 8.9), 7.10 (2H, d, J 8.9), 6.51 (1H, d, J 11.7), 6.54-6.20 (2H, br. s), 6.41 (1H, dd, J 11.7, 10.7), 5.29 (1H, t, J 10.7), 5.16 (1H, d, J 10.4), 4.89 (1H, d, J 10.7), 4.40 (1H, d, J 4.2), 3.96 (1H, t, J 10.7), 3.96 (3H, s), 3.83 (3H, s), 3.47 (1H, ddd, J 8.7, 4.2, 2.5), 3.20 (3H, s), 3.10 (3H, s), 2.81 (1H, dt, J 9.4, 2.5), 2.54 (1H, dd, J 12.4, 5.9), 2.40 (1H, dd, J 12.4, 4.4), 2.13-2.04 (2H, m), 1.86 (3H, s), 1.44 (1H, ddd, J 13.8, 9.4, 4.0), 1.20 (3H, s), 0.86 (3H, d, J 6.5), 0.69 (1H, dd, J 13.8, 10.8, 2.5), 0.64 (3H, d, J 6.7); $\delta_C$ (125 MHz; DMSO-D$_6$) 184.2 (C), 181.7 (C), 172.9 (C), 159.4 (C), 156.7 (C), 155.8 (C), 139.2 (C), 134.2 (CH), 131.3 (CH), 130.4 (CH), 130.2 (C), 129.1 (C), 128.7 (C), 128.5 (CH), 128.3 (C), 123.0 (CH), 122.5 (C), 113.7 (CH), 79.9 (CH), 79.7 (CH), 74.8 (CH), 71.4 (CH), 61.0 (CH$_3$), 55.9 (CH$_3$), 55.7 (CH$_3$), 55.3 (CH$_3$), 34.8 (CH), 30.6 (CH$_2$), 29.7 (CH$_2$), 28.7 (CH), 18.9 (CH$_3$), 18.6 (CH$_3$), 14.0 (CH$_3$), 11.7 (CH$_3$); m/z (ESI) 689 ([M+Na]$^+$, 100%).

(4E,6Z,8S,9S,10E,12S,13R,14S,16R)-21-(4-Fluorophenyl)-13-hydroxy-8,14,19-trimethoxy-4,10,12,16-tetramethyl-3,20,22-trioxo-2-azabicyclo[16.3.1]docosa-1(21),4,6,10,18-pentaen-9-yl carbamate [19-(4-fluorophenyl)geldanamycin]

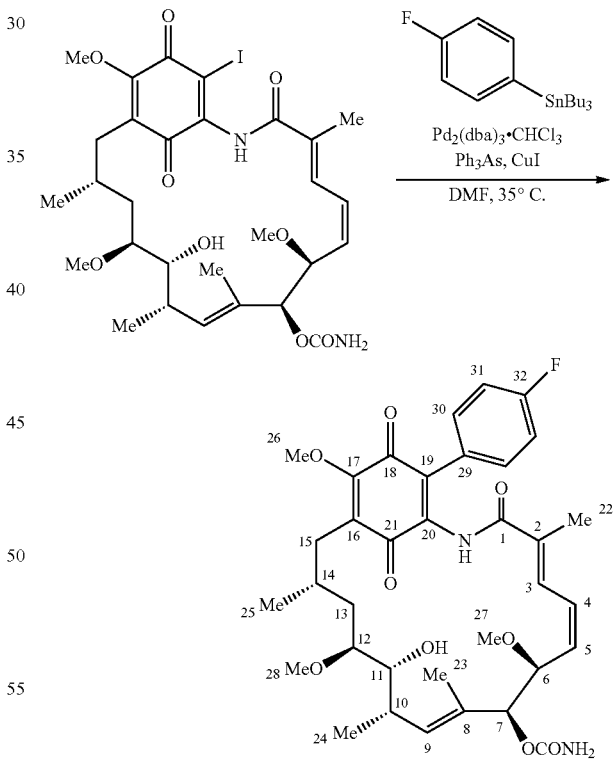

The reaction was carried out according to general procedure 1, using 19-iodogeldanamycin (51 mg, 0.074 mmol, 1.0 eq.), tris-(dibenzylideneacetone)dipalladium(0) (4 mg, 0.004 mmol, 5 mol %), triphenylarsine (5 mg, 0.015 mmol, 20 mol %) and copper (I) iodide (0.7 mg, 0.004 mmol, 5 mol %) in DMF (3 mL), differing only in that tributyl(4-methoxyphenyl)stannane (0.032 mL, 0.089 mmol, 1.2 eq.) was used instead of tetramethylstannane. Purification by flash chromatography on 10% K$_2$CO$_3$/silica gel, eluting with 1:2 light petroleum/ethyl acetate→ethyl acetate gave the title compound (39 mg, 80%) as an orange solid; TLC R$_f$=0.35 (ethyl acetate, det: KMnO$_4$/Δ); mp 140-142° C.; [a]$_D^{23}$+137.4 (c 0.02, CHCl$_3$); (Found: M+Na$^+$, 677.2824. C$_{35}$H$_{43}$FN$_2$O$_9$+Na$^+$, requires 677.2824); ν$_{max}$ (CHCl$_3$)/cm$^{-1}$ 3686, 3008, 2434, 1731, 1712, 1658, 1602, 1510, 1366, 1290, 1244, 1160, 989; δ$_H$ (500 MHz; DMSO-D$_6$) 9.61 (1H, s), 7.43 (2H, dd, J 8.9, J$_{H-F}$ 5.7), 7.37 (2H, dd, J 8.9, J$_{H-F}$ 8.9), 6.52 (1H, d, J 11.1), 6.46-6.17 (2H, br. s), 6.41 (1H, dd, J 11.1, 10.7), 5.32 (1H, t, J 10.7), 5.18 (1H, d, J 10.3), 4.89 (1H, d, J 9.0), 4.40 (1H, m), 3.99 (1H, dd, J 10.7, 9.0), 3.97 (3H, s), 3.47-3.46 (1H, m), 3.20 (3H, s), 3.11 (3H, s), 2.82 (1H, dt, J 8.7, 2.7), 2.54 (1H, dd, J 12.5, 5.9), 2.41 (1H, dd, J 12.5, 4.4), 2.10-2.07 (2H, m), 1.85 (3H, s), 1.44 (1H, ddd, J 14.7, 5.4, 2.7), 1.21 (3H, s), 0.86 (3H, d, J 6.7), 0.82 (1H, ddd, J 14.7, 11.6, 8.7), 0.65 (3H, d, J 6.4); δ$_C$ (125 MHz; DMSO-D$_6$) 184.1 (C), 181.3 (C), 172.9 (C), 162.0 (d, J$_{C-F}$ 246), 156.7 (C), 155.8 (C), 139.9 (C), 134.2 (CH), 132.1 (d, J$_{C-F}$ 9, CH), 130.7 (CH), 129.8 (C), 129.0 (C), 128.7 (C), 128.6 (C), 128.2 (CH), 127.4 (d, J$_{C-F}$ 3, C), 122.9 (CH), 115.3 (d, J$_{C-F}$ 22, CH), 79.9 (CH), 79.7 (CH), 75.0 (CH), 71.4 (CH), 61.0 (CH$_3$), 55.9 (CH$_3$), 55.9 (CH$_3$), 34.6 (CH), 31.3 (CH$_2$), 29.7 (CH$_2$), 28.6 (CH), 19.0 (CH$_3$), 18.5 (CH$_3$), 14.0 (CH$_3$), 11.6 (CH$_3$); δ$_F$ (376.5 MHz; DMSO-D$_6$) −115.7; m/z (ESI) 677 ([M+Na]$^+$, 100%).

(4E,6Z,8S,9S,10E,12S,13R,14S,16R)-13-Hydroxy-8,14,19-trimethoxy-4,10,12,16-tetramethyl-3,20,22-trioxo-21-(pyridin-2-yl)-2-azabicyclo[16.3.1]docosa-1(21),4,6,10,18-pentaen-9-yl carbamate [19-(pyridine-2-yl)geldanamycin]

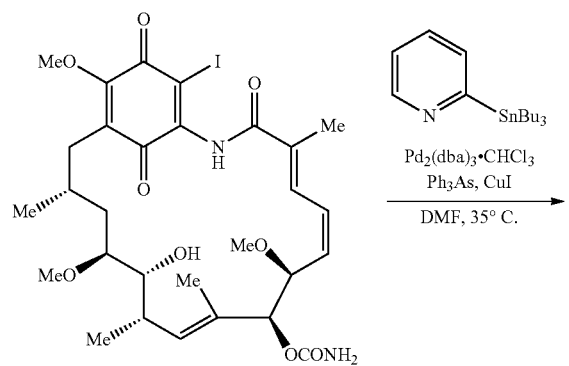

The reaction was carried out according to general procedure 1, using 19-iodogeldanamycin (47 mg, 0.069 mmol, 1.0 eq.), tris-(dibenzylideneacetone)dipalladium(0) (4 mg, 0.003 mmol, 5 mol %), triphenylarsine (4 mg, 0.014 mmol, 20 mol %) and copper (I) iodide (0.7 mg, 0.003 mmol, 5 mol %) in DMF (3 mL), differing only in that tributyl(4-methoxyphenyl)stannane (0.027 mL, 0.082 mmol, 1.2 eq.) was used instead of tetramethylstannane. Purification by flash chromatography on 10% K$_2$CO$_3$/silica gel, eluting with 1:2 light petroleum/ethyl acetate→ethyl acetate gave the title compound (13 mg, 30%) as an orange solid; TLC R$_f$=0.33 (ethyl acetate, det: KMnO$_4$/Δ); mp 198-200° C.; [a]$_D^{23}$+23.1 (c 0.03, CHCl$_3$); (Found: M+H$^+$, 638.3075. C$_{34}$H$_{44}$N$_3$O$_9^+$, requires 638.3072); ν$_{max}$ (CHCl$_3$)/cm$^{-1}$ 3606, 3002, 2789, 2350, 2182, 1924, 1600, 1445, 1147, 1056, 1044, 1034, 1018, 935; δ$_H$ (500 MHz; DMSO-D$_6$) 9.96 (1H, s), 8.70 (1H, ddd, J 4.8, 1.6, 1.1), 7.94 (1H, td, J 7.8, 1.6), 7.49-7.45 (2H, m), 7.07 (1H, d, J 11.9), 6.43-6.15 (2H, br. s), 6.37 (1H, dd, J 11.9, 10.7), 5.25 (1H, t, J 10.7), 5.12 (1H, dd, J 10.5, 0.8), 4.85 (1H, d, J 9.6), 4.39 (1H, d, J 4.0), 4.19 (1H, dd, J 10.7, 9.6), 3.98 (3H, s), 3.47 (1H, ddd, J 9.5, 4.0, 2.9), 3.19 (3H, s), 3.11 (3H, s), 2.79 (1H, dt, J 9.7, 2.9), 2.54 (1H, dd, J 12.4, 5.8), 2.43 (1H, dd, J 12.4, 4.1), 2.15-2.01 (2H, m), 1.83 (3H, s), 1.44 (1H, ddd, J 13.8, 9.7, 4.1), 1.18 (3H, d, J 0.8), 0.86 (3H, d, J 6.5), 0.69 (1H, ddd, J 13.8, 11.6, 2.9), 0.61 (3H, d, J 6.8); δ$_C$ (125 MHz; DMSO-D$_6$) 184.4 (C), 181.1 (C), 173.3 (C), 156.5 (C), 155.9 (C), 150.7 (C), 149.1 (CH), 141.0 (C), 138.8 (C), 136.2 (CH), 133.8 (CH), 130.8 (CH), 128.9 (C), 128.8 (C), 128.5 (CH), 127.1 (CH), 125.8 (C), 125.1 (CH), 123.5 (CH), 79.6 (CH), 79.2 (CH), 74.4 (CH), 71.4 (CH), 61.1 (CH$_3$), 55.8 (CH$_3$), 55.7 (CH$_3$), 34.9 (CH), 30.4 (CH$_2$), 29.4 (CH$_2$), 28.7 (CH), 18.9 (CH$_3$), 18.6 (CH$_3$), 13.7 (CH$_3$), 11.9 (CH$_3$); m/z (ESI) 638 ([M+H]$^+$, 100%).

(4E,6Z,8S,9S,10E,12S,13R,14S,16R)-19-(Allylamino)-13-hydroxy-8,14-dimethoxy-4,10,12,16,21-pentamethyl-3,20,22-trioxo-2-azabicyclo[16.3.1]docosa-1(21),4,6,10,18-pentaen-9-yl carbamate [19-methyl-AAG]

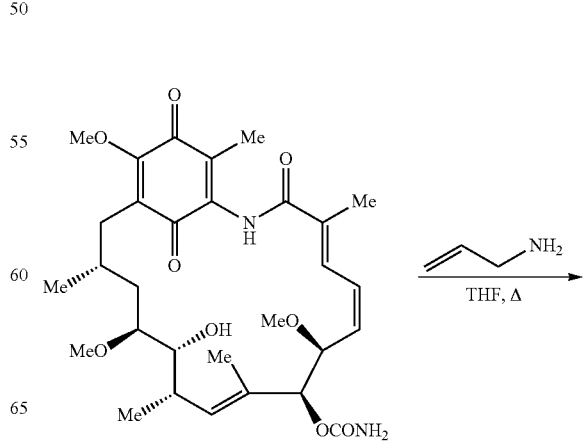

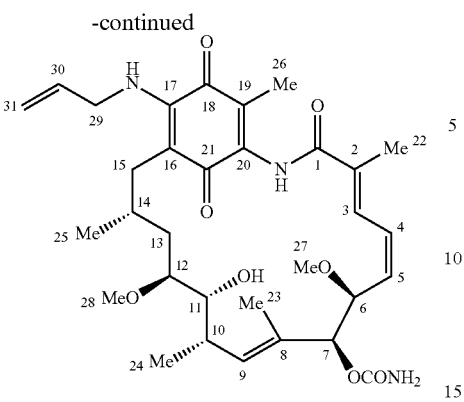

General Procedure 2:

Allylamine (0.003 mL, 0.044 mmol, 5 eq.) was added to a stirred solution of 19-methylgeldanamycin (5 mg, 0.009 mmol, 1.0 eq.) in THF (1 mL [ca. 0.01 M]) under argon and the mixture was heated to lux for 16 hours. After cooling, the mixture was concentrated in vacuo and the residue was purified by flash chromatography on silica gel, eluting with 1:2 light petroleum/ethyl acetate→ethyl acetate to give the title compound (6 mg, quantitative yield) as a purple solid; TLC $R_f$=0.45 (ethyl acetate, det: KMnO$_4$/Δ); mp 139-141° C.; $[\alpha]_D^{23}$+99.6 (c 0.04, CHCl$_3$); (Found: M+Na$^+$, 622.3106. C$_{32}$H$_{45}$N$_3$O$_8$+Na$^+$, requires 622.3099); $\nu_{max}$ (CHCl$_3$)/cm$^{-1}$ 3685, 3012, 2434, 2415, 1721, 1602, 1522, 1424, 1239, 929; $\delta_H$ (400 MHz; DMSO-D$_6$) 9.38 (1H, s), 6.79 (1H, t, J 7.0), 6.61-6.16 (2H, br. s), 6.31 (1H, dd, J 11.9, 10.6), 6.20 (1H, d, J 11.9), 5.88 (1H, ddt, J 15.5, 10.1, 5.1), 5.19 (1H, t, J 10.6), 5.09-5.03 (3H, m), 4.84 (1H, d, J 9.4), 4.52 (1H, d, J 4.3), 4.06-4.00 (2H, m), 3.95 (1H, dd, J 10.6, 9.4), 3.45-3.39 (1H, m), 3.20 (3H, s), 3.04 (3H, s), 2.90-2.85 (1H, m), 2.58 (1H, dd, J 13.8, 8.8), 2.19-2.01 (3H, m), 1.96 (3H, s), 1.86 (3H, s), 1.19 (3H, s), 1.14-1.11 (1H, m), 0.86 (3H, d, J 6.0), 0.85 (3H, d, J 6.5), 0.80-0.70 (1H, m); $\delta_C$ (125 MHz; DMSO-D$_6$) 184.1 (C), 180.3 (C), 174.2 (C), 155.9 (C), 144.0 (C), 141.7 (C), 139.0 (C), 135.9 (CH), 134.0 (CH), 130.3 (CH), 128.7 (C), 128.1 (CH), 124.5 (C), 121.9 (CH), 115.3 (CH$_2$), 109.6 (C), 80.7 (CH), 79.9 (CH), 74.7 (CH), 73.8 (CH), 55.7 (CH$_3$), 55.6 (CH$_3$), 45.8 (CH$_2$), 34.7 (CH), 30.4 (CH$_2$), 30.0 (CH$_2$), 29.9 (CH), 20.9 (CH$_3$), 18.4 (CH$_3$), 14.1 (CH$_3$), 11.1 (CH$_3$), 10.4 (CH$_3$); m/z (ESI) 622 ([M+Na]$^+$, 100%).

(4E,6Z,8S,9S,10E,12S,13R,14S,16R)-19-(Allylamino)-13-hydroxy-8,14-dimethoxy-4,10,12,16-tetramethyl-3,20,22-trioxo-21-phenyl-2-azabicyclo[16.3.1]docosa-1(21),4,6,10,18-pentaen-9-yl carbamate [19-phenyl-AAG]

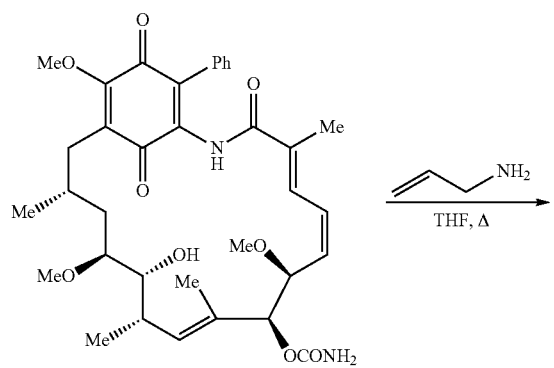

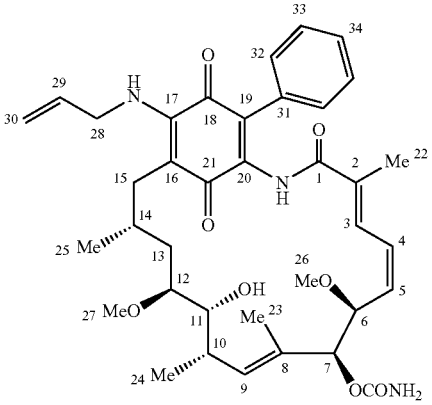

The reaction was carried out according to general procedure 2, using allylamine (0.005 mL, 0.063 mmol, 5 eq.) in THF (1 mL), differing only in that 19-phenylgeldanamycin (8 mg, 0.013 mmol, 1.0 eq.) was used instead of 19-methylgeldanamycin. Purification by flash chromatography on silica gel, eluting with ethyl acetate gave the title compound (9 mg, quantitative yield) as a purple solid; TLC $R_f$=0.44 (ethyl acetate, det: KMnO$_4$/Δ); mp 184-185° C.; $[\alpha]_D^{23}$+ 141.6 (c 0.03, CHCl$_3$); (Found: M+Na$^+$, 684.3241. C$_{37}$H$_{47}$N$_3$O$_8$+Na$^+$, requires 684.3255); $\nu_{max}$ (CHCl$_3$)/cm$^{-1}$ 3520, 3405, 2993, 2912, 2344, 2317, 1729, 1655, 1581, 1459, 1365, 1189, 1108; $\delta_H$ (400 MHz; DMSO-D$_6$) 9.23 (1H, s), 7.50 (2H, dd, J 8.4, 7.4), 7.42 (1H, tt, J 7.4, 1.4), 7.35 (2H, dd, J 8.4, 1.4), 6.91 (1H, t, J 6.8), 6.53-6.17 (2H, br. s), 6.48 (1H, d, J 11.8), 6.39 (1H, dd, J 11.8, 10.6), 5.92 (1H, ddt, J 15.3, 10.1, 4.9), 5.29 (1H, t, J 10.6), 5.14 (1H, d, J 9.3), 5.11 (1H, dd, J 15.3, 1.5), 5.10 (1H, dd, J 10.1, 1.5), 4.89 (1H, d, J 9.2), 4.54 (1H, d, J 4.4), 4.11-4.04 (2H, m), 4.02 (1H, dd, J 10.6, 9.2), 3.45 (1H, ddd, J 0.6, 4.4, 2.7), 3.23 (3H, s), 3.12 (3H, s), 2.92 (1H, quintet, J 2.7), 2.67 (1H, dd, J 14.8, 9.9), 2.21-2.09 (3H, m), 1.89 (3H, s), 1.29 (3H, s), 1.24-1.19 (1H, m), 0.92 (3H, d, J 6.0), 0.86 (3H, d, J 6.5), 0.85-0.81 (1H, m); $\delta_C$ (125 MHz; DMSO-D$_6$) 182.9 (C), 180.0 (C), 173.4 (C), 155.9 (C), 144.7 (C), 141.5 (C), 139.4 (C), 136.1 (CH), 133.9 (CH), 131.8 (C), 130.6 (CH), 129.7 (CH), 128.8 (C), 128.2 (CH), 128.1 (CH), 128.0 (CH), 126.8 (C), 121.7 (CH), 115.4 (CH$_2$), 110.1 (C), 80.7 (CH), 79.8 (CH), 75.2 (CH), 73.8 (CH), 56.0 (CH$_3$), 55.7 (CH$_3$), 46.1 (CH$_2$), 34.8 (CH), 30.5 (CH$_2$), 30.2 (CH$_2$), 30.0 (CH), 21.0 (CH$_3$), 18.4 (CH$_3$), 14.2 (CH$_3$), 11.6 (CH$_3$); m/z (ESI) 684 ([M+Na]$^+$, 100%).

(4E,6Z,8S,9S,10E,12S,13R,14S,16R)-19-(Allylamino)-21-(furan-2-yl)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate [19-(furan-2-yl)-AAG]

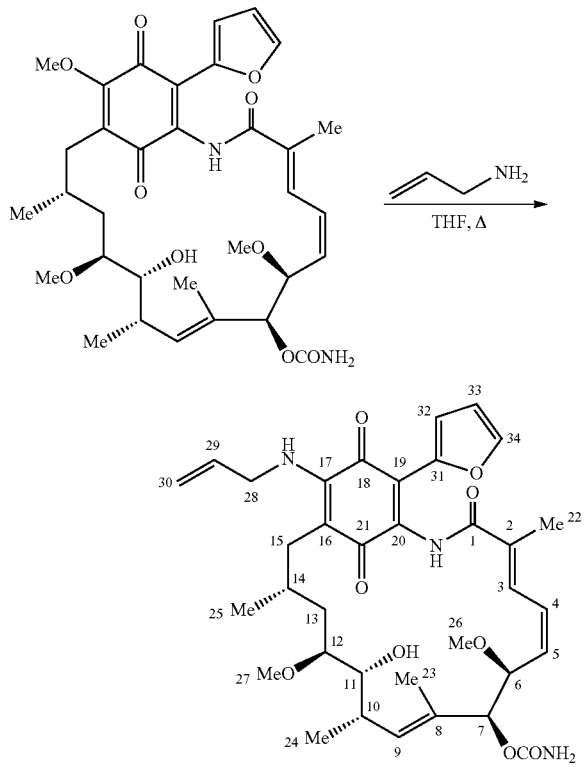

The reaction was carried out according to general procedure 2, using allylamine (0.0006 mL, 0.223 mmol, 5 eq.) in THF (1 mL), differing only in that 19-(furan-2-yl)geldanamycin (1 mg, 0.002 mmol, 1.0 eq.) was used instead of 19-methylgeldanamycin and the mixture was stirred at room temperature for 16 h to avoid double addition. Purification by flash chromatography on silica gel, eluting with ethyl acetate gave the title compound (1 mg, 96%) as a dark green solid; TLC $R_f$=0.42 (ethyl acetate, det: KMnO$_4$/Δ); mp 244-246° C.; $[a]_D^{23}$ −269.3 (c 0.03, CHCl$_3$); (Found: M+Na$^+$, 674.3046. C$_{35}$H$_{45}$N$_3$O$_9$+Na$^+$, requires 674.3048); $v_{max}$ (CHCl$_3$)/cm$^{-1}$ 3542, 3430, 3005, 2928, 2855, 1729, 1680, 1658, 1457, 1368, 1324, 1103; $\delta_H$ (400 MHz; DMSO-D$_6$) 9.55 (1H, s), 7.94 (1H, d, J 1.2), 7.07 (1H, d, J 3.4), 6.97 (1H, t, J 6.7), 6.69 (1H, dd, J 3.4, 1.2), 6.49-6.22 (2H, br. s), 6.46 (1H, d, J 11.9), 6.35 (1H, dd, J 11.9, 10.7), 5.91 (1H, ddt, J 16.1, 10.1, 5.0), 5.21 (1H, t, J 10.7), 5.11-5.07 (3H, m), 4.82 (1H, d, J 9.4), 4.51 (1H, d, J 4.3), 4.10-4.01 (2H, m), 3.77 (1H, dd, J 10.7, 9.4), 3.43 (1H, ddd, J 0.5, 4.3, 2.8), 3.21 (3H, s), 3.01 (3H, s), 2.89 (1H, quintet, J 2.8), 2.63 (1H, dd, J 15.2, 10.1), 2.15 (1H, dd, J 15.2, 4.1), 2.15-2.10 (1H, m), 2.10-2.03 (1H, m), 1.89 (3H, s), 1.24-1.17 (1H, m), 1.14 (3H, s), 0.87 (3H, d, J 6.0), 0.85 (3H, d, J 6.5), 0.81-0.75 (1H, m); $\delta_C$ (100 MHz; DMSO-D$_6$) 182.3 (C), 180.3 (C), 173.7 (C), 156.9 (C), 145.9 (C), 144.7 (C), 144.6 (CH), 140.2 (C), 138.8 (C), 136.2 (CH), 134.4 (CH), 131.5 (CH), 129.1 (C), 128.5 (CH), 122.0 (CH), 116.5 (C), 116.0 (CH$_2$), 115.3 (CH), 112.4 (CH), 110.1 (C), 81.1 (CH), 80.3 (CH), 75.1 (CH), 74.2 (CH), 56.3 (CH$_3$), 56.2 (CH$_3$), 46.4 (CH$_2$), 35.2 (CH), 30.9 (CH$_2$), 30.6 (CH$_2$), 30.4 (CH), 21.3 (CH$_3$), 18.8 (CH$_3$), 14.5 (CH$_3$), 11.7 (CH$_3$); m/z (ESI) 674 ([M+Na]$^+$, 100%).

(4E,6Z,8S,9S,10E,12S,13R,14S,16R)-19-(Allylamino)-13-hydroxy-8,14-dimethoxy-4,10,12,16-tetramethyl-3,20,22-trioxo-21-(thiophen-2-yl)-2-azabicyclo[16.3.1]docosa-1(21),4,6,10,18-pentaen-9-yl carbamate [19-(thiophen-2-yl)-AAG]

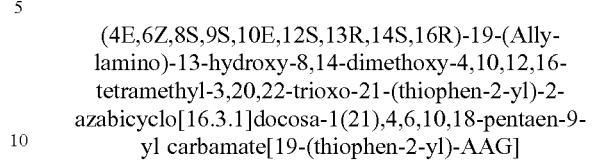

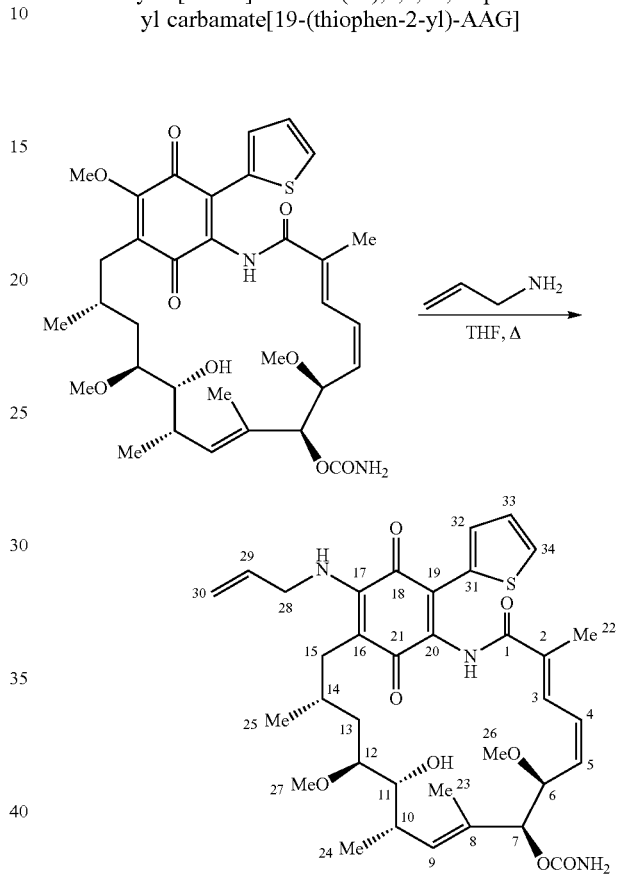

The reaction was carried out according to general procedure 2, using allylamine (0.004 mL, 0.047 mmol, 5 eq.) in THF (2 mL), differing only in that 19-(thiophen-2-yl) geldanamycin (6 mg, 0.009 mmol, 1.0 eq.) was used instead of 19-methylgeldanamycin. Purification by flash chromatography on silica gel, eluting with 2:1 light petroleum/ethyl acetate→ethyl acetate gave the title compound (3 mg, 48%) as a purple solid; TLC $R_f$=0.39 (ethyl acetate, det: KMnO$_4$/Δ); mp 180-181° C.; $[a]_D^{23}$ +473.2 (c 0.01, CHCl$_3$); (Found: M+Na$^+$, 690.2813. C$_{35}$H$_{45}$N$_3$O$_8$S+Na$^+$, requires 690.2820); $v_{max}$ (CHCl$_3$)/cm$^{-1}$ 3685, 3011, 2435, 1728, 1659, 1602, 1582, 1517, 1477, 1366, 1240, 1102, 930; $\delta_H$ (500 MHz; DMSO-D$_6$) 9.59 (1H, s), 7.83 (1H, d, J 5.0), 7.68 (1H, d, J 3.3), 7.24 (1H, dd, J 5.0, 3.3), 7.03 (1H, t, J 6.3), 6.48-6.15 (2H, br. s), 6.42 (1H, d, J 12.1), 6.37 (1H, dd, J 12.1, 10.6), 5.91 (1H, ddt, J 15.0, 9.9, 5.0), 5.21 (1H, t, J 10.6), 5.10 (1H, d, J 7.6), 5.10 (1H, dd, J 9.9, 1.5), 5.09 (1H, dd, J 15.0, 1.5), 4.82 (1H, d, J 9.5), 4.57 (1H, d, J 4.3), 4.06 (2H, dd, J 6.3, 5.0), 3.81 (1H, dd, J 10.6, 9.5), 3.43 (1H, ddd, J 0.6, 4.3, 2.8), 3.21 (3H, s), 3.01 (3H, s), 2.87 (1H, quintet, J 2.8), 2.64 (1H, dd, J 14.4, 10.3), 2.16 (1H, dd, J 14.4, 4.5), 2.15-2.10 (1H, m), 2.08-2.00 (1H, m), 1.90 (3H, s), 1.23-1.16 (1H, m), 1.13 (3H, s), 0.87 (3H, d, J 6.0), 0.84 (3H, d, J 6.4), 0.82-0.75

(1H, m); $\delta_C$ (125 MHz; DMSO-$D_6$) 182.6 (C), 179.8 (C), 173.8 (C), 155.8 (C), 144.4 (C), 139.5 (C), 139.3 (C), 135.8 (CH), 134.0 (CH), 131.6 (C), 130.9 (CH), 130.6 (CH), 129.2 (CH), 128.6 (C), 128.1 (CH), 127.2 (CH), 121.5 (CH), 121.1 (C), 115.2 ($CH_2$), 110.2 (C), 80.6 (CH), 79.7 (CH), 74.6 (CH), 73.7 (CH), 55.8 ($CH_3$), 55.7 ($CH_3$), 46.0 ($CH_2$), 34.8 (CH), 30.4 ($CH_2$), 30.0 ($CH_2$), 29.9 (CH), 20.8 ($CH_3$), 18.4 ($CH_3$), 14.3 ($CH_3$), 11.4 ($CH_3$); m/z (ESI) 690 ([M+Na]$^+$, 100%).

(4E,6Z,8S,9S,10E,12S,13R,14S,16R)-19-(Allylamino)-13-hydroxy-8,14-dimethoxy-21-(4-methoxyphenyl)-4,10,12,16-tetramethyl-3,20,22-trioxo-2-azabicyclo[16.3.1]docosa-1(21),4,6,10,18-pentaen-9-yl carbamate [19-(4-methoxyphenyl)-AAG]

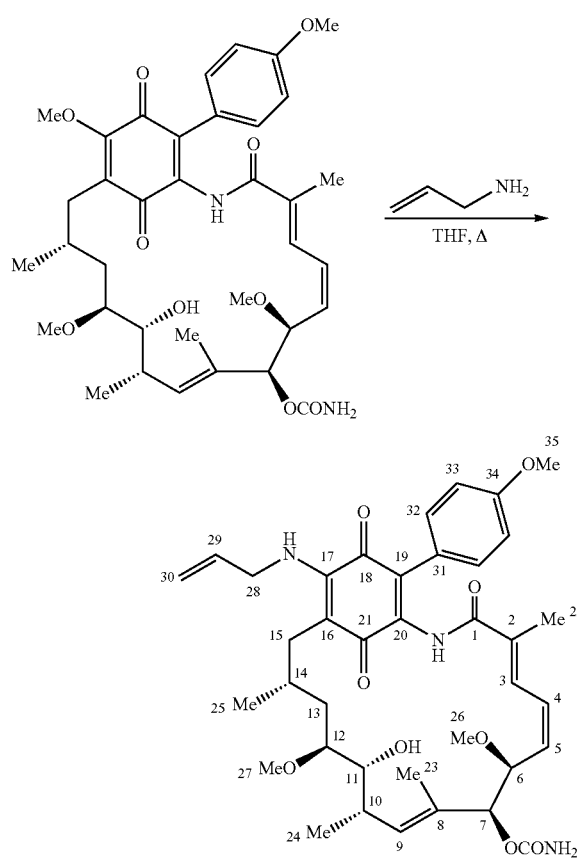

The reaction was carried out according to general procedure 2, using allylamine (0.003 mL, 0.038 mmol, 5 eq.) in THF (1 mL), differing only in that 19-phenylgeldanamycin (5 mg, 0.008 mmol, 1.0 eq.) was used instead of 19-methylgeldanamycin. Purification by flash chromatography on silica gel, eluting with 1:1 light petroleum/ethyl acetate→ethyl acetate gave the title compound (6 mg, quantitative yield) as a deep purple solid; TLC $R_f$=0.40 (ethyl acetate, det: $KMnO_4/\Delta$); mp 165-166° C.; $[\alpha]_D^{23}$+340.5 (c 0.04, $CHCl_3$); (Found: M+Na$^+$, 714.3370. $C_{38}H_{49}N_3O_9$+Na$^+$, requires 714.3361); $\nu_{max}$ ($CHCl_3$)/cm$^{-1}$ 3654, 3256, 3088, 2469, 2251, 2128, 1619, 1585, 1492, 1460, 1368, 1055, 1030, 1011; $\delta_H$ (400 MHz; DMSO-$D_6$) 9.16 (1H, s), 7.30 (2H, d, J 8.8), 7.07 (2H, d, J 8.8), 6.87 (1H, t, J 6.8), 6.54-6.19 (2H, br. s), 6.46 (1H, d, J 11.9), 6.38 (1H, t, J 10.9), 5.91 (1H, ddt, J 15.4, 10.2, 5.0), 5.27 (1H, t, J 10.6), 5.16-5.06 (3H, m), 4.88 (1H, d, J 9.2), 4.53 (1H, d, J 4.4), 4.06 (2H, t, J 5.5), 3.99 (1H, t, J 9.9), 3.82 (3H, s), 3.45 (1H, ddd, J 0.4, 3.5, 2.9), 3.23 (3H, s), 3.11 (3H, s), 2.92 (1H, quintet, J 2.7), 2.66 (1H, dd, J 15.0, 10.0), 2.21-2.06 (3H, m), 1.89 (3H, s), 1.27 (3H, s), 1.24-1.16 (1H, m), 0.91 (3H, d, J 6.0), 0.86 (3H, d, J 6.4), 0.84-0.78 (1H, m); $\delta_C$ (125 MHz; DMSO-$D_6$) 183.1 (C), 180.1 (C), 173.2 (C), 159.0 (C), 155.8 (C), 151.7 (C), 140.1 (C), 136.0 (CH), 134.8 (CH), 132.3 (C), 131.1 (CH), 131.0 (CH), 128.8 (C), 127.9 (CH), 124.1 (C), 123.7 (CH), 120.1 (CH), 115.4 ($CH_2$), 113.7 (CH), 109.5 (C), 80.6 (CH), 79.8 (CH), 75.2 (CH), 73.8 (CH), 56.0 ($CH_3$), 55.7 ($CH_3$), 55.2 ($CH_3$), 45.9 ($CH_2$), 34.8 (CH), 30.4 ($CH_2$), 30.2 ($CH_2$), 30.0 (CH), 21.0 ($CH_3$), 18.3 ($CH_3$), 14.1 ($CH_3$), 11.6 ($CH_3$); m/z (ESI) 714 ([M+Na]$^+$, 100%).

(4E,6Z,8S,9S,10E,12S,13R,14S,16R)-19-(Allylamino)-21-(4-fluorophenyl)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate [19-(4-fluorophenyl)-AAG]

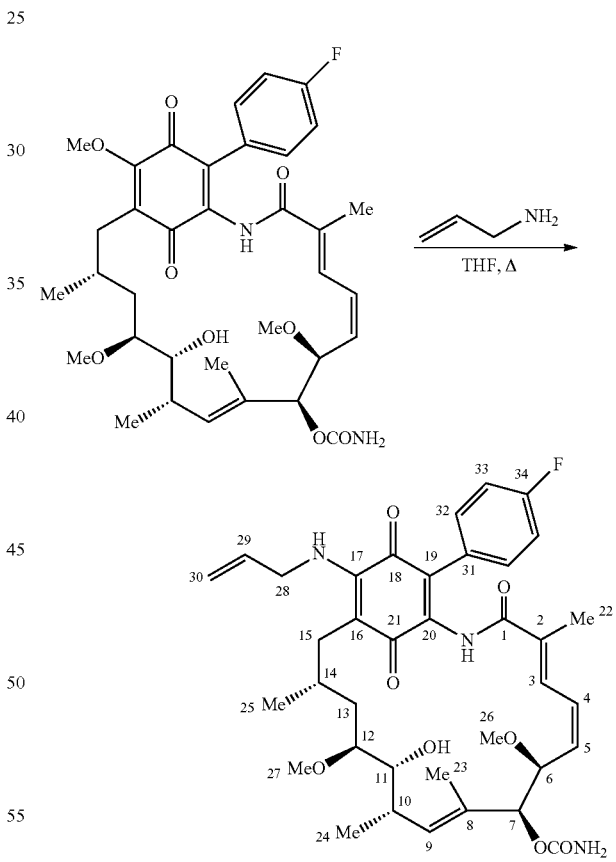

The reaction was carried out according to general procedure 2, using allylamine (0.003 mL, 0.038 mmol, 5 eq.) in THF (1 mL), differing only in that 19-phenylgeldanamycin (5 mg, 0.008 mmol, 1.0 eq.) was used instead of 19-methylgeldanamycin. Purification by flash chromatography on silica gel, eluting with 1:1 light petroleum/ethyl acetate→ethyl acetate gave the title compound (4 mg, 77%) as a purple solid; TLC $R_f$=0.52 (ethyl acetate, det: $KMnO_4/\Delta$); mp 160-161° C.; $[\alpha]_D^{23}$+138.5 (c 0.05, $CHCl_3$); (Found:

M+Na⁺, 702.3174. $C_{37}H_{46}FN_3O_8$+Na⁺, requires 702.3161); $\nu_{max}$ (CHCl₃)/cm⁻¹ 3691, 3012, 2436, 2347, 1727, 1656, 1602, 1581, 1510, 1461, 1240, 1138, 930; $\delta_H$ (500 MHz; DMSO-D₆) 9.36 (1H, s), 7.39 (2H, dd, J 9.0, $J_{H-F}$ 5.9), 7.37 (2H, dd, $J_{H-F}$ 10.0, J 9.0), 6.95 (1H, t, J 6.8), 6.56-6.19 (2H, br. s), 6.45 (1H, d, J 11.9), 6.38 (1H, dd, J 11.9, 10.6), 5.91 (1H, ddt, J 15.3, 10.2, 4.9), 5.28 (1H, t, J 10.6), 5.13 (1H, d, J 9.6), 5.11 (1H, dd, J 15.3, 1.5), 5.09 (1H, dd, J 10.2, 1.5), 4.88 (1H, d, J 9.1), 4.58 (1H, d, J 4.4), 4.08-4.03 (2H, m), 4.00 (1H, dd, J 10.6, 9.1), 3.44 (1H, ddd, J 7.4, 4.4, 2.7), 3.22 (3H, s), 3.11 (3H, s), 2.91 (1H, quintet, J 2.7), 2.65 (1H, dd, J 14.5, 9.8), 2.19-2.08 (3H, m), 1.88 (3H, s), 1.26 (3H, s), 1.23-1.22 (1H, m), 0.91 (3H, d, J 6.1), 0.86 (3H, d, J 6.5), 0.82 (1H, ddd, J 12.3, 6.9, 2.7); $\delta_C$ (125 MHz; DMSO-D₆) 182.8 (C), 179.8 (C), 173.4 (C), 161.8 (d, $J_{C-F}$ 245), 155.9 (C), 144.8 (C), 141.7 (C), 139.4 (C), 136.1 (CH), 133.9 (CH), 132.0 (d, $J_{C-F}$ 8, CH), 130.7 (CH), 128.8 (C), 128.1 (d, $J_{C-F}$ 3, C), 127.9 (CH), 125.5 (C), 121.8 (CH), 115.4 (CH₂), 115.2 (d, $J_{C-F}$ 21, CH), 110.1 (C), 80.7 (CH), 79.8 (CH), 75.3 (CH), 73.7 (CH), 56.0 (CH₃), 55.7 (CH₃), 46.1 (CH₂), 34.8 (CH), 30.5 (CH₂), 30.2 (CH₂), 29.9 (CH), 21.1 (CH₃), 18.3 (CH₃), 14.2 (CH₃), 11.6 (CH₃); $\delta_F$ (376.5 MHz; DMSO-D₆) −113.7; m/z (ESI) 702 ([M+Na]⁺, 100%).

(4E,6Z,8S,9S,10E,12S,13R,14S,16R)-19-(2-(Dimethylamino)ethylamino)-13-hydroxy-8,14-dimethoxy-4,10,12,16,21-pentamethyl-3,20,22-trioxo-2-azabicyclo[16.3.1]docosa-1(21),4,6,10,18-pentaen-9-yl carbamate [19-methyl-DMAG]

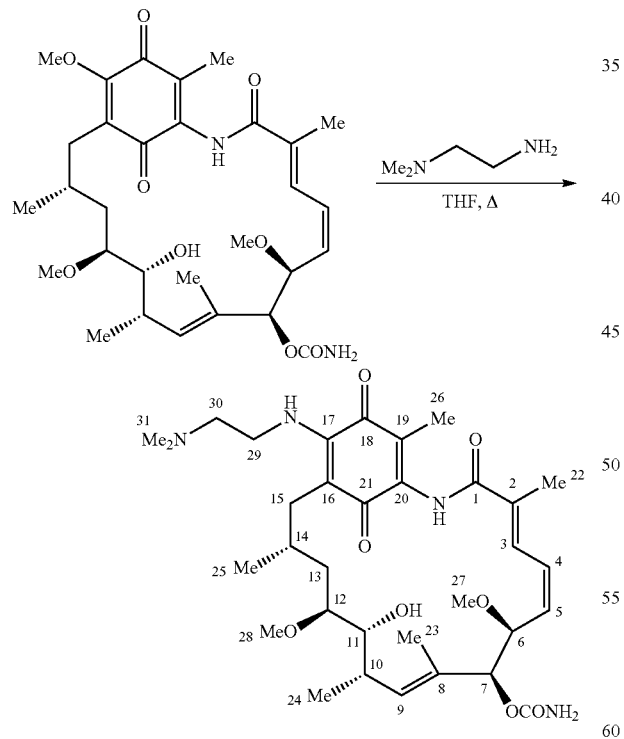

General Procedure 3:

N,N-Dimethylethylenediamine (0.005 mL, 0.044 mmol, 5 eq.) was added to a stirred solution of 19-methylgeldanamycin (4 mg, 0.009 mmol, 1.0 eq.) in THF (1 mL [ca. 0.01 M]) under argon and the mixture was heated to 60° C. for 2 hours [N.B. any further and significant quantities of a bis-adduct are formed]. After cooling, the mixture was concentrated in vacuo and the residue was purified by flash chromatography on silica gel, eluting with 9:1 ethyl acetate/methanol→8:2 ethyl acetate/methanol, to give the title compound (6 mg, quantitative yield) as a purple solid; TLC $R_f$=0.08 (9:1 ethyl acetate/methanol, det: KMnO₄/Δ); mp 139-140° C.; $[\alpha]_D^{23}$+ 178.9 (c 0.04, CHCl₃); (Found: M+H⁺, 631.3706. $C_{33}H_{51}N_4O_8^+$, requires 631.3701); $\nu_{max}$ (CHCl₃)/cm⁻¹ 3513, 3405, 3006, 2439, 2432, 1730, 1696, 1662, 1541, 1460, 1392, 1243, 1108, 1054, 932; $\delta_H$ (400 MHz; DMSO-D₆) 9.39 (1H, s), 6.58 (1H, t, J 5.2), 6.52-6.17 (2H, br. s), 6.32 (1H, dd, J 11.8, 10.8), 6.21 (1H, d, J 11.8), 5.19 (1H, t, J 10.8), 5.09 (1H, dd, J 10.0, 0.6), 4.84 (1H, d, J 9.4), 4.50 (1H, d, J 4.3), 3.94 (1H, dd, J 10.8, 9.4), 3.58-3.50 (1H, m), 3.48-3.40 (1H, m), 3.45-3.41 (2H, m), 3.20 (3H, s), 3.04 (3H, s), 2.89-2.85 (1H, m), 2.62 (1H, ddd, J 15.5, 9.2, 0.5), 2.45-2.37 (2H, m), 2.24 (1H, ddd, J 15.5, 10.5, 1.0), 2.19 (6H, s), 2.15-2.10 (1H, m), 2.07-2.00 (1H, m), 1.96 (3H, s), 1.86 (3H, s), 1.24-1.14 (1H, m), 1.18 (3H, s), 0.85 (3H, d, J 6.5), 0.85 (3H, d, J 6.2), 0.75 (1H, ddd, J 14.8, 2.5, 1.4); $\delta_C$ (125 MHz; DMSO-D₆) 183.9 (C), 180.3 (C), 174.1 (C), 155.9 (C), 144.1 (C), 142.1 (C), 139.1 (C), 135.8 (C), 133.9 (CH), 130.1 (CH), 128.2 (CH), 122.7 (C), 121.9 (CH), 108.7 (C), 80.5 (CH), 79.9 (CH), 74.7 (CH), 73.6 (CH), 57.6 (CH₂), 55.7 (CH₃), 55.5 (CH₃), 44.6 (CH₃), 41.0 (CH₂), 34.8 (CH), 30.7 (CH), 30.2 (CH₂), 29.9 (CH₂), 20.7 (CH₃), 18.4 (CH₃), 14.1 (CH₃), 11.1 (CH₃), 10.4 (CH₃); m/z (ESI) 631 ([M+H]⁺, 100%), 653 ([M+Na]⁺, 43%).

(4E,6Z,8S,9S,10E,12S,13R,14S,16R)-19-(2-(Dimethylamino)ethylamino)-13-hydroxy-8,14-dimethoxy-4,10,12,16-tetramethyl-3,20,22-trioxo-21-phenyl-2-azabicyclo[16.3.1]docosa-1 (21),4,6,10,18-pentaen-9-yl carbamate [19-phenyl-DMAG]

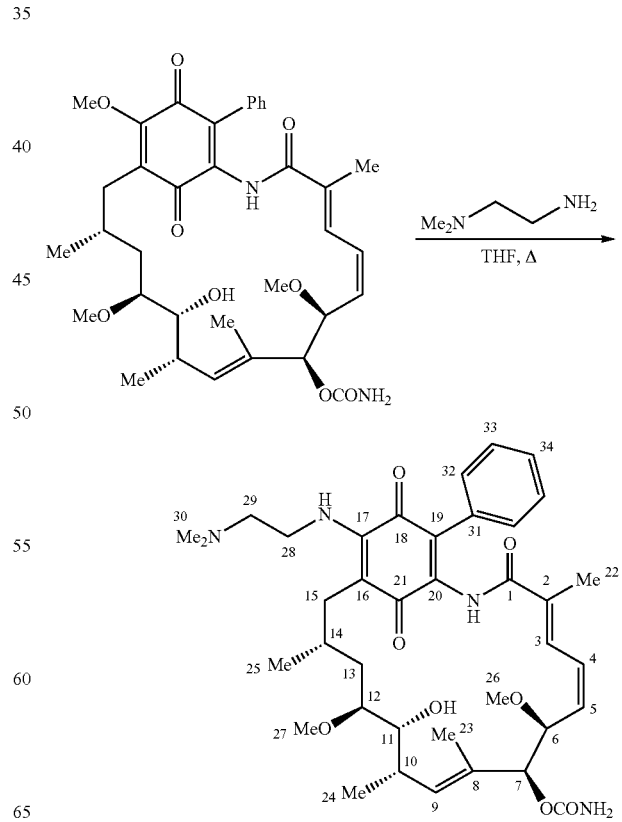

The reaction was carried out according to general procedure 3, using N,N-dimethylethylenediamine (0.014 mL, 0.141 mmol, 5 eq.) in THF (2 mL), differing only in that 19-phenylgeldanamycin (18 mg, 0.028 mmol, 1.0 eq.) was used instead of 19-methylgeldanamycin. Purification by flash chromatography on silica gel, eluting with 9:1 ethyl acetate/methanol gave the title compound (20 mg, quantitative yield) as a purple solid; TLC $R_f$=0.08 (9:1 ethyl acetate/methanol, det: KMnO$_4$/Δ); mp 136-137° C.; $[a]_D^{23}$+ 377.2 (c 0.07, CHCl$_3$); (Found: M+Na$^+$, 715.3681. C$_{38}$H$_{52}$N$_4$O$_8$+Na$^+$, requires 715.3677); $v_{max}$ (CHCl$_3$)/cm$^{-1}$ 3527, 3405, 3003, 2919, 2419, 1743, 1689, 1581, 1473, 1243, 1054, 932; $\delta_H$ (500 MHz; DMSO-D$_6$) 9.30 (1H, s), 7.50 (2H, dd, J 8.3, 7.4), 7.41 (1H, tt, J 7.4, 1.5), 7.35 (2H, dd, J 8.3, 1.5), 6.70 (1H, t, J 4.6), 6.57-6.15 (2H, br. s), 6.47 (1H, d, J 11.8), 6.39 (1H, dd, J 11.8, 10.7), 5.29 (1H, t, J 10.7), 5.14 (1H, d, J 10.3), 4.89 (1H, d, J 9.2), 4.58 (1H, d, J 4.2), 4.00 (1H, dd, J 10.7, 9.2), 3.59-3.51 (2H, m), 3.46 (1H, ddd, J 9.6, 4.2, 2.9), 3.23 (3H, s), 3.11 (3H, s), 2.91 (1H, quintet, J 2.9), 2.70 (1H, dd, J 14.2, 8.9), 2.46-2.39 (2H, m), 2.27 (1H, dd, J 14.2, 4.7), 2.19 (6H, s), 2.13-2.05 (2H, m), 1.88 (3H, s), 1.27 (3H, s), 1.26-1.21 (1H, m), 0.90 (3H, d, J 6.3), 0.86 (3H, d, J 6.5), 0.82-0.78 (1H, m); $\delta_C$ (125 MHz; DMSO-D$_6$) 186.5 (C), 179.9 (C), 175.0 (C), 155.9 (C), 144.6 (C), 142.9 (C), 139.8 (C), 133.8 (CH), 131.6 (C), 130.6 (CH), 129.7 (CH), 128.7 (C), 128.2 (CH), 128.1 (CH), 128.1 (CH), 121.7 (CH), 114.9 (C), 109.3 (C), 80.6 (CH), 79.8 (CH), 75.1 (CH), 73.5 (CH), 57.7 (CH$_2$), 56.0 (CH$_3$), 55.7 (CH$_3$), 44.6 (CH$_3$), 41.3 (CH$_2$), 34.9 (CH), 30.3 (CH), 30.2 (CH$_2$), 30.1 (CH$_2$), 20.8 (CH$_3$), 18.3 (CH$_3$), 14.2 (CH$_3$), 11.6 (CH$_3$); m/z (ESI) 715 ([M+Na]$^+$, 100%).

(4E,6Z,8S,9S,10E,12S,13R,14S,16R)-19-(2-(Dimethylamino)ethylamino)-21-(furan-2-yl)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate [19-(furan-2-yl)-DMAG]

The reaction was carried out according to general procedure 3, using N,N-dimethylethylenediamine (0.018 mL, 0.141 mmol, 5 eq.) in THF (2 mL), differing only in that 19-(furan-2-yl)-geldanamycin (21 mg, 0.034 mmol, 1.0 eq.) was used instead of 19-methylgeldanamycin and the mixture was stirred at room temperature for 16 h to avoid double addition. Purification by flash chromatography on silica gel, eluting with 9:1 ethyl acetate/methanol gave the title compound (19 mg, 83%) as a dark green solid; TLC $R_f$=0.22 (4:1 ethyl acetate/methanol, det: KMnO$_4$/Δ); mp 134-135° C.; $[a]_D^{23}$+97.0 (c 0.03, CHCl$_3$); (Found: M+H$^+$, 683.3651. C$_{36}$H$_{51}$N$_4$O$_9^+$, requires 683.3651); $v_{max}$ (CHCl$_3$)/cm$^{-1}$ 3549, 3417, 2957, 2928, 2855, 2360, 2338, 1787, 1738, 1678, 1478, 1378, 1184, 1007; $\delta_H$ (500 MHz; DMSO-D$_6$) 9.63 (1H, s), 7.93 (1H, dd, J 1.8, 0.7), 7.07 (1H, dd, J 3.5, 0.7), 6.75 (1H, t, J 4.9), 6.69 (1H, dd, J 3.5, 1.8), 6.51-6.19 (2H, br. s), 6.46 (1H, d, J 11.9), 6.36 (1H, dd, J 11.9, 10.7), 5.20 (1H, t, J 10.7), 5.09 (1H, dd, J 10.1, 1.0), 4.82 (1H, d, J 9.4), 4.56 (1H, d, J 4.3), 3.75 (1H, dd, J 10.7, 9.4), 3.57 (1H, dddd, J 19.0, 6.4, 5.3, 4.9), 3.48 (1H, dddd, J 19.0, 11.2, 6.2, 4.9), 3.43 (1H, ddd, J 10.0, 4.3, 2.6), 3.21 (3H, s), 3.00 (3H, s), 2.87 (1H, quintet, J 2.6), 2.67 (1H, dd, J 14.4, 8.9), 2.54 (1H, ddd, J 18.8, 6.4, 6.2), 2.44 (1H, ddd, J 18.8, 11.2, 5.3), 2.27 (1H, dd, J 14.4, 4.6), 2.20 (6H, s), 2.17-2.09 (1H, m), 2.05 (1H, ddtd, J 10.2, 8.9, 6.5, 4.6), 1.89 (3H, d, J 1.0), 1.23-1.19 (1H, m), 1.13 (3H, s), 0.86 (3H, d, J 6.5), 0.84 (3H, d, J 6.6), 0.77 (1H, ddd, J 14.1, 10.2, 2.7); $\delta_C$ (125 MHz; DMSO-D$_6$) 181.3 (C), 179.6 (C), 173.8 (C), 155.8 (C), 145.5 (C), 144.3 (CH), 144.0 (C), 139.9 (C), 139.0 (C), 133.9 (CH), 130.5 (CH), 128.6 (C), 128.2 (CH), 122.3 (CH), 115.3 (C), 114.8 (CH), 111.9 (CH), 109.2 (C), 80.5 (CH), 79.7 (CH), 74.6 (CH), 73.5 (CH), 57.8 (CH$_2$), 55.5 (CH$_3$), 55.5 (CH$_3$), 44.6 (CH$_3$), 41.2 (CH$_2$), 34.9 (CH), 30.4 (CH), 30.3 (CH$_2$), 29.9 (CH$_2$), 20.6 (CH$_3$), 18.3 (CH$_3$), 14.2 (CH$_3$), 11.2 (CH$_3$); m/z (ESI) 683 ([M+H]$^+$, 100%).

(4E,6Z,8S,9S,10E,12S,13R,14S,16R)-19-(2-(Dimethylamino)ethylamino)-13-hydroxy-8,14-dimethoxy-21-(4-methoxyphenyl)-4,10,12,16-tetramethyl-3,20,22-trioxo-2-azabicyclo[16.3.1]docosa-1(21),4,6,10,18-pentaen-9-yl carbamate [19-(4-methoxyphenyl)-DMAG]

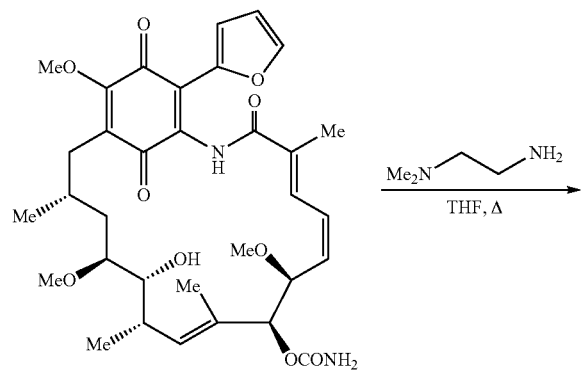

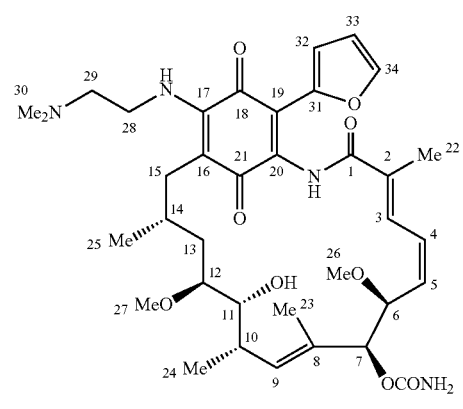

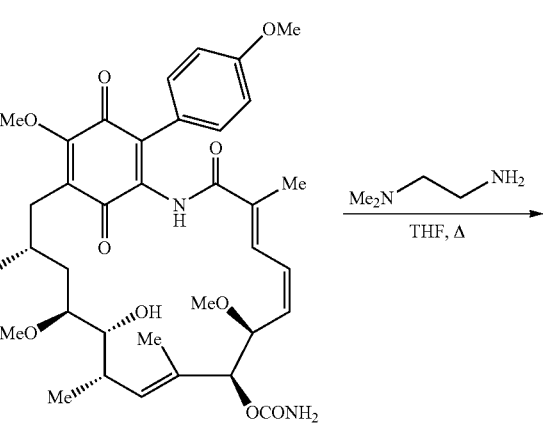

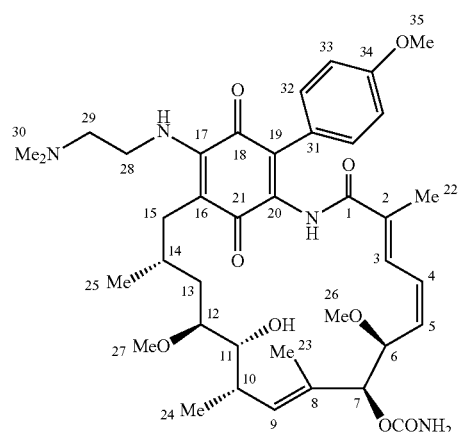

The reaction was carried out according to general procedure 3, using N,N-dimethylethylenediamine (0.009 mL, 0.082 mmol, 5 eq.) in THF (1 mL), differing only in that 19-(4-methoxyphenyl)-geldanamycin (11 mg, 0.017 mmol, 1.0 eq.) was used instead of 19-methylgeldanamycin. Purification by flash chromatography on silica gel, eluting with 9:1 ethyl acetate/methanol gave the title compound (20 mg, quantitative yield) as a purple solid; TLC $R_f$=0.14 (9:1 ethyl acetate/methanol, det: KMnO$_4$/Δ); mp 144-146° C.; $[a]_D^{23}$+ 487.5 (c 0.03, CHCl$_3$); (Found: M+Na$^+$, 745.3780. C$_{39}$H$_{54}$N$_4$O$_9$+Na$^+$, requires 745.3783); $v_{max}$ (CHCl$_3$)/cm$^{-1}$ 3660, 3257, 3090, 2469, 2251, 2128, 1618, 1581, 1491, 1461, 1369, 1241, 1054, 1030, 1011, 878; $\delta_H$ (400 MHz; DMSO-D$_6$) 9.64-8.95 (1H, br. s), 7.31 (2H, d, J 8.8), 7.03 (2H, d, J 8.8), 6.83-6.73 (1H, m), 6.57-6.15 (2H, br. s), 6.44 (1H, d, J 8.8), 6.38 (1H, dd, J 12.0, 10.5), 5.24 (1H, t, J 10.5), 5.11 (1H, d, J 10.2), 4.87 (1H, d, J 9.3), 4.50 (1H, d, J 4.0), 3.98 (1H, dd, J 10.5, 9.3), 3.81 (3H, s), 3.57-3.50 (2H, m), 3.45-3.41 (2H, m), 3.22 (3H), 3.10 (3H, s), 2.91 (1H, quintet, J 2.8), 2.68 (1H, dd, J 14.2, 9.2), 2.52 (1H, dt, J 11.7, 6.3), 2.41 (1H, dt, J 11.7, 5.6), 2.25 (1H, ddd, J 14.2, 5.2), 2.18 (6H, s), 2.14-2.07 (2H, m), 1.88 (3H, s), 1.27 (3H, s), 1.23-1.19 (1H, m), 0.90 (3H, d, J 6.3), 0.85 (3H, d, J 6.5), 0.84-0.78 (1H, m); $\delta_C$ (125 MHz; DMSO-D$_6$) 179.9 (C), 179.9 (C), 172.2 (C), 158.7 (C), 155.9 (C), 145.1 (C), 140.1 (C), 133.8 (CH), 132.1 (C), 131.2 (CH), 130.1 (CH), 128.9 (C), 128.3 (CH), 124.5 (CH), 121.4 (CH), 118.4 (CH), 113.5 (CH), 108.6 (C), 80.7 (CH), 79.8 (CH), 75.1 (CH), 73.7 (CH), 57.8 (CH$_2$), 56.0 (CH$_3$), 55.7 (CH$_3$), 55.2 (CH$_3$), 44.7 (CH$_3$), 41.2 (CH$_2$), 34.9 (CH), 30.8 (CH), 30.4 (CH$_2$), 30.0 (CH$_2$), 20.9 (CH$_3$), 18.3 (CH$_3$), 14.3 (CH$_3$), 11.5 (CH$_3$); m/z (ESI) 723 ([M+H]$^+$, 100%), 745 ([M+Na]$^+$, 23%).

(4E,6Z,8S,9S,10E,12S,13R,14S,16R)-19-(2-(Dimethylamino)ethylamino)-21-(4-fluorophenyl)-13-hydroxy-8,14-dimethoxy-4,10,12,16-tetramethyl-3,20,22-trioxo-2-azabicyclo[16.3.1]docosa-1(21),4,6,10,18-pentaen-9-yl carbamate [19-(4-fluorophenyl)-DMAG]

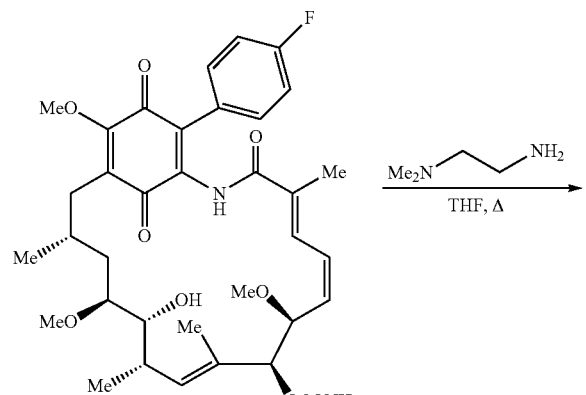

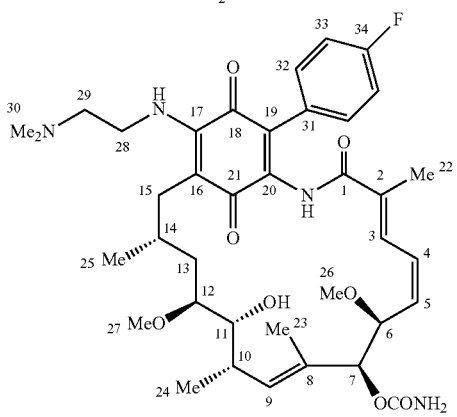

The reaction was carried out according to general procedure 3, using N,N-dimethylethylenediamine (0.009 mL, 0.084 mmol, 5 eq.) in THF (1 mL), differing only in that 19-(4-fluorophenyl)-geldanamycin (11 mg, 0.017 mmol, 1.0 eq.) was used instead of 19-methylgeldanamycin. Purification by flash chromatography on silica gel, eluting with 9:1 ethyl acetate/methanol gave the title compound (9 mg, 75%) as a purple solid; TLC $R_f$=0.17 (9:1 ethyl acetate/methanol, det: KMnO$_4$/Δ); mp 145-146° C.; $[a]_D^{23}$+588.6 (c 0.04, CHCl$_3$); (Found: M+H$^+$, 711.3745. C$_{38}$H$_{52}$FN$_4$O$_9^+$, requires 711.3764); $v_{max}$ (CHCl$_3$)/cm$^{-1}$ 3666, 3426, 3084, 2469, 2251, 2127, 1619, 1495, 1460, 1370, 1241, 1060, 1037, 1011, 919; $\delta_H$ (500 MHz; DMSO-D$_6$) 9.39 (1H, br. s), 7.39 (2H, dd, J 8.9, J$_{H-F}$ 5.8), 7.34 (2H, dd, J$_{H-F}$ 8.9, J 8.9), 6.73 (1H, t, J 4.5), 6.57-6.17 (2H, br. s), 6.45 (1H, d, J 11.9), 6.39 (1H, dd, J 11.9, 10.6), 5.28 (1H, t, J 10.6), 5.14 (1H, d, J 10.0), 4.88 (1H, d, J 9.1), 4.57 (1H, d, J 4.3), 3.99 (1H, dd, J 10.6, 9.1), 3.56 (2H, td, J 8.2, 4.5), 3.45 (1H, ddd, J 9.8, 4.3, 2.8), 3.22 (3H, s), 3.11 (3H, s), 2.91 (1H, quintet, J 2.8), 2.69 (1H, dd, J 14.2, 9.0), 2.54-2.50 (1H, m), 2.43 (1H, dt, J 11.5, 8.2), 2.26 (1H, dd, J 14.2, 4.7), 2.19 (6H, s), 2.16-2.04 (2H, m), 1.88 (3H, s), 1.26 (3H, s), 1.26-1.21 (1H, m), 0.90 (3H, d, J 6.3), 0.85 (3H, d, J 6.5), 0.84-0.80 (1H, m); $\delta_C$ (125 MHz; DMSO-D$_6$) 182.3 (C), 179.8 (C), 173.6 (C), 161.7 (d, J$_{C-F}$ 245), 155.9 (C), 144.7 (C), 139.6 (C), 133.8 (CH), 132.0

(d, $J_{C-F}$ 8, CH), 130.6 (CH), 128.8 (C), 128.1 (CH), 128.1 (d, $J_{C-F}$ 4, C), 124.8 (C), 121.9 (CH), 116.5 (C), 115.2 (d, $J_{C-F}$ 22, CH), 109.2 (C), 80.6 (CH), 79.8 (CH), 75.2 (CH), 73.6 (CH), 57.7 (CH$_2$), 56.0 (CH$_3$), 55.7 (CH$_3$), 44.6 (CH$_3$), 41.3 (CH$_2$), 34.9 (CH), 30.5 (CH), 30.4 (CH$_2$), 30.1 (CH$_2$), 20.9 (CH$_3$), 18.3 (CH$_3$), 14.2 (CH$_3$), 11.5 (CH$_3$); $\delta_F$ (376.5 MHz; DMSO-D$_6$) −113.8; m/z (ESI) 711 ([M+H]$^+$, 100%), 733 ([M+Na]$^+$, 25%).

(R)-Methyl-2-acetamido-3-((4E,6Z,8S,9S,10E,12S, 13R,14S,16R)-9-(carbamoyloxy)-13-hydroxy-8,14, 19-trimethoxy-4,10,12,16-tetramethyl-3,20,22-tri-oxo-2-azabicyclo[16.3.1]docosa-1(21),4,6,10,18-pentaen-21-ylthio)propanoate

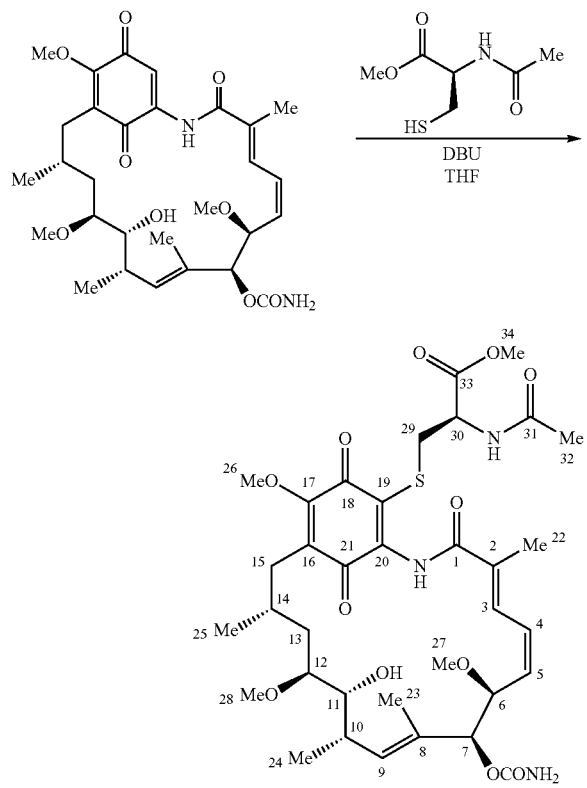

1,8-Diazabicycloundec-7-ene (0.014 mL, 0.091 mmol, 1.25 eq.) was added to a stirred solution of geldanamycin (41 mg, 0.073 mmol, 1.0 eq.) and N-acetylcysteine methyl ester (16 mg, 0.088 mmol, 1.2 eq.) in THF (3 mL) at room temperature. After stirring the resulting solution for 2 h, the reaction was quenched with excess acetic acid and concentrated in vacuo. The residue was purified by flash chromatography on silica gel, eluting with 1:1 light petroleum/ethyl acetate→ethyl acetate to give the title compound (19 mg, 35%) as a dark orange solid; TLC $R_f$=0.15 (ethyl acetate, det: KMnO$_4$/Δ); mp 151-152° C.; [a]$_D^{23}$+44.0 (c 0.07, CHCl$_3$); (Found: M+Na$^+$, 758.2927. C$_{35}$H$_{49}$N$_3$O$_{12}$S+Na$^+$, requires 758.2929); $\nu_{max}$ (CHCl$_3$)/cm$^{-1}$ 3544, 3010, 2879, 2298, 1732, 1676, 1592, 1487, 1456, 1370, 1103, 1044, 1033, 1018, 968; $\delta_H$ (500 MHz; DMSO-D$_6$) 9.51 (1H, s), 8.62 (1H, d, J 8.2), 6.42-6.18 (2H, m), 6.35 (1H, dd, J 11.8, 10.7), 6.24 (1H, d, J 11.8), 5.26 (1H, t, J 10.7), 5.16 (1H, d, J 10.3), 4.86 (1H, d, J 9.0), 4.67 (1H, td, J 8.2, 4.5), 4.41 (1H, br. s), 3.95 (3H, s), 3.91 (1H, dd, J 10.7, 9.0), 3.64 (3H, s), 3.49 (1H, dd, J 13.4, 4.5), 3.46-3.44 (1H, m), 3.24 (1H, dd, J 13.4, 8.2), 3.18 (3H, s), 3.02 (3H, s), 2.78 (1H, dt, J 8.8, 2.6), 2.46 (1H, dd, J 12.5, 5.9), 2.35 (1H, dd, J 12.5, 4.5), 2.10-2.01 (2H, m), 1.88 (3H, s), 1.84 (3H, s), 1.38 (1H, ddd, J 13.8, 8.8, 4.0), 1.21 (3H, s), 0.88 (3H, d, J 6.5), 0.64 (1H, td, J 13.8, 2.6), 0.59 (3H, d, J 6.7); $\delta_C$ (125 MHz; DMSO-D$_6$) 181.9 (C), 178.4 (C), 172.9 (C), 170.8 (C), 169.9 (C), 157.6 (C), 155.9 (C), 143.6 (C), 138.6 (C), 134.3 (CH), 130.6 (CH), 128.7 (C), 128.6 (C), 128.3 (CH), 126.8 (C), 123.3 (CH), 79.9 (CH), 79.6 (CH), 74.7 (CH), 71.5 (CH), 61.0 (CH$_3$), 55.7 (CH$_3$), 55.5 (CH$_3$), 52.3 (CH$_3$), 52.3 (CH), 34.8 (CH), 34.3 (CH$_2$), 30.6 (CH$_2$), 29.7 (CH$_2$), 28.6 (CH), 22.4 (CH$_3$), 19.0 (CH$_3$), 18.6 (CH$_3$), 13.9 (CH$_3$), 11.6 (CH$_3$); m/z (ESI) 758 ([M+Na]$^+$, 100%).

(R)-Methyl-2-acetamido-3-((4E,6Z,8S,9S,10E,12S, 13R,14S,16R)-19-(allylamino)-9-(carbamoyloxy)-13-hydroxy-8,14-dimethoxy-4,10,12,16-tetramethyl-3,20,22-trioxo-2-azabicyclo[16.3.1]docosa-1(21),4, 6,10,18-pentaen-21-ylthio)propanoate

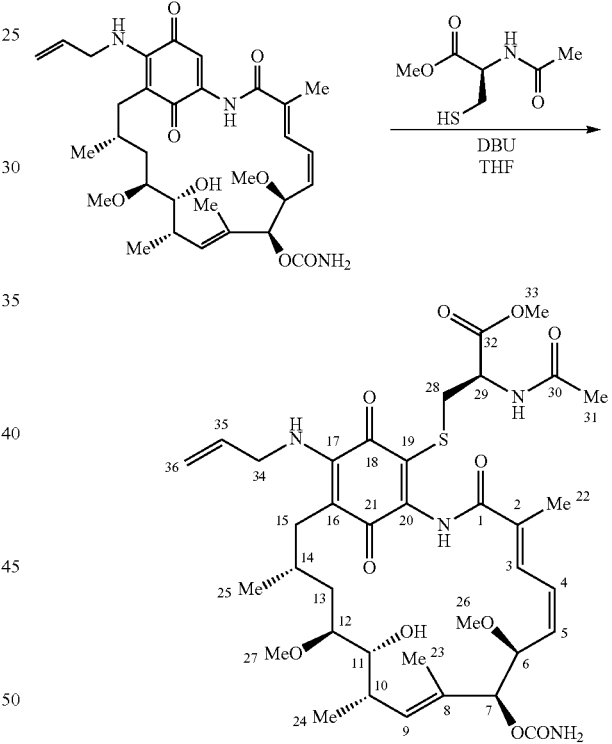

1,8-Diazabicycloundec-7-ene (0.015 mL, 0.098 mmol, 1.25 eq.) was added to a stirred solution of 17-allylamino (demethoxy)geldanamycin (46 mg, 0.079 mmol, 1.0 eq.) and N-acetylcysteine methyl ester (17 mg, 0.094 mmol, 1.2 eq.) in THF (3 mL) at room temperature. After stirring the resulting solution for 2 h, the reaction was quenched with excess acetic acid and concentrated in vacuo. The residue was purified by flash chromatography on silica gel, eluting with 1:1 light petroleum/ethyl acetate→9:1 ethyl acetate/methanol to give the title compound (37 mg, 62%) as a brown solid; TLC $R_f$=0.15 (ethyl acetate, det: KMnO$_4$/Δ); mp 156-158° C.; [a]$_D^{23}$+59.7 (c 0.07, CHCl$_3$); (Found: M+Na$^+$, 783.3232. C$_{37}$H$_{52}$N$_4$O$_{11}$S+Na$^+$, requires 783.3246); $\nu_{max}$ (CHCl$_3$)/cm$^{-1}$ 3298, 3240, 3063, 3009, 2305, 2195, 2116, 1939, 1732, 1676, 1582, 1454, 1372, 1127, 1044, 1034, 1018, 964; $\delta_H$ (500 MHz; DMSO-D$_6$) 9.31 (1H, s), 8.61 (1H, d, J 8.1), 7.10 (1H, t, J 6.8), 6.70-6.21 (2H, m), 6.33 (1H, dd, J 11.6, 10.8), 6.17 (1H, d, J 11.6), 5.90 (1H, ddt, J 15.2, 10.1, 4.9), 5.23 (1H, t, J 10.8), 5.10 (1H, dd, J 15.2, 1.5), 5.09 (1H, dd, J 10.1, 1.5), 5.09 (1H, d, J 10.3), 4.85 (1H, d, J 9.2), 4.62 (1H, td, J 8.1, 4.6), 4.57 (1H, d, J 4.3), 4.08-4.02 (2H, m), 3.90 (1H, dd, J 10.8, 9.2), 3.62 (3H, s), 3.44-3.40 (1H, m), 3.38 (1H, dd, J 13.4, 4.6), 3.20 (3H, s), 3.14 (1H, dd, J 13.4, 8.1), 3.02 (3H, s), 2.89-2.85 (1H, m), 2.56 (1H, dd, J 15.2, 10.3), 2.15-2.09 (3H, m), 1.88 (3H, s), 1.88 (3H, s), 1.21 (3H, s), 1.14-1.10 (1H, m), 0.87 (3H, d, J 5.9), 0.86 (3H, d, J 6.4), 0.79-0.73 (1H, m); $\delta_C$ (125 MHz; DMSO-D$_6$) 180.2 (C), 178.0 (C), 173.5 (C), 170.9 (C), 169.8 (C), 155.9 (C), 145.7 (C), 139.5 (C), 135.8 (CH), 135.2 (C), 133.9 (CH), 130.8 (CH), 128.8 (C), 128.0 (CH), 122.2 (CH), 120.4 (C), 115.5 (CH$_2$), 110.0 (C), 80.7 (CH), 79.8 (CH), 74.9 (CH), 73.8 (CH), 55.7 (CH$_3$), 55.6 (CH$_3$), 52.3 (CH), 52.2 (CH$_3$), 46.1 (CH$_2$), 34.7 (CH), 34.4 (CH$_2$), 30.4 (CH$_2$), 30.1 (CH$_2$), 29.8 (CH), 22.4 (CH$_3$), 21.0 (CH$_3$), 18.3 (CH$_3$), 14.2 (CH$_3$), 11.9 (CH$_3$); m/z (ESI) 783 ([M+Na]$^+$, 100%).

(R)-Methyl-2-acetamido-3-((4E,6Z,8S,9S,10E,12S,13R,14S,16R)-9-(carbamoyloxy)-19-(2-(dimethylamino)ethylamino)-13-hydroxy-8,14-dimethoxy-4,10,12,16-tetramethyl-3,20,22-trioxo-2-azabicyclo[16.3.1]docosa-1(21),4,6,10,18-pentaen-21-ylthio)propanoate

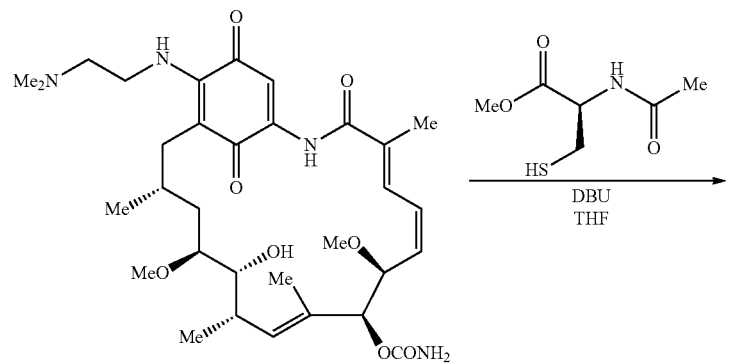

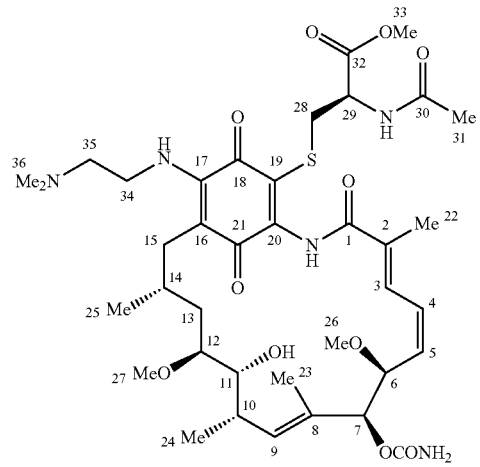

1,8-Diazabicycloundec-7-ene (0.031 mL, 0.207 mmol, 2.3 eq.) was added to a stirred solution of 17-(2-(dimethylamino)ethylamino)(demethoxy)geldanamycin hydrochloride (108 mg, 0.165 mmol, 1.0 eq.) and N-acetylcysteine methyl ester (35 mg, 0.198 mmol, 1.2 eq.) in THF (5 mL) at room temperature. After stirring the resulting solution for 2 d, the reaction was quenched with excess acetic acid and concentrated in vacuo. The residue was purified by flash chromatography on silica gel, eluting with ethyl acetate→1:1 ethyl acetate/methanol to give the title compound (27 mg, 21%) as a purple solid; TLC $R_f$=0.07 (9:1 ethyl acetate/methanol, det: $KMnO_4/\Delta$); mp 166-168° C.; $[a]_D^{23}$+30.5 (c 0.07, $CHCl_3$); (Found: M+Na$^+$, 792.3863. $C_{38}H_{58}N_5O_{11}S+H^+$, requires 792.3848); $v_{max}$ ($CHCl_3$)/cm$^{-1}$ 3662, 3256, 3088, 3012, 3002, 2469, 2251, 2127, 1729, 1620, 1586, 1494, 1457, 1370, 1241, 1058, 1052, 1030, 1011, 878; $\delta_H$ (500 MHz; DMSO-$D_6$) 9.92 (1H, s), 8.83-8.70 (1H, m), 7.06-6.90 (1H, m), 6.64-6.46 (2H, m), 6.33 (1H, dd, J 11.7, 10.4), 6.18 (1H, d, J 11.7), 5.20 (1H, t, J 10.4), 5.08 (1H, d, J 10.2), 4.83 (1H, d, J 9.3), 4.62 (1H, td, J 7.6, 4.8), 4.57 (1H, d, J 4.2), 3.88 (1H, dd, J 10.4, 9.3), 3.63 (3H, s), 3.58-3.53 (1H, m), 3.47 (1H, m), 3.43-3.38 (1H, m), 3.25-3.22 (1H, m), 3.19 (3H, s), 3.16-3.13 (2H, m), 3.02 (3H, s), 2.86 (1H, quintet, J 2.6), 2.70-2.68 (1H, m), 2.58 (1H, dd, J 14.2, 9.0), 2.31 (6H, s), 2.21 (1H, dd, J 14.2, 4.6), 2.11-2.02 (2H, m), 1.89 (3H, s), 1.88 (3H, s), 1.21 (3H, s), 1.15-1.09 (1H, m), 0.86 (3H, d, J 6.1), 0.85 (3H, d, J 6.4), 0.76 (1H, ddd, J 13.4, 9.0, 2.6); $\delta_C$ (125 MHz; DMSO-$D_6$) 178.0 (C), 178.0 (C), 170.9 (C), 170.4 (C), 169.9 (C), 165.4 (C), 155.9 (C), 139.9 (C), 133.8 (CH), 131.3 (C), 130.5 (CH), 128.8 (C), 128.7 (C), 128.2 (CH), 122.2 (CH), 110.2 (C), 80.7 (CH), 79.8 (CH), 74.9 (CH), 73.8 (CH), 55.7 ($CH_3$), 55.7 ($CH_3$), 53.4 ($CH_2$), 52.2 (CH), 52.1 ($CH_3$), 47.9 ($CH_2$), 44.2 ($CH_3$), 37.5 ($CH_2$), 34.8 (CH), 30.4 ($CH_2$), 30.3 (CH), 29.9 ($CH_2$), 22.4 ($CH_3$), 20.8 ($CH_3$), 18.3 ($CH_3$), 14.3 ($CH_3$), 11.5 ($CH_3$); m/z (ESI) 792 ([M+H]$^+$, 100%).

Example 5

Therapeutic Activity of 19-Substituted Benzoquinones

In vitro testing was performed to verify that 19-substitutions prevent GSH conjugation of benzoquinone ansamycins (BQAs). Referring to FIG. 6, reactions were performed in 50 mM potassium phosphate buffer, pH 7.4 containing 50 µM benzoquinone ansamycin in the absence (solid bars) and presence (hatched bars) of 5 mM GSH. At the indicated times (GM series, 15 min; DMAG series, 3 hr; AAG series, 16 hr) the reactions were stopped and BQA concentrations were determined by HPLC. Results are the mean of three separate determinations ±standard deviations.*p<0.01, significantly different from minus GSH. The results demonstrate that the 19-substituted BQAs do not react with glutathione and, as a result, would be expected to be less hepatotoxic. The 19-substituted benzoquinone ansamycins were also tested in vitro for inhibition of Hsp90. Referring to FIG. 7, purified recombinant yeast Hsp90 ATPase activity was measured in reactions with 19-substituted BQAs in the absence and presence of NADPH quinone oxidoreductase 1 (NQO1). Results are expressed as percent of DMSO control (mean±SD n=3). Panel A shows 19Ph- and 19Me-AAG (50 µM); 19Ph- and 19Me-GM (10 µM) *p<0.05, significantly different from DMSO control. Panel B shows yeast Hsp90 ATPase activity after treatment with 19Me-GM (2-10 µM) in the absence and presence of NQO1. *p<0.05, significantly different from minus NQO1. These data demonstrate directly that 19-substitution does not preclude the ability of the compounds described in this invention to inhibit Hsp90.

The 19-substituted benzoquinone ansamycins were also tested in vitro for their ability to induce Hsp70 and Hsp27. Referring to FIG. 8, Hsp70 and Hsp27 protein levels were measured in SH-SY5Y cells by immunoblot analysis following treatment with BQAs for 16 hr. Panel A, Hsp70; panel B, Hsp27. Induction of Hsp levels is the proposed mechanism of protection against neurodegenerative diseases.

The 19-substituted benzoquinone ansamycins were also tested in vitro for their ability to reduce the toxicity of BQAs to SH-SY5Y cells a dopaminergic model system of relevance to neurodegenerative disease. Referring to FIG. 9, toxicity of BQAs in SH-SY-5Y cells was measured using trypan blue exclusion (panel A), MTT growth inhibition assay (panel B) and annexin V/PI staining for apoptosis (panel C). Cells in A and C were treated with BQAs (5 µM) for 16 h; cells in B were treated with BQAs for 4 h then allowed to grow in drug-free medium for 72 h. Results are expressed as the mean±SEM of 3 independent determinations. *p<0.05 significantly different from control. The 19-substituted BQAs do not induce growth inhibition or toxicity in SHSY-5Y neural cells while at the same time inducing Hsp protein expression (FIG. 8). The combination of these two properties are likely to be important to the neuroprotective properties of the 19-substituted BQAs.

The 19-substituted benzoquinone ansamycins were also tested in vitro for their ability to inhibit growth similar to DMAG in human breast cancer cells (FIG. 10). MDA468/NQ16 breast cancer cells were treated with 19-substituted DMAG analogs for 4 hours, after which drug-containing media was removed and cells were allowed to grow for an additional 72 h. Cell viability was determined using the MTT assay. Results represent 3 independent determinations ±SD, n=3.19-phenyl DMAG had greater potency at killing breast cancer cells than DMAG suggesting these compounds may be useful as anticancer agents.

Example 6

Efficacy and Toxicity Testing of Compounds of the Invention

The use of geldanamycin, 17-AAG or 17-DMAG induce multiple Hsp's and protect against protein aggregation and toxicity in cell or animal models of multiple neurodegenerative diseases demonstrates significant blood brain barrier penetration and therapeutic potential. These include protection against the toxicity of mutant forms of Cu/Zn SOD which occurs in about 20% of cases of familial ALS, increased Hsp activity in the spinal cord and protection against neurodegeneration in mouse models of spinal and bulbar muscular atrophy (SBMA), protection against htt aggregation and toxicity in a mouse model of Huntington's disease, protection against poly Q disease induced neurodegeneration and Tau aggregation in models of Alzheimer's disease. With respect to Parkinson's disease, geldanamycin or 17-AAG have been shown to prevent α-synuclein aggregation and toxicity in a cellular model, protect against α-synuclein toxicity in fly and yeast models and protect against MPTP induced dopaminergic toxicity in a mouse model of PD. Despite their clinical use, hepatotoxicity remains an issue with both 17-AAG and 17-DMAG. Thus, Hsp90 inhibitors represent an exciting opportunity for induction of Hsps in diseases characterized by protein misfolding but their therapeutic window is too narrow and less toxic agents need to be developed. This is particularly relevant if the Hsp90 inhibitors are employed as neuroprotective agents where any effective drugs may need to be administered for long periods.

To design less toxic BQA Hsp90 inhibitors the inventors proceeded to block their ability to undergo thiol conjugation by synthesizing 19-substituted derivatives in the geldanamycin, AAG and DMAG series. Substitutions at the 19-position (R) include methyl (Me) and phenyl (Ph).

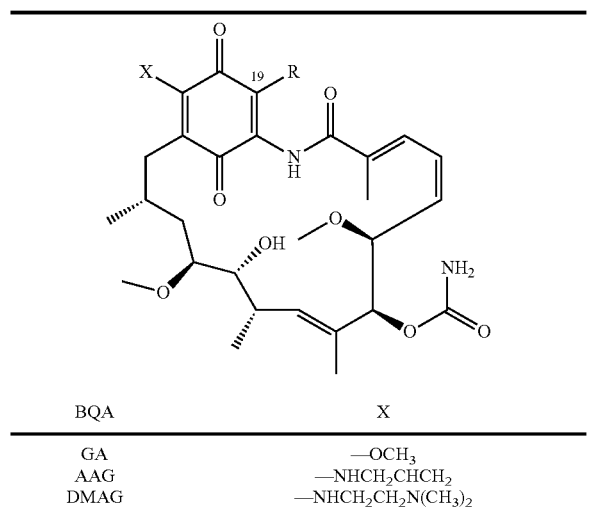

| BQA | X |
|---|---|
| GA | —OCH₃ |
| AAG | —NHCH₂CHCH₂ |
| DMAG | —NHCH₂CH₂N(CH₃)₂ |

These 19-Methyl and phenyl BQA's were tested for their ability to react with thiols (FIG. 6). Reactions were performed in 50 mM potassium phosphate buffer, pH 7.4 containing 50 µM benzoquinone ansamycin in the absence (solid bars) and presence (hatched bars) of 5 mM GSH. At the indicated times (GA series, 15 min; DMAG series, 3 hr; AAG series, 16 hr) the reactions were stopped and BQA concentrations were determined by HPLC. Results are the mean of three separate determinations ±standard deviations (*p<0.01, significantly different from minus GSH). These results demonstrate that these compounds are incapable of reacting with thiols at the 19-position, thereby validating the rationale for their synthesis.

The inventors next compared the relative rates of redox cycling of 19BQAs with their parent quinones (FIG. 11) by measuring altered rates of BQA-induced redox cycling in purified hepatic mouse, rat or human microsomes. Oxygen consumption was measured using a Clark electrode after addition of BQAs to NADPH supplemented liver microsomes. Reactions (3 ml) were performed in 50 mM potassium phosphate buffer, pH 7.4 containing 0.5 mM NADPH containing 0.2 mg of human microsomes at 37° C. Reactions were started by the addition of 50 µM BQAs and oxygen consumption was measured over 5 min, and no significant differences in redox cycling rates between all BQAs were found, whether they were 19-substituted or unsubstituted. Similar data was obtained using NADH-dependent redox cycling.

The inventors next tested the effect of 19-substitution of BQAs on hepatotoxicity in isolated hepatocyte systems. Isolated primary mouse hepatocytes were grown on coated 96-well plates and exposed to BQAs for 4 h after which their survival was determined using the MTT assay. The results (expressed as the mean, ±SD, n=3) demonstrate that 19-substitution prevents toxicity in mouse hepatocytes.

Toxicity of the 19BQAs, relative to their parent quinones was then examined using dopaminergic cell systems (SHSY-5Y cells) and their toxicity was markedly decreased relative to their parent quinones. Growth inhibition assays (MTT) were conducted in human SHSY-5Y cells following a 4 hr treatment with GA or 19Me-GA. Cell were allowed to grow for 72 hrs following drug treatment. The 19-methyl substituted compounds in all series were minimally toxic (see FIG. 12 for data with geldanamycin, MTT assay, results are expressed as the mean±SD, n=3). Importantly an $IC_{50}$ for the 19BQAs could not be calculated, while parent quinones exhibited marked toxicity as shown in the following table:

| BQA | SHSY-5Y $IC_{50}$ (µM) |
|---|---|
| GA | 0.133 |
| 19Ph-GA | >10 |
| 19Me-GA | >10 |
| 17AAG | 16.2 |
| 19Ph-17AAG | >20 |
| 19Me-17AAG | >20 |
| DMAG | 9.4 |
| 19Ph-DMAG | >20 |
| 19Me-DMAG | >20 |

Similar data were observed using trypan blue exclusion and apoptosis induction as additional indicators of toxicity.

To ensure 19BQAs were still capable of inhibiting Hsp90, the inventors examined their inhibitory capacity using purified recombinant Hsp90 and demonstrated that the 19BQAs inhibit the ATPase functionality of the Hsp90 chaperone particularly in the presence of NQO1 which generates the hydroquinone ansamycin. This confirms the inventor's previous findings on the superior potency of the hydroquinone ansamycins relative to their parent quinones with respect to inhibition of Hsp90. Biochemical data was also supported by molecular modeling of 19BQAs demonstrating that 19-substitution did not block entry of the molecule into the active site of human Hsp90 and that the hydroquinone derivatives of 19BQAs had more favorable binding energies in the active site of human Hsp90.

The inventors also demonstrated that these 19BQAs inhibit Hsp90 and induce a robust heat shock response in dopaminergic cells. Hsp70 and Hsp27 protein levels were measured in SH-SY5Y cells by immunoblot analysis following treatment with BQAs for 16 hr. Importantly, the desired pharmacological effect of Hsp induction can be observed with 19 BQAs at much lower doses in SHSY-5Y dopaminergic cells (0.25-0.5 µM, FIG. 8, Panel A, Hsp70; panel B, Hsp27) than those that exert toxicity (IC50>20 µM). 19-phenyl and 19-methyl geldanamycin, were of similar potency at inducing Hsp70 and Hsp27 as 17-AAG and geldanamycin. This data demonstrates that 19BQAs are potent inhibitors of Hsp90 and induce a robust protective Hsp response in dopaminergic cells.

In summary, this data demonstrates that the 19-substituted BQAs tested do not react with glutathione at the 19-position, redox cycle at similar rates to their parent BQAs but exhibit little toxicity in both hepatocyte and dopaminergic cellular systems in stark contrast to their parent quinones. 19BQAs retain Hsp90 inhibitory capacity in both purified enzyme systems and in cellular systems and induce a robust protective Hsp response in dopaminergic cells.

Example 7

Design and Testing of Additional 19-Substituted Benzoquinone Ansamycins 19-substituted benzoquinone ansamycins (19BQAs) were rationally designed to minimize off-target effects and hepatotoxicity. Our data demonstrates that the 19BQAs do not arylate cellular thiols validating the rationale for their synthesis. As demonstrated above, the lack of arylation capability translates into a lack of toxicity of novel 19BQAs in freshly isolated mouse hepatocytes.

The inventors have developed isogenic breast and pancreatic cell lines and isogenic xenograft systems varying in the activities of NQO1 to define its role in the mechanism of action of 19BQAs. The inventors have also developed suicide inhibitors of NQO1 and demonstrated that these compounds are selective molecules with fewer off target effects than the competitive inhibitors used previously.

As shown above, 19-Phenyl BQAs have markedly different growth inhibitory effects relative to 19-Me-BQAs. The inventors have tested 19-Me BQAs in multiple cell systems and these molecules are non-toxic despite being as effective Hsp90 ATPase inhibitors as their 19-phenyl analogs. This allows the use of 19-phenyl and 19-methyl BQAs as tools to probe the mechanisms of inhibition of Hsp90 critical for growth inhibition.

The Hsp90 catalytic cycle and the presentation of client proteins to Hsp90 is modulated by co-chaperones including p23, Aha-1 and cdc37 and silencing of any of these co-chaperones has been shown to potentiate response to 17-AAG. Cdc37 chaperones kinase clients critical for growth to Hsp90 including Akt, Raf1 and cdk4 and because of the critical nature of these clients targeting the Hsp90/cdc37 interaction has become an attractive strategy. That all efficient Hsp90 ATPase inhibitors are not created equal and may modulate cell cycle/growth differently depending on effects on individual co-chaperones and downstream clients is consistent with the emerging biology on Hsp90/co-chaperone function. Interrogating the effects of lead 19BQA Hsp90 inhibitors at the level of co-chaperone/Hsp90 interactions is supported by the following data demonstrating differential effects of 19-phenyl and 19-methyl BQAs on the cdc37/Hsp90 interaction.

As demonstrated in Example 6, the inventors have shown metabolism of geldanamycin, 17-AAG, 17-DMAG and other BQAs to their hydroquinone ansamycins using both purified NQO1 and in cellular systems. The inventors next addressed the issue of whether the hydroquinone ansamycin played any functional role in Hsp90 inhibition and growth inhibitory activity induced by BQAs.

The parent BQA's inhibited purified Hsp90 much more readily in the presence of NQO1 to generate the hydroquinone and this could be blocked by the inhibitor ES936. FIG. 13A shows the inhibition of yeast Hsp90 ATPase activity by 17AAG hydroquinone (17AAG+NADH+NQO1). This could be blocked by the NQO1 inhibitor ES936.

Isogenic NQO1-rich breast cancer cells (MDA468-NQ16) formed elevated levels of the hydroquinone metabolites and exhibited much greater Hsp90 and growth inhibitory effects (up to 66 fold depending on time of exposure) relative to their isogenic NQO1-null MDA468 paired cell line. FIGS. 13B and 13C demonstrate a greater than 66-fold decrease in the $IC_{50}$ of 17AAG is observed in MDA468/NQ16 cells compared to MDA468 cells. 17AAG treatment has a greater effect on markers of Hsp90 inhibition (Hsp70 induction and Raf-1 degradation) in MDA468/NQ16 cells compared to MDA468 cells.

The BQA-induced hydroquinone generation, Hsp90 and growth inhibitory effects could all be prevented by use of suicide inhibitors.

Molecular modeling of either benzoquinone or hydroquinone ansamycins in the active ATPase site of Hsp90 demonstrated a much more favorable binding energy for the hydroquinone form. The free OH groups of the hydroquinone were important to the efficient binding of the molecule and formed H-bonds in the ATPase active site of Hsp90. These data demonstrate that the hydroquinone ansamycins are more potent Hsp90 inhibitors than their parent quinones.

Generation of NQO1 isogenic models in both breast and pancreatic systems was based on the identification of tumor cell lines carrying the homozygous NQO1*2 polymorphism characterized in the inventor's laboratory. Cells carrying this homozygous polymorphism are NQO1-null due to rapid proteasomal degradation of the NQO1*2 protein and include MDA-468 breast and Panc-1 pancreatic cancer cells. The inventors have stably transfected NQO1 into the MDA-468 and Panc-1 null backgrounds to generate isogenic pairs of cells which allows for definition of the role of NQO1 in physiological processes and tumor response. The inventors have also generated stable knockdowns of NQO1 in the NQO1-rich pancreatic cell line, MIAPaCa-2. This work can be extended in-vivo where MDA468 and NQ16 xenografts have been established to provide a tool for in-vivo activity comparisons.

The BQA macrocycles are known to adopt an extended trans-amide conformation in the solid state as evidenced by X-ray crystal structure of geldanamycin. In contrast, protein crystallography studies using either yeast or human Hsp90 have shown that on binding, geldanamycin and 17-DMAG adopt a more closed "C-clamp" conformation with a cis-amide bond. 19-substituents on the geldanamycin quinone were designed to block attack by biological nucleophiles and hence ameliorate the hepatotoxicity seen with BQAs. However, the inventors also hypothesized that the 19-substituent might also increase the preference for the adoption of the cis-amide and, consequently, affect the Hsp90 binding affinity and potency of the inhibitors.

Given the limited applicability of literature methods, particularly for the formation of a C—C bond at the 19-position, the inventors investigated a palladium-catalyzed cross-coupling strategy on readily available 19-iodogeldanamycin. After very considerable experimentation, it was found that the Stille reaction was most reliable, and use of 1.2 eq. stannane, 20 mol % triphenylarsine, 5 mol % Pd2(dba)3 and 5 mol % CuI in DMF at 35° C. delivered the desired 19BQAs. Thus, the 19-methyl, -phenyl, vinyl, (2-furyl) and (2-thienyl) geldanamycins were readily prepared. Subsequent reaction with allylamine or 2-diemethylaminoethylamine resulted in conversion into the corresponding 19-substituted 17-AAG and 17-DMAG derivatives. Because of the obvious concern about metal levels in pharmaceutical agents, the inventors undertook a series of ICPMS trace element analyses and following purification, the levels of As, Pd and Sn were at insignificant levels (0.5, 0.4 and 0.1 ppb, respectively).

NMR experiments using a range of techniques confirmed that the compounds had undergone the desired conformation change and were in the cis amide conformation in solution. X-ray crystallography also showed that the 19-(2-furyl) derivative exhibited both the cis-configured amide and also the 'C-clamp' conformation, in contrast to GA itself that adopt a trans-amide conformation in the crystal. A study of the binding of novel 19BQAs to the N-terminal ATPase domain of (yeast) Hsp90 showed that the compounds bind with the cis amide conformation. Hence, all the data demonstrate that the 19BQAs start out in the cis-amide conformation in both solution and solid states, and end up protein bound as cis.

To confirm bioreduction by NQO1 19Ph-GA was incubated with purified human NQO1 and analyzed by HPLC.

The formation of a more water-soluble product, the hydroquinone ansamycin, was observed (FIG. 6A) which was completely inhibited by use of the NQO1 inhibitor ES936. Reactions with purified rhNQO1 (FIG. 14, panels A and B): 19Ph-GA (50 µM) was incubated with NADH (200 µM) in the absence and presence of purified rhNQO1 (5 µg). After 15 min reactions were stopped and analyzed by HPLC. Panel A; chromatograph overlays of 19Ph-GA, NADH (black) and 19Ph-GA, NADH and NQO1 (red). 19Ph-GA (black) is reduced to the more polar 19Ph-GA hydroquinone (red) by NQO1. Panel B; chromatograph of 19Ph-GA, NADH, NQO1 and ES936. No 19Ph-GA hydroquinone formation is observed in the presence of the NQO1 inhibitor ES936.

The ability of 19-substituted BQAs to induce growth inhibition was measured by MTT in isogenic MDA468 (null NQO1) and MDA468/NQ16 (high NQO1) cells. Greater growth inhibition was seen in the NQO1 expressing MDA468/NQ16 cells compared to NQO1-null parental MDA468 cells implicating a role for NQO1 in the cytotoxicity of 19BQAs. Biomarkers of Hsp90 inhibition (Raf-1, AKT degradation and Hsp70 induction) were more pronounced in MDA468/NQ16 cells compared to MDA468 cells following treatment with 19-substituted DMAG analogs. These studies show that in MDA468/NQ16 cells, 19-phenyl DMAG induced more pronounced Raf-1 and AKT degradation and equal Hsp70 induction compared to DMAG. 19-methyl DMAG induced an equivalent Hsp70 response to 19-phenyl DMAG in MDA468/NQ16 (high NQO1) cells indicative of Hsp90 inhibition but had a much less pronounced effect on Hsp90 Raf1 and Akt.

The inventors extended the studies with 19-substituted DMAG analogs to include the Her2+ human breast cancer cell line BT474 (FIG. 15). Growth inhibition (FIG. 15, left panel) was measured in BT474 cells following treatment with analogs for 4 hr. Growth inhibition (MTT) was performed 72 h following drug treatments. Biomarkers of Hsp90 inhibition, Raf-1, AKT, CDK4 and Her2 degradation as well as Hsp70 induction were measured by immunoblot analysis in human BT474 breast cancer cells following treatment with 19-substituted DMAG analogs (5 µM) for 24 hr (FIG. 16, left panel).

Results closely mirrored data obtained using MDA468/NQ16 cells and demonstrated that 19-phenyl DMAG induced growth inhibition while no growth inhibition could be observed with 19-methyl DMAG. In addition, 19-methyl DMAG, in contrast to 19-phenyl DMAG, had diminished effects on Hsp90 client proteins (Raf-1, AKT, Her2, CDK4) while still inducing a robust Hsp70 response indicative of cellular Hsp90 inhibition. Similar effects on biomarkers of Hsp90 inhibition including pronounced Her 2 degradation were obtained using BT474 cells with 19-substituted geldanamycin analogs.

These results clearly demonstrate that phenyl substitutions on the 19-position of the BQA ring results in analogs with near equal potency to the parent BQA while methyl substitutions results in compounds with minimal growth inhibitory activity The inventors also examined the ability of 19 BQAs to inhibit the growth of human pancreatic cancer cell lines (FIG. 16). For growth inhibition studies (MTT) cells were treated with drugs for 4 hr and then allowed to grow for 72 h. For biomarker studies MiaPaCa2 cells were treated with DMAG analogs (5 µM) for 24 hr. 19 BQAs inhibit the growth of human pancreatic cancer cell lines (FIG. 16A, 16B) and induce biomarkers of Hsp90 inhibition (FIG. 16C) using isogenic Panc-1 (NQO1 null) and Panc-1/C5 (NQO1 expressing) cell lines. Consistent with data in breast cancer lines, 19-Ph DMAG showed marked growth inhibitory activity (FIG. 16A) and pronounced induction of biomarkers of Hsp90 inhibition while 19-Me DMAG had little effect (FIG. 16A, and FIG. 16C). Panc-1/C5 cells (high NQO1) were more sensitive to 19Ph-DMAG relative to parental NQO1-null Panc-1 cells (FIG. 16B). Growth inhibition was also assayed in MiaPaCa2 human pancreatic cancer cells treated with 19-substituted DMAG analogs and 19Ph-DMAG was greater than 10-fold more potent than 19Me-DMAG as shown in the following table:

| BQA | IC50 MiaPaCa2 (µM) |
|---|---|
| DMAG | 0.13 ± 0.01 |
| 19Ph-DMAG | 3.0 ± 0.6 |
| 19Me-DMAG | 35.8 ± 5.5 |

As described above, co-chaperones modulate turnover of Hsp90 and also deliver specific clients to Hsp90. Cdc37 has been found to be particularly relevant since it delivers protein kinase clients critical to cell growth and cell cycle to Hsp90 including cdk4, Raf1 and Akt. Thus molecules that can target the ATPase functionality of Hsp90 in addition to affecting interactions with key co-chaperones such as cdc37 represent novel Hsp90 inhibitors.

Forward and reverse immunoprecipitation studies were performed in BT474 cells treated with DMAG analogs (5 µM) for 24 hr. As shown in FIG. 17, 19-phenyl and 19-methyl DMAG disrupted the interaction of p23 and Hsp90, as predicted from molecules that bind at the ATPase site of Hsp90.

Similarly, the association of cdc37 with hsp90 was examined in BT474 cells and MDA468/NQ16 cells by immunoprecipitation following treated with analogs (5 µM) for 24 hr. As shown in FIG. 18A (BT474 cells) and FIG. 18B (MDA468/NQ16 cells), 19-Phenyl DMAG disrupted the interaction of cdc37 with Hsp90 while 19-methyl DMAG, which is not growth inhibitory, had little effect. This finding is consistent with X ray data using purified Hsp90 showing that the larger 19-phenyl substituent causes greater conformational change in the Hsp90 structure than smaller 19-substituents (not shown). This also correlates with the differential effect of 19-phenyl and 19-methyl DMAG on clients chaperoned by cdc37 to Hsp90 which include Raf1, Akt, cdc2 and cdk4 (FIGS. 8,9,10). Effects on these clients were marked with 19-phenyl DMAG while 19-methyl DMAG had little effect.

As described above, a major obstacle in the development of BQA as drugs has been their ability to induce hepatotoxicity in preclinical studies. The inventors examined the hepatotoxicity of DMAG and 19-substituted DMAG analogs in primary mouse hepatocytes and results from these studies clearly demonstrate that 19-substitutions prevented toxicity in mouse hepatocytes (FIG. 19). Treatment of primary mouse hepatocytes with 17-DMAG for 4 hr resulted in significant hepatotoxicity while no toxicity was observed with 19Ph or 19Me-substituted DMAG. Toxicity was measured using MTT assay and confirmed using Trypan Blue and AST leakage. The data shown in FIG. 19 were generated using MTT analysis but similar readouts were obtained using either trypan blue exclusion or leakage of AST from hepatocytes.

The foregoing description of the present invention has been presented for purposes of illustration and description. The description is not intended to limit the invention to the form disclosed herein. Variations and modifications commensurate with the above teachings, and the skill or knowledge of the relevant art, are within the scope of the present invention. The embodiment described hereinabove is further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A compound having the chemical structure of Formula II:

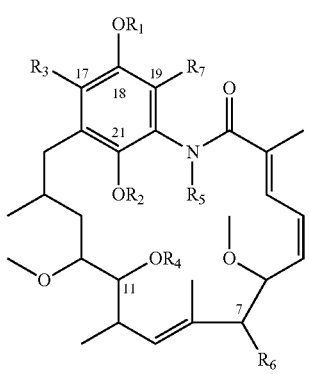

Formula II or a pharmaceutically-acceptable salt thereof;
wherein:
$R_1$ and $R_2$ are independently H, $C_{1-6}$ alkyl, $C_{3-8}$ cycloalkyl, $C(=O)C_{1-10}$ alkyl, $C(=O)(CH_2)_n$-cycloalkyl, $C(=O)(CH_2)_n$-aryl, wherein n=1-10, or alkoxy, alkylthiol, glycoside, glucuronide or sulfate, or $C(=O)CH(X)NH_2$, and $C(=O)CH(X)OH$, wherein X=an amino acid side chain;
$R_3$ is H, alkoxy, azetidinyl, furfuryl, piperidinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, $OR_8$, or $SR_8$,
wherein $R_8$ is H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-ethyl-2-pyrrolidinyl)methyl, or 2-(N-methyl-pyrrolidin-2-yl)ethyl; and, $R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;
$R_6$ is O, $OC(=O)NH_2$, $OC(=O)C_{1-10}$ alkyl, $OSO_2OH$, $OC(=O)OSO_2OH$ and $OC(=O)NR_{10}R_{11}$
wherein $R_{10}$ and $R_{11}$ are independently H and $C_{1-10}$ alkyl; and,
$R_7$ is substituted or unsubstituted aromatic, substituted or unsubstituted heteroaromatic.

2. A compound of claim 1, having the chemical structure of Formula II, wherein:
$R_3$ is H, alkoxy, azetidinyl, furfuryl, piperidinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, $OR_8$, or $SR_8$,
wherein $R_8$ is H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethyletoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-ethyl-2-pyrrolidinyl)methyl, or 2-(N-methyl-pyrrolidin-2-yl)ethyl;
$R_4$ and $R_5$ are H,
$R_6$ is $OC(=O)NH_2$, and,
$R_7$ is phenyl.

3. A compound having the chemical structure:

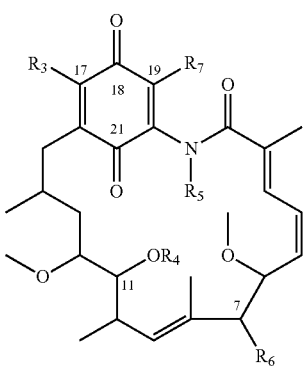

Formula I or a pharmaceutically-acceptable salt thereof;
wherein:
$R_3$ is H, alkoxy, azetidinyl, furfuryl, piperidinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, $OR_8$, or $SR_8$,
wherein $R_8$ is H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-ethyl-2-pyrrolidinyl)methyl, or 2-(N-methyl-pyrrolidin-2-yl)ethyl;

$R_4$ and $R_5$ are independently H, $C_{1-6}$ alkyl, $C_{3-8}$ cycloalkyl, $C(=O)C_{1-10}$ alkyl, $C(=O)(CH_2)_n$-aryl, $C(=O)(CH_2)_n$-cycloalkyl, alkoxy, alkylthiol, glycoside, glucuronide or sulfate, wherein n=1-10;

$R_6$ is O, $OC(=O)NH_2$, $OC(=O)C_{1-10}$ alkyl, $OSO_2OH$, $OC(=O)OSO_2OH$ and $OC(=O)NR_{10}R_{11}$ wherein $R_{10}$ and $R_{11}$ are independently H and $C_{1-10}$ alkyl; and, $R_7$ is substituted or unsubstituted aromatic, substituted or unsubstituted heteroaromatic.

4. A compound of claim 3, having the chemical structure of Formula I, wherein:

$R_3$ is H, alkoxy, azetidinyl, furfuryl, piperidinyl, pyrrolidinyl, tetrahydrofurfuryl, 2-methyl-1-aziridinyl, (dimethylamino)methyl-1-aziridinyl, 3-(dimethylamino)-1-azetidinyl, 3-hydroxy-1-pyrrolidinyl, 3,4-dihydroxy-1-pyrrolidinyl, $OR_8$, or $SR_8$, wherein $R_8$ is H, $C_{1-10}$ alkyl, alkenyl, alkynyl, alkoxy, alkylhalide, alkyldihalide, amine, cycloalkyl, carboxyalkyl, (acetylamino)alkyl, (dimethylamino)alkyl, 1-(methoxymethyl)alkyl, 2-(1,3-dioxolan-2-yl)alkyl, 4,4-dimethoxybutyl, [[(1,1-dimethylethoxy)carbonyl]amino]alkyl, [[(1,1-dimethylethoxy)carbonyl]alkylamino]alkyl, 1-(hydroxymethyl)alkyl, 1-(hydroxymethyl)-2-methylalkyl, 2-(hydroxymethyl)cycloalkyl, (diethylamino)alkyl, 2-(dimethylamino)-1-methylethyl, (ethylmethylamino)alkyl, [(2-fluoroethyl)methylamino]alkyl, [(2,2-difluoroethyl)methylamino]alkyl, [bis(2-hydroxyethyl)amino]alkyl, (dimethyloxidoamino)alkyl, (trimethylammonio)alkyl, (1-azetidinyl)alkyl, (2-deoxy-D-glucos-2-yl), (6-deoxy-D-glucos-6-yl), (1H-imidazol-4-yl)alkyl, (1-methyl-1H-imidazol-4-yl)alkyl, (1-methyl-1H-imidazol-5-yl)alkyl, (4-morpholinyl)alkyl, (4-pyridinyl)alkyl, (1-piperidinyl)alkyl, (1-piperazinyl)alkyl, (1-ethyl-2-pyrrolidinyl)methyl, or 2-(N-methyl-pyrrolidin-2-yl)ethyl;

$R_4$ and $R_5$ are H, $R_6$ is $OC(=O)NH_2$, and, $R_7$ is phenyl.

5. A method of treating cancer comprising administering a therapeutically effective amount of a compound of claim 1, or a pharmaceutically acceptable salt form thereof, to a mammal in need of such treatment.

6. A method of treating Parkinson's disease, or ameliorating a symptom thereof, comprising administering a therapeutically effective amount of a compound of claim 1, or a pharmaceutically acceptable salt thereof, to a mammal in need of such treatment.

7. The method of claim 6, wherein the compound administered is present in the cis-confirmation.

8. The method of claim 5, wherein the compound is administered in conjunction with at least one of a tyrosine kinase inhibitor, paclitaxel and doxorubicin.

9. The method of claim 5, wherein the compound is administered in conjunction with medically supervised radiation therapy.

* * * * *